US011345739B2

(12) United States Patent
Diem et al.

(10) Patent No.: US 11,345,739 B2
(45) Date of Patent: *May 31, 2022

(54) CD137 BINDING FIBRONECTIN TYPE III DOMAINS

(71) Applicant: Janssen Biotech, Inc., Horsham, PA (US)

(72) Inventors: Michael Diem, Havertown, PA (US); Rebecca Hawkins, Harleysville, PA (US); Steven Jacobs, North Wales, PA (US); Manuel Sepulveda, Princeton Junction, NJ (US)

(73) Assignee: JANSSEN BIOTECH, INC, Horsham, PA (US)

( * ) Notice: Subject to any disclaimer, the term of this patent is extended or adjusted under 35 U.S.C. 154(b) by 10 days.

This patent is subject to a terminal disclaimer.

(21) Appl. No.: 16/820,844

(22) Filed: Mar. 17, 2020

(65) Prior Publication Data

US 2021/0040180 A1    Feb. 11, 2021

Related U.S. Application Data

(63) Continuation of application No. 15/840,303, filed on Dec. 13, 2017, now Pat. No. 10,611,823.

(60) Provisional application No. 62/434,064, filed on Dec. 14, 2016.

(51) Int. Cl.
| | |
|---|---|
| *C07K 14/78* | (2006.01) |
| *G01N 33/53* | (2006.01) |
| *G01N 33/574* | (2006.01) |
| *A61P 35/00* | (2006.01) |
| *C12N 15/85* | (2006.01) |
| *C07K 14/705* | (2006.01) |
| *G01N 33/68* | (2006.01) |
| *C07K 14/71* | (2006.01) |
| *A61K 38/39* | (2006.01) |
| *G01N 33/566* | (2006.01) |

(52) U.S. Cl.
CPC .............. *C07K 14/78* (2013.01); *A61P 35/00* (2018.01); *C07K 14/705* (2013.01); *C07K 14/70596* (2013.01); *C12N 15/85* (2013.01); *G01N 33/53* (2013.01); *G01N 33/574* (2013.01); *G01N 33/57492* (2013.01); *G01N 33/6893* (2013.01); *A61K 38/39* (2013.01); *C07K 2319/31* (2013.01); *C07K 2319/40* (2013.01)

(58) Field of Classification Search
CPC ............ C07K 14/705; C07K 14/70596; C07K 14/47; C07K 14/78; C07K 2319/00; C07K 2319/31; A61K 38/17; A61K 38/39
See application file for complete search history.

(56) References Cited

U.S. PATENT DOCUMENTS

| | | |
|---|---|---|
| 4,281,061 A | 7/1981 | Zuk et al. |
| 5,223,409 A | 6/1993 | Ladner et al. |
| 5,643,763 A | 7/1997 | Dunn et al. |
| 5,643,768 A | 7/1997 | Kawasaki |
| 5,658,727 A | 8/1997 | Barbas et al. |
| 5,691,157 A | 11/1997 | Gong et al. |
| 5,846,456 A | 12/1998 | Liu |
| 5,856,456 A | 1/1999 | Whitlow et al. |
| 6,018,030 A | 1/2000 | Ferrari et al. |
| 6,162,903 A | 12/2000 | Trowern et al. |
| 6,172,197 B1 | 1/2001 | McCafferty et al. |
| 6,355,776 B1 | 3/2002 | Ferrari et al. |
| 6,462,189 B1 | 10/2002 | Koide |
| 6,472,147 B1 | 10/2002 | Janda et al. |
| 6,521,427 B1 | 2/2003 | Evans |
| 6,582,915 B1 | 6/2003 | Griffiths et al. |
| 6,670,127 B2 | 12/2003 | Evans |
| 6,673,901 B2 | 1/2004 | Koide |
| 6,703,199 B1 | 3/2004 | Koide |
| 6,818,418 B1 | 11/2004 | Lipovsek et al. |
| 6,846,655 B1 | 1/2005 | Wagner et al. |
| 6,969,108 B2 | 11/2005 | Fukumoto et al. |
| 7,078,490 B2 | 7/2006 | Koide |
| 7,115,396 B2 | 10/2006 | Lipovsek et al. |
| 7,119,171 B2 | 10/2006 | Koide |
| 7,153,661 B2 | 12/2006 | Koide |
| 7,288,638 B2 | 10/2007 | Jure-Kunkel et al. |
| 7,427,672 B2 | 9/2008 | Imanishi et al. |
| 7,709,214 B2 | 5/2010 | Freeman et al. |
| 7,794,710 B2 | 9/2010 | Chen et al. |
| 7,842,476 B2 | 11/2010 | McGregor et al. |
| 7,943,743 B2 | 5/2011 | Korman et al. |
| 8,217,149 B2 | 7/2012 | Irving et al. |
| 8,278,419 B2 | 10/2012 | Jacobs et al. |
| 8,293,482 B2 | 10/2012 | Jacobs et al. |

(Continued)

FOREIGN PATENT DOCUMENTS

| | | |
|---|---|---|
| CN | 102076713 A | 5/2011 |
| CN | 103827361 A | 5/2014 |
| CN | 105907719 A | 8/2016 |
| EP | 0985039 A2 | 3/2000 |
| EP | 1137941 A1 | 10/2001 |

(Continued)

OTHER PUBLICATIONS

Gill et al., "Monoclonal Anti-epidermal Growth Factor Receptor Antibodies Which Are Inhibitors of Epidermal Growth racier Binding and Antagonists of Epidermal Growth Factor-stimulated tyrosine Protein Kinase Activity," The Journal Jf Biological Chemistry, vol. 259, No. 12, pp. 7755-7760 (1984).

(Continued)

*Primary Examiner* — Bridget E Bunner
(74) *Attorney, Agent, or Firm* — Troutman Pepper Hamilton Sanders LLP

(57) ABSTRACT

FN3 domains that specifically bind to CD137, their conjugates, isolated nucleotides encoding the molecules, vectors, host cells, and methods of making and using them are useful in therapeutic and diagnostic applications.

20 Claims, No Drawings

Specification includes a Sequence Listing.

(56) References Cited

U.S. PATENT DOCUMENTS

| | | |
|---|---|---|
| 8,552,154 B2 | 10/2013 | Freeman et al. |
| 8,569,227 B2 | 10/2013 | Jacobs |
| 8,741,295 B2 | 6/2014 | Olive |
| 8,779,108 B2 | 7/2014 | Queva et al. |
| 8,981,063 B2 | 3/2015 | Chen |
| 9,156,887 B2 | 10/2015 | Jacobs |
| 9,175,082 B2 | 11/2015 | Zhou et al. |
| 9,200,273 B2 | 12/2015 | Diem et al. |
| 9,212,224 B2 | 12/2015 | Cogswell et al. |
| 9,326,941 B2 | 5/2016 | Chae et al. |
| 9,546,368 B2 | 1/2017 | Bennett et al. |
| 9,644,023 B2 | 5/2017 | Torres et al. |
| 9,695,228 B2 | 7/2017 | Mark et al. |
| 9,897,612 B2 | 2/2018 | Diem et al. |
| 10,196,446 B2 | 2/2019 | Goldberg et al. |
| 10,233,448 B2 | 3/2019 | Maier et al. |
| 10,597,438 B2 | 3/2020 | Diem et al. |
| 10,611,823 B2 * | 4/2020 | Diem .................. C07K 14/705 |
| 10,626,165 B2 | 4/2020 | Hawkins et al. |
| 2004/0197332 A1 | 10/2004 | Ullrich et al. |
| 2004/0259781 A1 | 12/2004 | Chiquet-Ehrismann et al. |
| 2005/0004029 A1 | 1/2005 | Garcia |
| 2005/0038229 A1 | 2/2005 | Lipovsek et al. |
| 2005/0255548 A1 | 11/2005 | Lipovsek et al. |
| 2005/0272083 A1 | 12/2005 | Seshagiri |
| 2006/0040278 A1 | 2/2006 | Cojocaru et al. |
| 2006/0246059 A1 | 11/2006 | Lipovsek et al. |
| 2006/0270604 A1 | 11/2006 | Lipovsek et al. |
| 2007/0148126 A1 | 6/2007 | Chen et al. |
| 2007/0160533 A1 | 7/2007 | Chen et al. |
| 2007/0184476 A1 | 8/2007 | Hsieh et al. |
| 2008/0015339 A1 | 1/2008 | Lipovsek et al. |
| 2008/0220049 A1 | 9/2008 | Chen et al. |
| 2008/0241159 A1 | 10/2008 | Gerritsen et al. |
| 2009/0042906 A1 | 2/2009 | Huang et al. |
| 2009/0176654 A1 | 7/2009 | Cappuccilli et al. |
| 2009/0274693 A1 | 11/2009 | Gilmer et al. |
| 2009/0299040 A1 | 12/2009 | Camphausen et al. |
| 2009/0311803 A1 | 12/2009 | Way et al. |
| 2010/0144601 A1 | 6/2010 | Jacobs et al. |
| 2010/0179094 A1 | 7/2010 | Emanuel et al. |
| 2010/0216708 A1 | 8/2010 | Jacobs et al. |
| 2010/0254989 A1 | 10/2010 | Bossenmaier et al. |
| 2010/0255056 A1 | 10/2010 | Jacobs et al. |
| 2011/0038866 A1 | 2/2011 | Hastewell et al. |
| 2011/0053842 A1 | 3/2011 | Camphausen et al. |
| 2011/0081345 A1 | 4/2011 | Moore et al. |
| 2011/0118144 A1 | 5/2011 | Hyun et al. |
| 2011/0124527 A1 | 5/2011 | Cappuccilli et al. |
| 2011/0274623 A1 | 11/2011 | Jacobs |
| 2011/0287009 A1 | 11/2011 | Scheer et al. |
| 2012/0225870 A1 | 9/2012 | Janne et al. |
| 2012/0244164 A1 | 9/2012 | Beste et al. |
| 2012/0263723 A1 | 10/2012 | Davies et al. |
| 2012/0270797 A1 | 10/2012 | Wittrup et al. |
| 2012/0315639 A1 | 12/2012 | Deng et al. |
| 2012/0321666 A1 | 12/2012 | Cooper et al. |
| 2013/0012435 A1 | 1/2013 | Camphausen et al. |
| 2013/0039927 A1 | 2/2013 | Dewhurst et al. |
| 2013/0184212 A1 | 7/2013 | Camphausen et al. |
| 2013/0226834 A1 | 8/2013 | Gannalo, II |
| 2013/0273561 A1 | 10/2013 | Walker et al. |
| 2014/0141000 A1 | 5/2014 | Chiu et al. |
| 2014/0155325 A1 | 6/2014 | Mark et al. |
| 2014/0155326 A1 | 6/2014 | Mark et al. |
| 2014/0255408 A1 | 9/2014 | Chiu et al. |
| 2014/0271467 A1 | 9/2014 | Hackel et al. |
| 2014/0341917 A1 | 11/2014 | Nastri et al. |
| 2014/0349929 A1 | 11/2014 | Camphausen et al. |
| 2014/0371296 A1 | 12/2014 | Bennett et al. |
| 2015/0005364 A1 | 1/2015 | Chae et al. |
| 2015/0104808 A1 | 4/2015 | Goldberg et al. |
| 2015/0118288 A1 | 4/2015 | Lee |
| 2015/0197571 A1 | 7/2015 | Freeman et al. |
| 2015/0203580 A1 | 7/2015 | Papadopoulos et al. |
| 2015/0252097 A1 | 9/2015 | Camphausen et al. |
| 2015/0274835 A1 | 10/2015 | Marasco et al. |
| 2015/0346208 A1 | 12/2015 | Couto et al. |
| 2015/0355184 A1 | 12/2015 | Pierce et al. |
| 2016/0041182 A1 | 2/2016 | Diem et al. |
| 2016/0303256 A1 | 10/2016 | Liu |
| 2016/0326232 A1 | 11/2016 | Rosa et al. |
| 2016/0355599 A1 | 12/2016 | Sagert et al. |
| 2017/0174748 A1 | 6/2017 | Mitchell et al. |
| 2017/0258948 A1 | 9/2017 | Morin et al. |
| 2017/0348397 A1 | 12/2017 | Diem et al. |
| 2017/0362301 A1 | 12/2017 | Anderson et al. |
| 2019/0127444 A1 | 5/2019 | Brezski et al. |
| 2019/0175651 A1 | 6/2019 | Lee et al. |
| 2019/0184018 A1 | 6/2019 | Manoharan et al. |
| 2019/0184028 A1 | 6/2019 | Dudkin et al. |
| 2019/0202927 A1 | 7/2019 | Sagert et al. |
| 2019/0256575 A1 | 8/2019 | Chen et al. |
| 2019/0263915 A1 | 8/2019 | Goldberg et al. |
| 2019/0330361 A1 | 10/2019 | Chin et al. |

FOREIGN PATENT DOCUMENTS

| | | |
|---|---|---|
| EP | 1210428 A1 | 6/2002 |
| EP | 1266025 A1 | 12/2002 |
| EP | 2935329 A1 | 10/2015 |
| JP | 2011507543 A | 3/2011 |
| JP | 2011517314 A | 6/2011 |
| JP | 2011520961 A | 7/2011 |
| JP | 2011522517 A | 8/2011 |
| WO | 9638557 A1 | 12/1996 |
| WO | 2001014557 A1 | 3/2001 |
| WO | 0164942 A1 | 9/2001 |
| WO | 0232925 A2 | 4/2002 |
| WO | 03104418 A2 | 12/2003 |
| WO | 2004029224 A2 | 4/2004 |
| WO | 2004058821 A2 | 7/2004 |
| WO | 2005018534 A2 | 3/2005 |
| WO | 2005042708 A2 | 5/2005 |
| WO | 2007000671 A2 | 1/2007 |
| WO | 2007085815 A2 | 8/2007 |
| WO | 2008079973 A2 | 7/2008 |
| WO | 2008127710 A2 | 10/2008 |
| WO | 2008156642 A1 | 12/2008 |
| WO | 2009023184 A2 | 2/2009 |
| WO | 2009058379 A2 | 5/2009 |
| WO | 2009083804 A2 | 7/2009 |
| WO | 2009085462 A1 | 7/2009 |
| WO | 2009086116 A2 | 7/2009 |
| WO | 2009102421 A2 | 8/2009 |
| WO | 2009111691 A2 | 9/2009 |
| WO | 2009126834 A2 | 10/2009 |
| WO | 2009133208 A1 | 11/2009 |
| WO | 2009142773 A2 | 11/2009 |
| WO | 2010039248 A1 | 4/2010 |
| WO | 2010051274 A2 | 5/2010 |
| WO | 2010051310 A2 | 5/2010 |
| WO | 2010060095 A1 | 5/2010 |
| WO | 2010093627 A3 | 10/2010 |
| WO | 2010115202 A2 | 10/2010 |
| WO | 2010115551 A1 | 10/2010 |
| WO | 2011005133 A1 | 1/2011 |
| WO | 2011110642 A2 | 9/2011 |
| WO | 2011130324 A1 | 10/2011 |
| WO | 2011131746 A2 | 10/2011 |
| WO | 2011137319 A2 | 11/2011 |
| WO | 2011151412 A1 | 12/2011 |
| WO | 2012016245 A2 | 2/2012 |
| WO | 2013049275 A1 | 4/2013 |
| WO | 2014081944 A2 | 5/2014 |
| WO | 2014081954 A1 | 5/2014 |
| WO | 2014100079 A1 | 6/2014 |
| WO | 2014165082 A2 | 10/2014 |
| WO | 2014165093 A2 | 10/2014 |
| WO | 2014189973 A2 | 11/2014 |
| WO | 2014209804 A1 | 12/2014 |
| WO | 2015061668 A1 | 4/2015 |
| WO | 2015092393 A2 | 6/2015 |
| WO | 2015109124 A2 | 7/2015 |

(56) References Cited

FOREIGN PATENT DOCUMENTS

| WO | 2015195163 | A1 | 12/2015 |
|---|---|---|---|
| WO | 2016000619 | A1 | 1/2016 |
| WO | 2016004043 | A1 | 1/2016 |
| WO | 2016086021 | A1 | 6/2016 |
| WO | 2016086036 | | 6/2016 |
| WO | 2016179534 | | 11/2016 |
| WO | 2016197071 | A1 | 12/2016 |
| WO | 2017011618 | A1 | 1/2017 |

OTHER PUBLICATIONS

Goldstein et al., "Biological efficacy of a chimeric antibody to the epidermal growth factor receptor in a human umor xenografl model," Clinical Cancer Research, vol. 1, pp. 1311-1318 (1995).
Grünwald et al., "Developing Inhibitors of the Epidermal Growth Factor Receptor for Cancer Treatment," Journal of the National Cancer Institute, vol. 95, No. 12, pp. 851-867 (2003).
Hirsch et al., "Combination of EGFR gene copy number and protein expression predicts outcome for advanced non- , mall-cell lung cancer patients treated with gefitnib," Annals of Oncology, vol. 18, pp. 752-760 (2007).
Hynes et al., "ERBB Receptors and Cancer: the Complexity of Targeted Inhibitors," Nature Reviews, vol. 5, pp. 341-356 (2005).
Chimu Ra et al., "Expression of c-mel/HGF Receptor in Human Non-small Cell Lung Carcinomas in vitro and in vivo and Its Prognostic Significance," Japan Journal of Cancer Research, vol. 87. pp. 1063-1069 (1996).
Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pp. 4416s-4420s (2006).
Jacobs et al., "FN3 Domain Engineering", Protein Engineering, pp. 145-162, 2012.
Li et al., "Skin toxicities associated with epidermal growth factor receptor inhibitors," Target Oncology, vol. 4, pp. 107-119 (2009).
Linardou et al., "Somatic EGFR mutations and efficacy of tyrosine kinase inhibitors in NSCLC," National Review of :; linical Oncology, vol. 6, pp. 352-366 (2009).
Ma et al., "c-Met: Structure, functions and potential for therapeutic inhibition," Cancer and Metastasis Reviews, vol. 22 pp. 309-325 (2003).
Mendelsohn et al., "Epidermal Growth Factor Receptor Targeting in Cancer," Seminars in Oncology, vol. 33, pp. 369-385 (2006).
Mendelsohn et al., "The EGF receptor family as targets for cancer therapy," Oncogene, vol. 19, pp. 6550-6565 2000).
Määttä et al., "Proteolytic Cleavage and Phosphorylation of a Tumor-associated ErbB4 Isoform Promote Ligand-ndependent Survival and Cancer Cell Growth," Molecular Biology, vol. 17, pp. 67-79 (2006).
NCBI Reference Sequence NP _005219.2, "Epidermal Growth Factor Receptor Isoform a Precursor [Homo sapiens]," pp. 1-14 (May 18, 2014).
Panek et al.,"In Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444 (1997).
Peters et al., "MET: a promising anticancer therapeutic target," Nature Reviews Clinical Oncology, vol. 9, pp. 314-326 (2012).
Prewett et al., "Mouse-Human chimeric Anti-Epidermal Growth Factor Receptor Antibody C225 Inhibits the Growth Jf Human Renal Cell Carcinoma Xenografts in Nude Mice," Clinical Cancer Research, vol. 4, pp. 2957-2966 (1998).
Riel Yet al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, vol. 12, No. 3, pp. g39-844 (2006).

Sakakura et al., "Gains, Losses, and Amplifications of Genomic Materials in Primary Gastric Cancers Analyzed by :; omparative Genomic Hybridization," Genes, Chromosomes & Cancer, vol. 24, pp. 299-305 (1999).
Schmidt et al., "Novel mutations of the MET proto-0ncogene in papillary rental carcinomas," Oncogene, vol. 18, pp. ]343-2350 (1999).
Siegfried et al., "The Clinical Significance of Hepatocyte Growth Factor for Non-Small Cell Lung Cancer," Annals of Thoracic Surgery, vol. 66, pp. 1915-1918 (1998).
Sierra et al., "c-MET as a potential therapeutic target and biomarker in cancer," Therapeutic Advances in Medical :: <ncology, vol. 3, No. 51, pp. 521-535 (2011).
Stamos et al., "Crystal structure of the HGF b-chain in complex with the Sema domain of the Met receptor," The EMBO Journal, vol. 23, pp. 2325-2335 (2004).
Mamluk et al., "Anti-tumor effect of CT-322 as an Adnectin inhibitor of vascular endothelial growth factor receptor-2", mAbs, 2(2), pp. 199-208, 2010.
Klein et al. "Abstract LB-312: Bispecific Centyrin Simultaneously targeting EGFR and c--Met demonstrates improved ô €?'ctivity compared to the mixture of single agents", Cancer Research, 73 (8 Supplement), Abstract LB-312, Apr. 2013.
Jacobs et al., "Fusion to a highly stable consensus albumin binding domain allows for tunable pharmacokinetics", Protein Engineering, Design & Selection, vol. 28, No. 10, pp. 385-393, 2015.
Notice of Allowance dated Mar. 3, 2020 in U.S. Appl. No. 15/840,303.
Makkouk Amani et al: "Rationale for anti-CD137 cancer immunotherapy", European Journal of Cancer, Elsevier, Amsterdam, NL, vol. 54, Jan. 2, 2016 (Jan. 2, 2016), pp. 112-119, XP029401784, ISSN: 0959-8049, DOI: 10.1016/j.ejca.2015.09.026 *abstractp. 114, right-hand column, paragraph 4—p. 116, right-hand column paragraph 1table 1*.
Shalom D. Goldberg et al: "Engineering a targeted delivery platform using Centyrins", Protein Engineering, Design and Selection, Oct. 13, 2016 (Oct. 13, 2016), XP055384705, GB ISSN: 1741-0126, DOI: 10.1093/protein/gzw054 *abstractp. 564, left-hand column, paragraph 2—right-hand column line 3 p. 567, right-hand column, paragraph 2p. 568, right-hand column, paragraph 2—p. 569, left-hand column, paragraph 2table I**figure 1a*.
Burton Earle Barnett et al: "Disclosures", Blood, vol. 128, No. 22, Dec. 2, 2016 (Dec. 2, 2016), pp. 4557-4557, XP055711182, US ISSN: 0006-4971, doi: 10.1182/blood.V128.22.4557.4557 *abstract*.
Final Office Action dated Jul. 10, 2020 in U.S. Appl. No. 15/637,276.
Zucali, et al., "Role of cMET expression in non-small-cell lung cancer patients treated with eGFR tyrosine kinase inhibitors", Annals of Anocology (2008) 19:: 1605-1612.
Skerra, et al., "Engineered protein scaffolds for molecular recognition," Journal of Molecular Recognition, 13: 167-187 (2000).
Koide, et al., "The Fibronectin Type III Domain as a Scaffold for Novel Binding Proteins," Journal of Molecular Biology, 284: 1141-1151 (1998).
Karatan, et al., "Molecular Recognition Properties of FN3 Mono bodies that Bind the Src SH3 Domain," Chemistry & Biology, 11:835-844 (2004).
Parker, et al., "Antibody mimics based on human fibronectin type three domain engineered for thermostability and high-affinity binding to vascular endothelial growth factor receptor two," Protein Engineering, Design & Selection, 18(9):435-444 (2005).
Siggers et al. Conformational dynamics in loop swap mutants of homologous fibronectin type III domains. Biophys J. Oct. 1, 2007 ;93(7):2447-56.
Skolnick et al. From genes to protein structure and function: novel applications of computational approaches in the genomic era. Trends Biotechnol. 18(1 ):34-9, 2000.
Attwood TK. Genomics. The Babel of bioinformatics. Science. 290(5491 ):471-473, 2000.
Miller et al. Ligand binding to proteins: the binding landscape model. Protein Sci. Oct. 1997;6(10):2166-79.
Kuntz. Structure-based strategies for drug design and discovery. Science. 1992 257(5073):1078-1082.
Koivunen et al. Identification of Receptor Ligands with Phage Display Peptide Libraries J Nucl Med; 40:883-888, 1999.

(56) References Cited

OTHER PUBLICATIONS

Reiss et al. Inhibition of platelet aggregation by grafting RGD and KGD sequences on the structural scaffold of small disulfide-rich proteins. Platelets 17(3):153-157, 2006.

Helms et al. Destabilizing loop swaps in the CDRs of an immunoglobulin VL domain. Protein Science 4:2073-2081, 1995.

Bass, et al., "Hormone Phage: An Enrichment Method for Variant Proteins with Altered Binding Properties," Proteins: Structure, Function, and Genetics, 8: 309-314 (1990).

Clarke, et al., "Folding and Stability of a Fibronectin Type III Domain of Human Tenascin," Journal of Molecular Biology, 270: 771-778 (1997).

Dehouck, et al., "Fast and accurate predictions of protein stability changes upon mutations using statistical potentials and neural networks: PoPMuSiC—2.0," Bioinformatics, 25(19): 2537-2543 (2009).

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).

Dutta, et al., "High-affinity fragment complementation of a fibronectin type III domain and its application to stability enhancement," Protein Science, 14: 2838-2848 (2005).

Garrard, et al., "Selection of an anti-IGF-1 Fab from a Fab phage library created by mutagenesis of multiple CDR loops," Gene, 128: 103-109 (1993).

Getmanova, et al., "Antagonists to Human and Mouse Vascular Endothelial Growth Factor Receptor 2 Generated by Directed Protein Evolution In Vitro," Chemistry & Biology, 13: 549-556 (2006).

Hackel, et al., "Stability and CDR Composition Biases Enrich Binder Functionality Landscapes," Journal of Molecular Biology, 401: 84-96 (2010).

Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).

Koide, et al., Teaching an Old Scaffold New Tricks: Monobodies Constructed Using Alternative Surfaces of the FN3 Scaffold, Journal of Molecular Biology, 415: 393-405 (2012).

Lipovsek, et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 368: 1024-1041 (2007).

C.N. Pace, "Determination and Analysis of Urea and Guanidine Hydrochloride Denaturation Curves," Methods in Enzymology, 131: 266-280 (1986).

Steiner, et al., "Efficient Selection of DARPins with Sub-nonomolar Affinities using SRP Phage Display," Journal of Molecular Biology, 382:1211-1227 (2008).

Xu, et al., "Directed Evolution of High-Affinity Antibody Mimics Using mRNA Display," Chemistry & Biology, 9: 933-942 (2002).

Cota, et al., "Two Proteins with the Same Structure Respond very Differently to Mutation: The Role of Plasticity in Protein Stability", Journal of Molecular Biology, 302, 713-725 (2000).

Hamill et al., "The Effect of Boundary Selection on the Stability and Folding of the Third Fibronectin Type III Domain from Human Tenascin", Biochemistry, 37: 8071-8079 (1998).

Garcia-Ibilcieta, et al., "Simple method for production of randomized human tenth fibronectin domain III libraries for use in combinatorial screening procedures," Bio Technologies, 44: 559-562 (2008).

Van den Burg et al., "Selection of mutations for increased protein stability", Curr. Opin. Biotech. 13:333-337 (2002).

GenBank Accession No. NP_002151, May 9, 2020.

Slonomics® Technology Website "https://www.morphosys.com/science/drug-development-capabilities/slonomics", May 12, 2020.

SwissProt Accession No. P00533.2, "Epidermal Growth Factor Receptor," pp. 1-49 (Jun. 11, 2014).

Turke et al., "Preexistence and Clonal Selection of MET Amplification in EGFR Mutant NSCLC," Cancer Cell, vol. 17, pp. 77-88 (2010).

Ullrich et al., "Human epidermal growth factor receptor cDNA sequence and aberrant expression of the amplified Jene in A431 epidermoid carcinoma cells," Nature, vol. 309, pp. 418-425 (1984).

Zhang et al., "Complete disulfide bond assignment of a recombinant immunoglobulin G4 monoclonal antibody," Analytical Biochemistry, vol. 311, pp. 1-9 (2002).

Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 (2011).

Basel GA et al., "Critical Update and Emerging Trends in Epidermal Growth Factor Receptor Targeting in Cancer," Journal of Clinical Oncology, vol. 23, No. 11, pp. 2445-2459 (2005).

Batley et al., "Inhibition of FGF-1 Receptor Tyrosine Kinase Activity By PD 161570, a New Protein-Tyrosine Kinase nhibitor," Life Sciences, vol. 62, No. 20, pp. 143-150 (1998).

Bean et al., "MET amplification occurs with or without T790M mutations in EGFR mutant lung tumors with acquired esistance to gefilinib or erlotinib," Proceedings of the National Academy of Science, vol. 104, No. 52, pp. 3932-20937 (2007).

Cappuzzo et al., "Epidermal Growth Factor Receptor Gene and Protein and Gefilinib Sensitivity in Non-small-Cell lung Cancer," Journal of the National Cancer Institute, vol. 97, pp. 643-655 (2005).

Christensen et al., "c-Met as a target for human cancer and characterization of inhibitors for therapeutic ntervention," Cancer Letters, vol. 225, pp. 1-26 (2005).

Cooper et al., "Molecular cloning of a new transforming gene from a chemically transformed human cell line," Nature, vol. 311, pp. 29-33 (1984).

Deroock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).

Downward et al., "Autophosphorylation sites on the epidermal growth factor receptor," Nature, vol. 311, pp. 183-485 (1984).

Engelman et al., "MET Amplification Leads to Gefitinib Resistance in Lung Cancer by Activating ERBB3 Signaling," Science, vol. 316, pp. 1039-1043 (2007).

Ferguson, Kathryn M., "Structure-Based View of Epidermal Growth Factor Receptor Regulation," Annual Review of Biophysics, vol. 37, pp. 535-373 (2008).

GenBank Accession No. NP 001120972, Apr. 20, 2020.

Burgess et al., "Possible dissociation of the heparin-binding and mitogenic activities of heparin-binding (acidic fibroblast) growth factor-1 from its receptor-binding activities by site-directed mutagenesis of a single lysine residue" J Cell Biol (1990) 111:pp. 2129-2138.

Lazar et al., "Transforming growth factor alpha: mutation of aspartic acid 47 and leucie 48 results in different biological activities", Mol Cell Biol. (1988) 8: pp. 1247-1252.

Brown et al., "Tolerance of single, but not multiple, amino acid replacements in antibody VH CDR 2: a means of minimizing B cell wastage from somatic hypermutation", J. Immuno. (1996) pp. 3285-3291.

Rudikoff el al., "Single amino acid substitution altering antigen-binding specificity", Proc Natl Acad Sci (1982) 79(6): pp. 1979-1983.

Vajdos et al., "Comprehensive funtional maps of the antigen-binding site of an anti-ErbB2 antibody obtained with shotgun scanning mutagenisis", J. Mol. Biol. (2002) 32(2): pp. 415-428.

Non-Final Office Action dated Jul. 9, 2021 in 16821064.

Rybalov et al., "PSMA, EpCAM, VEGF and GRPR as Imaging Targets in Locally Recurrent Prostate Cancer after Radiotherapy", Int. J. Mol. Sci. (2014) 15, pp. 6046-6061.

Non-Final Office Action dated Feb. 3, 2021 in U.S. Appl. No. 16/218,990.

Final Office Action dated Jul. 21, 2020 in U.S. Appl. No. 16/218,990.

(56) References Cited

OTHER PUBLICATIONS

Lejon et al., "Structural basis for the binding of naproxen to human serum albumin in the presence of fatty acids and the GA module", Acta Cryst. (2008) F pp. 64-69.

Lee et al., "A Glu-ruea-Lys Ligand-conjugated Lipid nanoparticle/siRNA System Inhibits Androgen Receptor Expression In Vivo", Molecular Therapy-Nucleic Acids (2016) 5, e348: pp. 1-11.

Pace, "Determination and Analysis of Urea and Guanidine Hydrochloride Denaturation Curves", Methods in Enzymology (1986) vol. 131, pp. 266-280.

Chen et al., "Cell-Surface Display of Heterologous Proteins: From High-Throughput Screening to Environmental Applications", Biotechnology and Bioengineering, (2002) vol. 79, No. 5, pp. 496-503.

Mattheakis et al., "An in vitro polysome display system for identifying ligands from very large peptide libraries", Proc. Natl. Acad. Sci. (1994) Vo. 91, pp. 9022-9026.

Hoogenboom et al., "Natural and designer binding sites made by phage display technology" Immunology Today (2000) vol. 21, No. 8, pp. 371-378.

Smith, "Filamentous fusion phage: novel expression vectors that display cloned antigens on the virion surface.", Association of Science (1985) vol. 228, pp. 1315(3).

Capellas, "Enzymatic Condensation of Cholecystokinin CCK-8 (4-6) and CCK-8 (7-8) Peptide Fragments in Organic Media", Biotechnology and Bioengineering (1997) vol. 56, No. 4, pp. 456-463.

Itoh, et al., "Application of Inverse Substrates to Trypsin-Catalyzed Peptide Synthesis", Bioorganic Chemistry (1996) 24, 0007, pp. 59-68.

Kumaran et al., "Confrmationally driven protease-catalyzed splicing of peptide segments: V8 protease-mediated syntheses of fragments derived from thermolysin and ribonuclease A", Protein Science, (1997) 6: pp. 2233-2241.

Kunkel et al., "Rapid and Efficient Site-Specific Mutagenesis without Phenotypic Selection", Methods in Enzymology, (1987) vol. 154 pp. 367-375.

Wattanachaisaereekul, "Production of Polyketides by *Saccharomyces cerevisiae*", Ph.D. Thesis (2007) Center for Microbial Biotechnology, BioCentrum-DTU Technical University of Denmark, pp. 1-187.

Hackel et al., "Use of 64Cu-Labeled Fibronectin Domain with EGFR-Overexpressing Tumor Xenograft: Molecular Imaging1", Radiology (2012) vol. 263:No. 1 pp. 179-188.

Non-Final Office Action dated Aug. 18, 2021 in U.S. Appl. No. 16/801,787.

McCracken, "Non-invasive monitoring of hematopoietic reconstitution and immune cell function through Positron Emission Tomography" University of California, Los Angeles, Dissertaton ProQuest LLC (2014) pp. 1-202.

Natarajan, et al., "A Novel Engineered Anti-CD20 Tracer Enables Early Time PET Imaging in a Humanized Transgenic Mouse Model of B-cell Non-Hodgkins Lymphoma", Clin Cancer Res (2013) 19: pp. 6820-6829.

Alfthan et al., "Properties of a single-chain antibody containing different linker peptides," Protein Engineering, vol. B, No. 7, pp. 725-731 (1995).

Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).

Bork et al., "Proposed acquisition of an animal protein domain by bacteria," Proceedings of the National Academy of Science, USA, vol. 89, pp. 8990-8994 (1992).

Hallewell et al., "Genetically Engineered Polymers of Human CuZN Superoxide Dismutase," The Journal of Biological Chemistry, vol. 264, No. 9, pp. 5260-5268 (1989).

Hanes et al, "In vitro selection and evolution of functional proteins by using ribosome display," Proceedings of the National Academy of Sciences USA, vol. 94, pp. 4937-4942 (1997).

Jacobs et al., "Design of novel FN3 domains with high stability by a consensus sequence approach," Protein Engineering, Design & Selection, vol. 25, No. 3, pp. 107-117 (2012).

Diem et al., "Selection of high-affinity Centyrin FN3 domains from a simply library diversified at a combination of strand and loop positions." Protein Engin Design (2014) Selection 27(10): 419-429.

Tannock and Hill. The Basic Science of Oncology. 1998. New York: McGraw-Hill;; pp. 357-358.

Song et al. Cancer stem cells—an old idea that's new again: implications for the diagnosis and treatment of breast cancer. Expert Opin Biol Ther 7:4):431-438, 2007.

Binz et al., "High-affinity binders selected from designed ankyrin repeat protein libraries," Nature Biotechnology, vol. e2, No. 5, pp. 575-582 (May 2004).

Garon et al., "Pembrolizumab for the Treatment of Non-Small-Cell Lung Cancer," The New England Journal of Medicine, vol. 372, No. 21, pp. 2018-2028 (May 21, 2015).

Koide et al., "High-affinity single-domain binding proteins with a binary-code interface," PNAS, vol. 104, No. 16, pp. 6632-6637(Apr. 17, 2017).

Lepenies et al., "The Role of Negative Costimulators Dunng Parasitic Infections," Endocrine, Metabolic & Immune Disorders—Drug Targets, vol. 8, pp. 279-288 (2008).

McLaughlin et al., "Quantitative Assessmenet of the Heterogeneity of PD-L 1 Expression in Non-small Cell Lung Cancer (NSCLC)," JAMA Oncol., vol. 2, No. 1, pp. 46-54, (Jan. 2016).

Meinke et al., "Cellulose-Binding Polypeptides from Cellulomonas fimi: Endoglucanase D (CenD), a Family A b-1,4-Glucanase," Journal of Bactenology, vol. 175, No. 7, pp. 1910-1918 (1993).

Odegrip et al., "CIS display: In vitro selection of peptides from libraries of protein-DNA complexes," Proceedings of the National Academy of Science USA, vol. 101, No. 9, pp. 2806-2810 (2004).

Olson et al., "Design, expression, and stability of a diverse protein library based on the human fibronectin type III ô €,?omain," Protein Science, vol. 16, pp. 476-484 (2007).

Roberts et al., "RNA-peptide fusions for the in vitro selection of peptides and proteins," Proceedings of the National Academy of Science USA, vol. 94, pp. 12297-12302 (1997).

Robinson et al., "Covalent Attachment of Arc Repressor Subunits by a Peptide Linker Enhances Affinity for Operator DNA," Biochemistry, vol. 35, pp. 109-116 (1996).

Strohl, William R., "Optimization of Fe-mediated effector functions of monoclonal antibodies," Current Opinion in Biotechnology, vol. 20, pp. 685-691 (2009).

Tie et al., "Safety and efficacy of nivolumab in the treatment of cancers: A meta-analysis of 27 prospective clinical rials," International Journal of Cancer, vol. 140, pp. 948-958, (2017).

Wang et al., "VISTA, a novel mouse lg superfamily ligand that negatively regulates T cell responses," Journal of Experimental Medicine, vol. 208, No. 3, pp. 577-592 (Mar. 14, 2011).

Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).

Cooper et al., "4-1 BB (CD 137) controls the clonal expansion and survival of COB T cells in vivo but does not t: ontribute the development of cytotoxicity", Eur. J_ Immunol., vol. 32, pp. 521-529, 2002.

Gramaglia et al., "Co-stimulation of antigen-specific CD4T cells by 4-1BB ligand," Eur. J. Immunol., vol. 30, p. ô €?"92-402 (2000).

DeBenedette et al., "Role of 4-1BB Ligand in Costimulation of T Lymphocyte Growth and its Upregulation on M12 B rymphomas by cAMP," J_ Exp_ Med., vol. 181, pp. 985-992 (1995).

Langstein et al., "CD137 Induces Proliferation and Endomitosis in Monocytes," Blood, vol. 94, No. 9, pp. 3161-3168 1999).

Langstein et al., "CD137 (ILA/4-1 BB), a Member of the TNF Receptor Family, Induces Monocyte Activation via Bidirectional Signaling," The Journal of Immunology, vol. 160, pp. 2488-2494 (1998).

Lee et al., "4-1 BB Promotes the Survival of COB+ T Lymphocytes by Increasing Expression of Bcl-xL and Bfl-11," The Journal of Immunol., vol. 169, pp. 4882-4888 (2002).

(56) References Cited

OTHER PUBLICATIONS

Michel et al., "A soluble form of CD 137 (ILA/4-1BB), a member of the TNF receptor family, is released by activated ymphocytes and is detectable in sera of patients with rheumatoid arthritis," Eur. J. Immunol., vol. 28, pp. 290-295 1998).

Michel et al., "CD137-induced apoptosis is independent of CD95," Immunology, vol. 98, pp. 42-46 (1999).

Schwarz et al., "ILA, a Member of the Human Nerve Growth FactorfTumor Necrosis Factor Receptor Family, Regulates T-Lymphocyte Proliferation and Survival," Blood, vol. 87, No. 7, pp. 2839-2845 (Apr. 1, 1996).

Shuford et al., "4-18B Costimulatory Signals Preferentially Induce COB+ T Cell Proliferation and Lead to the amplification In Vivo of Cytotoxic T Cell Responses," J. Exp. Med., vol. 186, No. 1, pp. 47-55 (Jul. 7, 1997).

Takahashi et al., "Cutting Edge: 4-1 BB is a Bona Fide COB T Cell Survival Signal," J Immunol., vol. 162, pp. 0037-5040 (1999).

Alderson et al., "Molecular and Biological Characterization of Human 4-1 BB and its Ligand", Eur. J. Immunol., vol. N, pp. 2219-2227, 1994.

Hurtado et al., "Potential role of 4-1 BB in T cell Activation Comparison with the Costimulatory Molecule CD28", Journal of Immunology, vol. 155, pp. 3360-3367, 1995.

Hurtado et al., "Signals through 4-1BB are Costimulatory to previously activated splenic T cells and inhibit activation-induced cell death", Journal of Immunology, vol. 158, pp. 2600-2609, 1997.

Maus et al., Ex vivo expansion of polyclonal and antigen-specific cytotoxic T lymphocytes by artificial APCs Expressing ligands for the T-cell receptor, CD28 and 4-1BB Nature Biotechnology, vol. 20, pp. 143-148, Feb. 2002.

Michel et al., "Expression of soluble CD137 correlates with activation-induced cell death of lymphocytes", Cytokine, vol. 12, No. 6, pp. 742-746, 2000.

Zhou et al., Characterization of human homologue of 4-1 BB and its ligand, Immunology Letters, vol. 45, pp. o7-73, 1995.

Pauly et al., CD137 is expressed by follicular dendritic cells and costimulates B lymphocyte activation in germinal t; enters, Journal of Leukocyte Biology, vol. 72, pp. 35-42, Jul. 2002.

Langstein et al., Identification of CD137 as a potent monocyte survival factor, Journal of Leukocyte Biology, vol. 65, pp. 829-833, Jun. 1999.

Kwon et al., cDNA sequences of two inducible T-cell genes, Proc. Natl. Acad. Sci., vol. 86, pp. 1963-1967, Mar. 1989.

Lehmann et al., Engineering proteins for thermostability the use of sequence alignments versus rational design and directed evolution, Current Opinion in Biotechnology, vol. 12, pp. 371-375 (2001).

Chiba et al., Amyloid Fibril Formation in the Context of Full-length Protein Effects of Praline mutations on the Amyloid fibril formation of b2-Microglobulin, Journal of Biological Chemistry, vol. 278, No. 47, pp. 47016-47024, Nov. 2003.

Goldberg et al., "Engineering a Targeted Delivery Platform using Centyrins" Protein Engineering, Design & selection, vol. 29, No. 12, pp. 563-572, 2016.

Strand et al., "Site-Specific Radioiodination of HER2-Targeting Affibody Molecules using 4-lodophenethylmaleimide Decreases Renal Uptake of Radioactivity"; Chemistry Open, vol. 4, pp. 174-182, 2015.

Hylarides et al., "Preparation and in Vivo Evaluation of an N-9p-[125I]1odophenethyl) maleimide—Antibody Conjugate" Bioconjugate Chem., vol. 2, pp. 435-440, 1991.

Lohse et al., Fluorescein-Conjugated Lysine monomers for Solid Phase Synthesis of Fluorescent Peptides and PNA Pligomers Bioconjugate Chem, vol. 8, pp. 503-509, 1997 .pdf.

Binz, et al., "Engineered proteins as specific binding reagents," Current Opinion in Biotechnology, 16:459-469 (2005).

UniProt Accession No. P10039, Nov. 1, 1997.

\* cited by examiner

CD137 BINDING FIBRONECTIN TYPE III DOMAINS

CROSS REFERENCE TO RELATED APPLICATIONS

This application claims the benefit of U.S. Provisional Application Ser. No. 62/434,064, filed 14 Dec. 2016. The entire contents of the aforementioned application are incorporated herein by reference in their entireties.

FIELD OF THE INVENTION

The present invention relates to fibronectin type III domains that specifically bind to cluster of differentiation 137 (CD137) and methods of making and using the molecules.

BACKGROUND OF THE INVENTION

Advances in understanding of the requirements for tumor antigen recognition and immune effector function indicate that a potential strategy to enhance an anti-tumor immune response is to provide co-stimulation through an auxiliary molecule. The current model for T-cell activation postulates that naive T-cells require two signals for full activation: (i) a signal provided through the binding of processed antigens presented to the T-cell receptor by major histocompatibility complex (MHC) class I molecules; and (ii) an additional signal provided by the interaction of co-stimulatory molecules on the surface of T-cells and their ligands on antigen presenting cells.

CD137 (4-1BB) is a member of the TNF receptor superfamily and is an activation-induced T-cell costimulatory molecule. The receptor was initially described in mice (B. Kwon et al., *P.N.A.S.* USA, 86:1963-7 (1989)), and later identified in humans (M. Alderson et al., *Eur. J. Immunol.*, 24: 2219-27 (1994); Z. Zhou et al., *Immunol. Lett.*, 45:67 (1995)). The interaction of CD137 and the CD137 ligand (4-1BBL) activates an important costimulatory pathway. Signaling via CD137 upregulates survival genes, enhances cell division, induces cytokine production, and prevents activation-induced cell death in T cells. The importance of the CD137 pathway has been underscored in a number of diseases, including cancer (see, e.g., U.S. Pat. No. 7,288,638).

Expression of CD137 has been shown to be predominantly on cells of lymphoid lineage such as activated T-cells, activated Natural Killer (NK) cells, NKT-cells, CD4CD25 regulatory T-cells, and also on activated thymocytes, and intraepithelial lymphocytes. In addition, CD137 has also been shown to be expressed on cells of myeloid origin like dendritic cells, monocytes, neutrophils, and eosinophils. Even though CD137 expression is mainly restricted to immune/inflammatory cells, there have been reports describing its expression on endothelial cells associated with a small number of tissues from inflammatory sites and tumors.

The physiological events observed following CD137 stimulation on T-cells are mediated by NF-κB and PI3K/ERK1/2 signals with separate physiological functions. NF-κB signals trigger expression of Bcl-XL, an anti-apoptotic molecule, thus resulting in increased survival, whereas PI3K and ERK1/2 signals are specifically responsible for CD137-mediated cell cycle progression (H. Lee et al., *J. Immunol.*, 169(9):4882-8 (2002)). The effect of CD137 activation on the inhibition of activation-induced cell death was shown in vitro by Hurtado et al. (J. Hurtado et al., *J. Immunol.*, 158(6):2600-9 (1997)), and in an in vivo system in which anti-CD137 monoclonal antibodies (mabs) were shown to produce long-term survival of superantigen-activated CD8+ T-cells by preventing clonal deletion (C. Takahashi et al., *J. Immunol.*, 162:5037 (1999)). Later, two reports demonstrated, under different experimental conditions, that the CD137 signal regulated both clonal expansion and survival of CD8+ T-cells (D. Cooper et al., *Eur. J. Immunol.*, 32(2):521-9 (2002); M. Maus et al., *Nat. Biotechnol.*, 20:143 (2002)).

Altogether, CD137 stimulation results in enhanced expansion, survival, and effector functions of newly primed CD8+ T-cells, acting, in part, directly on these cells. Both CD4+ and CD8+ T-cells have been shown to respond to CD137 stimulation, however, it appears that enhancement of T-cell function is greater in CD8+ cells ((W. Shuford et al., *J. Exp. Med.*, 186(1):47-55 (1997); I. Gramaglia et al., *Eur. J. Immunol.*, 30(2):392-402 (2000); C. Takahashi et al., *J. Immunol.*, 162:5037 (1999)). Based on the critical role of CD137 stimulation in CD8+ T-cell function and survival, agonism of the CD137/CD137L system provides a plausible approach for the treatment of tumors and viral pathogens.

Alternatively, while it has been shown that agonistic antibodies to CD137 and the ligand to CD137 enhance lymphocyte activation, the CD137 protein has the opposite effect. It inhibits proliferation of activated T lymphocytes and induces programmed cell death. These T cell-inhibitory activities of CD137 require immobilisation of the protein, arguing for transmission of a signal through the ligand/coreceptor (Schwarz et al., *Blood* 87, 2839-2845 (1996); Michel et al., *Immunology* 98, 42-46 (1999)).

The known human CD137 ligand is expressed constitutively by monocytes and its expression is inducible in T lymphocytes (Alderson et al., *Eur. J. Immunol.* 24, 2219-2227 (1994)). Monocytes are activated by immobilised CD137 protein and their survival is profoundly prolonged by CD137. (Langstein et al., *J. Immunol.* 160, 2488-2494 (1998); Langstein et al., *J. Leuk. Biol.* 65, 829-833 (1999)). CD137 also induces proliferation in peripheral monocytes (Langstein et al., 1999b). Macrophage colony-stimulating factor (M-CSF) is essential for the proliferative and survival-enhancing activities of CD137 (Langstein et al., *J. Leuk. Biol.* 65, 829-833 (1999); Langstein et al., *Blood* 94, 3161-3168 (1999)).

Signalling through CD137 ligand has also been demonstrated in B cells where it enhances proliferation and immunoglobulin synthesis. This occurs at interactions of B cells with CD137-expressing T cells or follicular dendritic cells (Pauly et al., *J. Leuk. Biol.* 72, 35-42 (2002)). It was postulated that similarly to the CD40 receptor/ligand system, which mediates T cell help to B cells after first antigen encounter, the CD137 receptor/ligand system may mediate co-stimulation of B cells by FDC during affinity maturation (Pauly et al., *J. Leuk. Biol.* 72, 35-42 (2002)).

Furthermore, soluble forms of CD137 are generated by differential splicing and are selectively expressed by activated T cells (Michel et al., *Eur. J. Immunol.* 28, 290-295 (1998)). Soluble CD137 is antagonistic to membrane-bound or immobilised CD137, and levels of soluble CD137 correlate with activation induced cell death in T cells (DeBenedette et al., *J. Exp. Med.* 181, 985-992 (1995); Hurtado et al., *J. Immunol.* 155, 3360-3367 (1995); Michel et al., *Cytokine* 12, 742-746 (2000)).

Thus, considering the complicated picture for CD137 involvement in divergent mechanisms of action and different cell types, there exists a need for reagents to accurately detect CD137 in tumor tissues and other samples and for new therapeutics that modulate the interaction between CD137 and the 4-1BBL ligand or that modulate the interaction between CD137 and other cellular targets.

SUMMARY OF THE INVENTION

The invention provides an isolated FN3 domain that specifically binds to CD137 protein.

The invention also provides an isolated FN3 domain that specifically binds to CD137 protein comprising the amino acid sequence of SEQ ID NOs: 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, or 224.

The invention also provides an isolated polynucleotide encoding the FN3 domain that specifically binds to CD137 protein.

The invention also provides a vector comprising the polynucleotide.

The invention also provides a host cell comprising the vector.

The invention also provides a method of producing the FN3 domain that specifically binds to CD137 protein, comprising culturing the isolated host cell under conditions that the FN3 domain that specifically binds to CD137 protein is expressed, and purifying the FN3 domain that specifically binds to CD137 protein.

The invention also provides a pharmaceutical composition comprising the FN3 domain that specifically binds to CD137 protein and a pharmaceutically acceptable carrier.

The invention also provides an anti-idiotypic antibody that specifically binds the FN3 domain that specifically binds to CD137 protein.

The invention also provides a kit comprising the FN3 domain.

The invention also provides a method of detecting CD137-expressing cancer cells in a tumor tissue, comprising
obtaining a sample of the tumor tissue from a subject; and
detecting whether CD137 protein is expressed in the tumor tissue by contacting
the sample of the tumor tissue with the FN3 domain that specifically binds CD137 protein comprising the amino acid sequence of one of SEQ ID NOs: 45-224 and detecting the binding between CD137 protein and the FN3 domain.

The invention also provides a method of isolating CD137 expressing cells, comprising obtaining a sample from a subject;
contacting the sample with the FN3 domain that specifically binds to CD137 protein comprising the amino acid sequence of one of SEQ ID NOs: 45-224, and isolating the cells bound to the FN3 domains.

The invention also provides a method of detecting CD137-expressing cancer cells in a tumor tissue, comprising conjugating the FN3 domain that specifically binds to CD137 protein comprising the amino acid sequence of one of SEQ ID NOs: 45-224 to a detectable label to form a conjugate;
administering the conjugate to a subject; and
visualizing the CD137 expressing cancer cells to which the conjugate is bound.

DETAILED DESCRIPTION OF THE INVENTION

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the 3rd FN3 domain of tenascin (TN3), or the $10^{th}$ FN3 domain of fibronectin (FN10).

"Centyrin" refers to a FN3 domain that is based on the consensus sequence of the 15 different FN3 domains present in human tenascin C.

The term "capture agent" refers to substances that bind to a particular type of cells and enable the isolation of that cell from other cells. Exemplary capture agents are magnetic beads, ferrofluids, encapsulating reagents, molecules that bind the particular cell type and the like.

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Substituting" or "substituted" or "mutating" or "mutated" refers to altering, deleting of inserting one or more amino acids or nucleotides in a polypeptide or polynucleotide sequence to generate a variant of that sequence.

"Variant" refers to a polypeptide or a polynucleotide that differs from a reference polypeptide or a reference polynucleotide by one or more modifications for example, substitutions, insertions or deletions.

"Specifically binds" or "specific binding" refers to the ability of the FN3 domain of the invention to bind CD137 with a dissociation constant ($K_D$) of about $1\times10^{-6}$ M or less, for example about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. Alternatively, "specific binding" refers to the ability of the FN3 domain of the invention to bind CD137 at least 5-fold above the negative control in standard ELISA assay. The isolated FN3 domain of the invention that specifically binds CD137 may, however, have cross-reactivity to other related antigens, for example to the same predetermined antigen from other species (homologs), such as *Macaca Fascicularis* (cynomolgous monkey, cyno) or Pan troglodytes (chimpanzee).

"Library" refers to a collection of variants. The library may be composed of polypeptide or polynucleotide variants.

"Stability" refers to the ability of a molecule to maintain a folded state under physiological conditions such that it retains at least one of its normal functional activities, for example, binding to a predetermined antigen such as CD137.

"CD137" refers to human CD137 protein having the amino acid sequence of SEQ ID NO:44.

"Tencon" refers to the synthetic fibronectin type III (FN3) domain having the sequence shown in SEQ ID NO:1 and described in U.S. Pat. Publ. No. 2010/0216708.

A "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than about 50 amino acids may be referred to as "peptides".

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

Compositions of Matter

The present invention provides fibronectin type III (FN3) domains that specifically bind human CD137 protein (SEQ ID NO:44). These molecules can be used in therapeutic and diagnostic applications and in imaging. The present invention provides polynucleotides encoding the FN3 domains of the invention or complementary nucleic acids thereof, vectors, host cells, and methods of making and using them.

The invention provides an isolated FN3 domain that specifically binds CD137.

The FN3 domain of the invention may bind CD137 with a dissociation constant ($K_D$) of less than about $1 \times 10^{-7}$ M, for example less than about $1 \times 10^{-8}$ M, less than about $1 \times 10^{-9}$ M, less than about $1 \times 10^{-10}$ M, less than about $1 \times 10^{-11}$ M, less than about $1 \times 10^{-12}$ M, or less than about $1 \times 10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffer described herein.

The FN3 domain of the invention may bind CD137 at least 5-fold above the signal obtained for a negative control in standard ELISA assay.

In some embodiments, the FN3 domain that specifically binds CD137 comprises an initiator methionine (Met) linked to the N-terminus of the molecule.

In some embodiments, the FN3 domain that specifically binds CD137 comprises a cysteine (Cys) linked to a C-terminus of the FN3 domain.

The addition of the N-terminal Met and/or the C-terminal Cys may facilitate expression and/or conjugation of half-life extending molecules.

In some embodiments, the FN3 domain that specifically binds CD137 is internalized into a cell.

Internalization of the FN3 domain may facilitate delivery of a cytotoxic agent into tumor cells.

In some embodiments, the FN3 domain that specifically binds CD137 inhibits binding of the CD137 ligand (4-1BBL) to CD137.

Inhibition of binding of 4-1BBL to CD137 by the FN3 domains of the invention may be assessed using competition ELISA. In an exemplary assay, 1 µg/ml recombinant human CD137 is bound on wells of microtiter plates, the wells are washed and blocked, and 10 µg/ml of the test FN3 domain is added. Without washing, 7.5 µg/ml 4-1BBL is added into the wells and incubated for 30 min, after which 0.5 µg/ml anti-4-1BBL antibodies are added and incubated for 30 min. The plates are washed and 0.5 µg/mL neutravidin-HRP conjugate polyclonal antibody is added and incubated for 30 minutes. The plates are washed and POD Chemiluminescence substrate added immediately prior to reading the luminescence signal. The FN3 domains of the invention inhibit binding of 4-1BBL to CD137 when the binding of 4-1BBL is reduced by at least about 80%, 85%, 90%, 95% or 100%.

In some embodiments, the FN3 domain that specifically binds CD137 is a CD137 antagonist.

In some embodiments, the FN3 domain that specifically binds CD137 is a CD137 agonist.

"Antagonist" refers to a FN3 domain that specifically binds CD137 that suppresses at least one activity of CD137 function by inhibiting CD137 binding to to its natural ligand 4-1BB1 or inhibiting CD137 binding to other molecules. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. A typical reaction or activity that is induced by 4-1BBL binding to CD137 is upregulation of survival genes, enhanced cell division, induced cytokine production, and prevention of activation-induced cell death in T cells.

The antagonistic FN3 domains that specifically bind CD137 may be used in the treatment of autoimmune or inflammatory diseases and in general diseases in which suppression of T cell responses is desirable.

"Agonist" refers to a FN3 domain that specifically binds CD137 that induces at least one reaction or activity that is induced by CD137. The FN3 domain is an agonist when the at least one reaction or activity is induced by at least about 30%, 40%, 45%, 50%, 55%, 60%, 65%, 70%, 75%, 80%, 85%, 90%, 95%, or 100% greater than the at least one reaction or activity induced in the absence of the agonist (e.g., negative control), or when the induction is statistically significant when compared to the induction in the absence of the agonist. A typical reaction or activity that is induced by 4-1BBL binding to CD137 is upregulation of survival genes, enhanced cell division, induced cytokine production, and prevention of activation-induced cell death in T cells.

The agonistic FN3 domains that specifically bind CD137 may be used, for example, in the treatment of cancer or viral infections and in general in treatment of diseases in which activation of T cell responses is desirable.

In some embodiments, the FN3 domain that specifically binds CD137 does not inhibit 4-1BBL binding to CD137.

In some embodiments, the FN3 domain that specifically binds CD137 is based on Tencon sequence of SEQ ID NO:1 or Tencon 27 sequence of SEQ ID NO:4, optionally having substitutions at residues positions 11, 14, 17, 37, 46, 73, or 86 (residue numbering corresponding to SEQ ID NO:4).

The invention also provides an isolated FN3 domain that specifically binds CD137 comprising the amino acid sequence of SEQ ID NOs: 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, or 224.

The invention also provides an isolated FN3 domain that specifically binds CD137 comprising the amino acid sequence of SEQ ID NO:45.

The invention also provides an isolated FN3 domain that specifically binds CD137 comprising the amino acid sequence of SEQ ID NO:46.

The invention also provides an isolated FN3 domain that specifically binds CD137 comprising the amino acid sequence of SEQ ID NO:47.

The invention also provides an isolated FN3 domain that specifically binds CD137 comprising the amino acid sequence of SEQ ID NO:48.

The invention also provides an isolated FN3 domain that specifically binds CD137 comprising the amino acid sequence of SEQ ID NO:49.

The invention also provides an isolated FN3 domain that specifically binds CD137 comprising the amino acid sequence of SEQ ID NO:50.

The invention also provides an isolated FN3 domain that specifically binds CD137 comprising the amino acid sequence of SEQ ID NO:51.

The invention also provides an isolated FN3 domain that specifically binds CD137 comprising the amino acid sequence of SEQ ID NO:52.

The invention also provides an isolated FN3 domain that specifically binds CD137 comprising the amino acid sequence of SEQ ID NO:53.

CD137 comprising the amino acid sequence of SEQ ID NO:54.

The invention also provides an isolated FN3 domain that specifically binds CD137 comprising the amino acid sequence of SEQ ID NO:55.

The invention also provides an isolated FN3 domain that specifically binds CD137 comprising the amino acid sequence of SEQ ID NO:56.

The invention also provides an isolated FN3 domain that specifically binds CD137 comprising the amino acid sequence of SEQ ID NO:57.

The invention also provides an isolated FN3 domain that specifically binds CD137 comprising the amino acid sequence of SEQ ID NO:58.

The invention also provides an isolated FN3 domain that specifically binds CD137 comprising the amino acid sequence of SEQ ID NO:59.

The invention also provides an isolated FN3 domain that specifically binds CD137 comprising the amino acid sequence of SEQ ID NO:60.

The invention also provides an isolated FN3 domain that specifically binds CD137 comprising the amino acid sequence of SEQ ID NO:61.

The invention also provides an isolated FN3 domain that specifically binds CD137 comprising the amino acid sequence of SEQ ID NO:62.

The invention also provides an isolated FN3 domain that specifically binds CD137 comprising the amino acid sequence of SEQ ID NO:63.

The invention also provides an isolated FN3 domain that specifically binds CD137 comprising the amino acid sequence of SEQ ID NO:64.

The invention also provides an isolated FN3 domain that specifically binds CD137 comprising the amino acid sequence of SEQ ID NO:65.

The invention also provides an isolated FN3 domain that specifically binds CD137 comprising the amino acid sequence of SEQ ID NO:66.

The invention also provides an isolated FN3 domain that specifically binds CD137 comprising the amino acid sequence of SEQ ID NO:67.

CD137 comprising the amino acid sequence of SEQ ID NO:68.

The invention also provides an isolated FN3 domain that specifically binds CD137 comprising the amino acid sequence of SEQ ID NO:69.

The invention also provides an isolated FN3 domain that specifically binds CD137 comprising the amino acid sequence of SEQ ID NO:70.

The invention also provides an isolated FN3 domain that specifically binds CD137 comprising the amino acid sequence of SEQ ID NO:71.

The invention also provides an isolated FN3 domain that specifically binds CD137 comprising the amino acid sequence of SEQ ID NO:72.

The invention also provides an isolated FN3 domain that specifically binds CD137 comprising the amino acid sequence of SEQ ID NO:73.

The invention also provides an isolated FN3 domain that specifically binds CD137 comprising the amino acid sequence of SEQ ID NO:74.

The invention also provides an isolated FN3 domain that specifically binds CD137 comprising the amino acid sequence of SEQ ID NO:75.

The invention also provides an isolated FN3 domain that specifically binds CD137 comprising the amino acid sequence of SEQ ID NO:76.

The invention also provides an isolated FN3 domain that specifically binds CD137 comprising the amino acid sequence of SEQ ID NO:77.

The invention also provides an isolated FN3 domain that specifically binds CD137 comprising the amino acid sequence of SEQ ID NO:78.

The invention also provides an isolated FN3 domain that specifically binds CD137 comprising the amino acid sequence of SEQ ID NO:79.

The invention also provides an isolated FN3 domain that specifically binds CD137 comprising the amino acid sequence of SEQ ID NO:80.

The invention also provides an isolated FN3 domain that specifically binds CD137 comprising the amino acid sequence of SEQ ID NO:81.

CD137 comprising the amino acid sequence of SEQ ID NO:82.

The invention also provides an isolated FN3 domain that specifically binds CD137 comprising the amino acid sequence of SEQ ID NO:83.

The invention also provides an isolated FN3 domain that specifically binds CD137 comprising the amino acid sequence of SEQ ID NO:84.

The invention also provides an isolated FN3 domain that specifically binds CD137 comprising the amino acid sequence of SEQ ID NO:85.

The invention also provides an isolated FN3 domain that specifically binds CD137 comprising the amino acid sequence of SEQ ID NO:86.

The invention also provides an isolated FN3 domain that specifically binds CD137 comprising the amino acid sequence of SEQ ID NO:87.

The invention also provides an isolated FN3 domain that specifically binds CD137 comprising the amino acid sequence of SEQ ID NO:88.

The invention also provides an isolated FN3 domain that specifically binds CD137 comprising the amino acid sequence of SEQ ID NO:89.

The invention also provides an isolated FN3 domain that specifically binds CD137 comprising the amino acid sequence of SEQ ID NO:90.

The invention also provides an isolated FN3 domain that specifically binds CD137 comprising the amino acid sequence of SEQ ID NO:91.

The invention also provides an isolated FN3 domain that specifically binds CD137 comprising the amino acid sequence of SEQ ID NO:92.

The invention also provides an isolated FN3 domain that specifically binds CD137 comprising the amino acid sequence of SEQ ID NO:93.

The invention also provides an isolated FN3 domain that specifically binds CD137 comprising the amino acid sequence of SEQ ID NO:94.

The invention also provides an isolated FN3 domain that specifically binds CD137 comprising the amino acid sequence of SEQ ID NO:95.

CD137 comprising the amino acid sequence of SEQ ID NO:96.

The invention also provides an isolated FN3 domain that specifically binds CD137 comprising the amino acid sequence of SEQ ID NO:97.

The invention also provides an isolated FN3 domain that specifically binds CD137 comprising the amino acid sequence of SEQ ID NO:98.

The invention also provides an isolated FN3 domain that specifically binds CD137 comprising the amino acid sequence of SEQ ID NO:99.

The invention also provides an isolated FN3 domain that specifically binds CD137 comprising the amino acid sequence of SEQ ID NO:100.

The invention also provides an isolated FN3 domain that specifically binds CD137 comprising the amino acid sequence of SEQ ID NO:101.

The invention also provides an isolated FN3 domain that specifically binds CD137 comprising the amino acid sequence of SEQ ID NO:102.

The invention also provides an isolated FN3 domain that specifically binds CD137 comprising the amino acid sequence of SEQ ID NO:103.

The invention also provides an isolated FN3 domain that specifically binds CD137 comprising the amino acid sequence of SEQ ID NO:104.

The invention also provides an isolated FN3 domain that specifically binds CD137 comprising the amino acid sequence of SEQ ID NO:105.

The invention also provides an isolated FN3 domain that specifically binds CD137 comprising the amino acid sequence of SEQ ID NO:106.

The invention also provides an isolated FN3 domain that specifically binds CD137 comprising the amino acid sequence of SEQ ID NO:107.

The invention also provides an isolated FN3 domain that specifically binds CD137 comprising the amino acid sequence of SEQ ID NO:108.

The invention also provides an isolated FN3 domain that specifically binds CD137 comprising the amino acid sequence of SEQ ID NO:109.

CD137 comprising the amino acid sequence of SEQ ID NO:110.

The invention also provides an isolated FN3 domain that specifically binds CD137 comprising the amino acid sequence of SEQ ID NO:111.

The invention also provides an isolated FN3 domain that specifically binds CD137 comprising the amino acid sequence of SEQ ID NO:112.

The invention also provides an isolated FN3 domain that specifically binds CD137 comprising the amino acid sequence of SEQ ID NO:113.

The invention also provides an isolated FN3 domain that specifically binds CD137 comprising the amino acid sequence of SEQ ID NO:114.

The invention also provides an isolated FN3 domain that specifically binds CD137 comprising the amino acid sequence of SEQ ID NO:115.

The invention also provides an isolated FN3 domain that specifically binds CD137 comprising the amino acid sequence of SEQ ID NO:116.

The invention also provides an isolated FN3 domain that specifically binds CD137 comprising the amino acid sequence of SEQ ID NO:117.

The invention also provides an isolated FN3 domain that specifically binds CD137 comprising the amino acid sequence of SEQ ID NO:118.

The invention also provides an isolated FN3 domain that specifically binds CD137 comprising the amino acid sequence of SEQ ID NO:119.

The invention also provides an isolated FN3 domain that specifically binds CD137 comprising the amino acid sequence of SEQ ID NO:120.

The invention also provides an isolated FN3 domain that specifically binds CD137 comprising the amino acid sequence of SEQ ID NO:121.

The invention also provides an isolated FN3 domain that specifically binds CD137 comprising the amino acid sequence of SEQ ID NO:122.

The invention also provides an isolated FN3 domain that specifically binds CD137 comprising the amino acid sequence of SEQ ID NO:123.

CD137 comprising the amino acid sequence of SEQ ID NO:124.

The invention also provides an isolated FN3 domain that specifically binds CD137 comprising the amino acid sequence of SEQ ID NO:125.

The invention also provides an isolated FN3 domain that specifically binds CD137 comprising the amino acid sequence of SEQ ID NO:126.

The invention also provides an isolated FN3 domain that specifically binds CD137 comprising the amino acid sequence of SEQ ID NO:127.

The invention also provides an isolated FN3 domain that specifically binds CD137 comprising the amino acid sequence of SEQ ID NO:128.

The invention also provides an isolated FN3 domain that specifically binds CD137 comprising the amino acid sequence of SEQ ID NO:129.

The invention also provides an isolated FN3 domain that specifically binds CD137 comprising the amino acid sequence of SEQ ID NO:130.

The invention also provides an isolated FN3 domain that specifically binds CD137 comprising the amino acid sequence of SEQ ID NO:131.

The invention also provides an isolated FN3 domain that specifically binds CD137 comprising the amino acid sequence of SEQ ID NO:132.

The invention also provides an isolated FN3 domain that specifically binds CD137 comprising the amino acid sequence of SEQ ID NO:133.

The invention also provides an isolated FN3 domain that specifically binds CD137 comprising the amino acid sequence of SEQ ID NO:134.

The invention also provides an isolated FN3 domain that specifically binds CD137 comprising the amino acid sequence of SEQ ID NO:135.

The invention also provides an isolated FN3 domain that specifically binds CD137 comprising the amino acid sequence of SEQ ID NO:136.

The invention also provides an isolated FN3 domain that specifically binds CD137 comprising the amino acid sequence of SEQ ID NO:137.

CD137 comprising the amino acid sequence of SEQ ID NO:138.

The invention also provides an isolated FN3 domain that specifically binds CD137 comprising the amino acid sequence of SEQ ID NO:139.

The invention also provides an isolated FN3 domain that specifically binds CD137 comprising the amino acid sequence of SEQ ID NO:140.

The invention also provides an isolated FN3 domain that specifically binds CD137 comprising the amino acid sequence of SEQ ID NO:141.

The invention also provides an isolated FN3 domain that specifically binds CD137 comprising the amino acid sequence of SEQ ID NO:142.

The invention also provides an isolated FN3 domain that specifically binds CD137 comprising the amino acid sequence of SEQ ID NO:143.

The invention also provides an isolated FN3 domain that specifically binds CD137 comprising the amino acid sequence of SEQ ID NO:144.

The invention also provides an isolated FN3 domain that specifically binds CD137 comprising the amino acid sequence of SEQ ID NO:145.

The invention also provides an isolated FN3 domain that specifically binds CD137 comprising the amino acid sequence of SEQ ID NO:146.

The invention also provides an isolated FN3 domain that specifically binds CD137 comprising the amino acid sequence of SEQ ID NO:147.

The invention also provides an isolated FN3 domain that specifically binds CD137 comprising the amino acid sequence of SEQ ID NO:148.

The invention also provides an isolated FN3 domain that specifically binds CD137 comprising the amino acid sequence of SEQ ID NO:149.

The invention also provides an isolated FN3 domain that specifically binds CD137 comprising the amino acid sequence of SEQ ID NO:150.

The invention also provides an isolated FN3 domain that specifically binds CD137 comprising the amino acid sequence of SEQ ID NO:151.

CD137 comprising the amino acid sequence of SEQ ID NO:152.

The invention also provides an isolated FN3 domain that specifically binds CD137 comprising the amino acid sequence of SEQ ID NO:153.

The invention also provides an isolated FN3 domain that specifically binds CD137 comprising the amino acid sequence of SEQ ID NO:154.

The invention also provides an isolated FN3 domain that specifically binds CD137 comprising the amino acid sequence of SEQ ID NO:155.

The invention also provides an isolated FN3 domain that specifically binds CD137 comprising the amino acid sequence of SEQ ID NO:156.

The invention also provides an isolated FN3 domain that specifically binds CD137 comprising the amino acid sequence of SEQ ID NO:157.

The invention also provides an isolated FN3 domain that specifically binds CD137 comprising the amino acid sequence of SEQ ID NO:158.

The invention also provides an isolated FN3 domain that specifically binds CD137 comprising the amino acid sequence of SEQ ID NO:159.

The invention also provides an isolated FN3 domain that specifically binds CD137 comprising the amino acid sequence of SEQ ID NO:160.

The invention also provides an isolated FN3 domain that specifically binds CD137 comprising the amino acid sequence of SEQ ID NO:161.

The invention also provides an isolated FN3 domain that specifically binds CD137 comprising the amino acid sequence of SEQ ID NO:162.

The invention also provides an isolated FN3 domain that specifically binds CD137 comprising the amino acid sequence of SEQ ID NO:163.

The invention also provides an isolated FN3 domain that specifically binds CD137 comprising the amino acid sequence of SEQ ID NO:164.

The invention also provides an isolated FN3 domain that specifically binds CD137 comprising the amino acid sequence of SEQ ID NO:165.

CD137 comprising the amino acid sequence of SEQ ID NO:166.

The invention also provides an isolated FN3 domain that specifically binds CD137 comprising the amino acid sequence of SEQ ID NO:167.

The invention also provides an isolated FN3 domain that specifically binds CD137 comprising the amino acid sequence of SEQ ID NO:168.

The invention also provides an isolated FN3 domain that specifically binds CD137 comprising the amino acid sequence of SEQ ID NO:169.

The invention also provides an isolated FN3 domain that specifically binds CD137 comprising the amino acid sequence of SEQ ID NO:170.

The invention also provides an isolated FN3 domain that specifically binds CD137 comprising the amino acid sequence of SEQ ID NO:171.

The invention also provides an isolated FN3 domain that specifically binds CD137 comprising the amino acid sequence of SEQ ID NO:172.

The invention also provides an isolated FN3 domain that specifically binds CD137 comprising the amino acid sequence of SEQ ID NO:173.

The invention also provides an isolated FN3 domain that specifically binds CD137 comprising the amino acid sequence of SEQ ID NO:174.

The invention also provides an isolated FN3 domain that specifically binds CD137 comprising the amino acid sequence of SEQ ID NO:175.

The invention also provides an isolated FN3 domain that specifically binds CD137 comprising the amino acid sequence of SEQ ID NO:176.

The invention also provides an isolated FN3 domain that specifically binds CD137 comprising the amino acid sequence of SEQ ID NO:177.

The invention also provides an isolated FN3 domain that specifically binds CD137 comprising the amino acid sequence of SEQ ID NO:178.

The invention also provides an isolated FN3 domain that specifically binds CD137 comprising the amino acid sequence of SEQ ID NO:179.

CD137 comprising the amino acid sequence of SEQ ID NO:180.

The invention also provides an isolated FN3 domain that specifically binds CD137 comprising the amino acid sequence of SEQ ID NO:181.

The invention also provides an isolated FN3 domain that specifically binds CD137 comprising the amino acid sequence of SEQ ID NO:182.

The invention also provides an isolated FN3 domain that specifically binds CD137 comprising the amino acid sequence of SEQ ID NO:183.

The invention also provides an isolated FN3 domain that specifically binds CD137 comprising the amino acid sequence of SEQ ID NO:184.

The invention also provides an isolated FN3 domain that specifically binds CD137 comprising the amino acid sequence of SEQ ID NO:185.

The invention also provides an isolated FN3 domain that specifically binds CD137 comprising the amino acid sequence of SEQ ID NO:186.

The invention also provides an isolated FN3 domain that specifically binds CD137 comprising the amino acid sequence of SEQ ID NO:187.

The invention also provides an isolated FN3 domain that specifically binds CD137 comprising the amino acid sequence of SEQ ID NO:188.

The invention also provides an isolated FN3 domain that specifically binds CD137 comprising the amino acid sequence of SEQ ID NO:189.

The invention also provides an isolated FN3 domain that specifically binds CD137 comprising the amino acid sequence of SEQ ID NO:190.

The invention also provides an isolated FN3 domain that specifically binds CD137 comprising the amino acid sequence of SEQ ID NO:191.

The invention also provides an isolated FN3 domain that specifically binds CD137 comprising the amino acid sequence of SEQ ID NO:192.

The invention also provides an isolated FN3 domain that specifically binds CD137 comprising the amino acid sequence of SEQ ID NO:193.

CD137 comprising the amino acid sequence of SEQ ID NO:194.

The invention also provides an isolated FN3 domain that specifically binds CD137 comprising the amino acid sequence of SEQ ID NO:195.

The invention also provides an isolated FN3 domain that specifically binds CD137 comprising the amino acid sequence of SEQ ID NO:196.

The invention also provides an isolated FN3 domain that specifically binds CD137 comprising the amino acid sequence of SEQ ID NO:197.

The invention also provides an isolated FN3 domain that specifically binds CD137 comprising the amino acid sequence of SEQ ID NO:198.

The invention also provides an isolated FN3 domain that specifically binds CD137 comprising the amino acid sequence of SEQ ID NO:199.

The invention also provides an isolated FN3 domain that specifically binds CD137 comprising the amino acid sequence of SEQ ID NO:200.

The invention also provides an isolated FN3 domain that specifically binds CD137 comprising the amino acid sequence of SEQ ID NO:201.

The invention also provides an isolated FN3 domain that specifically binds CD137 comprising the amino acid sequence of SEQ ID NO:202.

The invention also provides an isolated FN3 domain that specifically binds CD137 comprising the amino acid sequence of SEQ ID NO:203.

The invention also provides an isolated FN3 domain that specifically binds CD137 comprising the amino acid sequence of SEQ ID NO:204.

The invention also provides an isolated FN3 domain that specifically binds CD137 comprising the amino acid sequence of SEQ ID NO:205.

The invention also provides an isolated FN3 domain that specifically binds CD137 comprising the amino acid sequence of SEQ ID NO:206.

The invention also provides an isolated FN3 domain that specifically binds CD137 comprising the amino acid sequence of SEQ ID NO:207.

CD137 comprising the amino acid sequence of SEQ ID NO:208.

The invention also provides an isolated FN3 domain that specifically binds CD137 comprising the amino acid sequence of SEQ ID NO:209.

The invention also provides an isolated FN3 domain that specifically binds CD137 comprising the amino acid sequence of SEQ ID NO:210.

The invention also provides an isolated FN3 domain that specifically binds CD137 comprising the amino acid sequence of SEQ ID NO:211.

The invention also provides an isolated FN3 domain that specifically binds CD137 comprising the amino acid sequence of SEQ ID NO:212.

The invention also provides an isolated FN3 domain that specifically binds CD137 comprising the amino acid sequence of SEQ ID NO:213.

The invention also provides an isolated FN3 domain that specifically binds CD137 comprising the amino acid sequence of SEQ ID NO:214.

The invention also provides an isolated FN3 domain that specifically binds CD137 comprising the amino acid sequence of SEQ ID NO:215.

The invention also provides an isolated FN3 domain that specifically binds CD137 comprising the amino acid sequence of SEQ ID NO:216.

The invention also provides an isolated FN3 domain that specifically binds CD137 comprising the amino acid sequence of SEQ ID NO:217.

The invention also provides an isolated FN3 domain that specifically binds CD137 comprising the amino acid sequence of SEQ ID NO:218.

The invention also provides an isolated FN3 domain that specifically binds CD137 comprising the amino acid sequence of SEQ ID NO:219.

The invention also provides an isolated FN3 domain that specifically binds CD137 comprising the amino acid sequence of SEQ ID NO:220.

The invention also provides an isolated FN3 domain that specifically binds CD137 comprising the amino acid sequence of SEQ ID NO:221.

CD137 comprising the amino acid sequence of SEQ ID NO:222.

The invention also provides an isolated FN3 domain that specifically binds CD137 comprising the amino acid sequence of SEQ ID NO:223.

The invention also provides an isolated FN3 domain that specifically binds CD137 comprising the amino acid sequence of SEQ ID NO:224.

In some embodiments, the isolated FN3 domain that specifically binds CD137 comprises an initiator methionine (Met) linked to the N-terminus of the molecule.

In some embodiments, the isolated FN3 domain that specifically binds CD137 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 45-224.

Conjugates of the FN3 Domains that Specifically Bind CD137 of the Invention

The invention also provides an isolated FN3 domain that specifically binds CD137 conjugated to a heterologous molecule(s).

In some embodiments, the heterologous molecule is a detectable label or a cytotoxic agent.

The invention also provides an FN3 domain that specifically binds CD137 conjugated to a detectable label.

The invention also provides an FN3 domain that specifically binds CD137 conjugated to a cytotoxic agent.

In some embodiments, the detectable label is also a cytotoxic agent.

The FN3 domains that specifically bind CD137 of the invention conjugated to a detectable label can be used to evaluate expression of CD137 on samples such as tumor tissue in vivo or in vitro.

Detectable label includes compositions that when conjugated to the FN3 domains that specifically bind CD137 of the invention renders the latter detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, cintillants, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases the detectable label emits a signal as a result of being stimulated by an external field.

Exemplary radioactive isotopes may be γ-emitting, Auger-emitting, β-emitting, an alpha-emitting or positron-emitting radioactive isotope. Exemplary radioactive isotopes include $^{3}H$, $^{11}C$, $^{13}C$, $^{15}N$, $^{18}F$, $^{19}F$, $^{55}Co$, $^{57}Co$, $^{60}Co$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{90}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, *neptunium* atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e., iodine) to 83 (i.e., bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The FN3 domains that specifically bind CD137 conjugated to a detectable label may be used as an imaging agent to evaluate tumor distribution, diagnosis for the presence of tumor cells and/or, recurrence of tumor.

In some embodiments, the FN3 domains that specifically bind CD137 of the invention are conjugated to a cytotoxic agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The FN3 domains that specifically bind CD137 conjugated to a cytotoxic agent of the invention may be used in the targeted delivery of the cytotoxic agent to CD137 expressing tumor cell, and intracellular accumulation therein, wherein systemic administration of these unconjugated cytotoxic agents may result in unacceptable levels of toxicity to normal cells.

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elict their cytotoxic and cytostatic effects by mechanisms including tubulin binding, DNA binding, or topoisomerase inhibition.

In some embodiments, the cytotoxic agent is an enzymatically active toxins such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}Bi$, $^{131}I$, $^{131}In$, $^{90}Y$, and $^{186}Re$.

In some embodiments, the cytotoxic agent is dolastatins or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancerand antifungal activity. The dolastatin or auristatin drug moiety may be attached to the FN3 domain of the invention through the N (amino) terminus or the C (carboxyl) terminus of the peptidic drug moiety (WO 02/088172), or via any cysteine engineered into the FN3 domain.

The FN3 domains that specifically bind CD137 of the invention may be conjugated to a detectable label using known methods.

In some embodiments, the detectable label is complexed with a chelating agent.

In some embodiments, the detectable label is conjugated to the FN3 domain that specifically binds CD137 of the invention via a linker.

The detectable label or the cytotoxic moiety may be linked directly, or indirectly, to the FN3 domain that specifically binds CD137 of the invention using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

In some embodiment, the FN3 domain that specifically binds CD137 is removed from the blood via renal clearance.

Isolation of CD137 Binding FN3 Domains from a Library Based on Tencon Sequence

Tencon (SEQ ID NO:1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind CD137. Table 1 shows positions and sequences of each loop and beta-strand in Tencon (SEQ ID NO:1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in U.S. Pat. Publ. No. 2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO:1), and which variants display improve thermal stability. Exemplary Tencon variants are described in US Pat. Publ. No. 2011/0274623, and include Tencon27 (SEQ ID NO:4) having substitutions E11R, L17A, N46V and E86I when compared to Tencon of SEQ ID NO:1.

TABLE 1

| FN3 domain | Tencon topology Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http://www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well-known IUB code.

The FN3 domains that specifically bind CD137 of the invention may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to PSMA by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains that specifically bind CD137 are further characterized for their binding to CD137, modulation of CD137 activity, internalization, stability, and other desired characteristics.

The FN3 domains that specifically bind CD137 of the invention may be generated using any FN3 domain as a template to generate a library and screening the library for molecules specifically binding CD137 using methods provided within. Exemplar FN3 domains that may be used are the 3rd FN3 domain of tenascin C (TN3) (SEQ ID NO:32), Fibcon (SEQ ID NO:33), and the 10$^{th}$ FN3 domain of fibronectin (FN10) (SEQ ID NO:34). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172,197; 5,223,409; 6,582,915; 6,472,147).

In some embodiments. the FN3 domain that specifically binds CD137 is based on Tencon sequence of SEQ ID NO:1 or Tencon27 sequence of SEQ ID NO:4, the SEQ ID NO:1 or the SEQ ID NO:4, optionally having substitutions at residues positions 11, 14, 17, 37, 46, 73, and/or 86.

The FN3 domains that specifically bind CD137 of the invention may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO:1) are residue positions 11, 14, 17, 37, 46, 73, or 86, and are described in US Pat. Publ. No. 2011/0274623. Substitutions corresponding to these residues may be incorporated to the FN3 domain containing molecules of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In one embodiment, the FN3 domain that specifically binds CD137 of the invention may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the $T_m$.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain that specifically binds CD137 may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO:35), $(GGGS)_2$ (SEQ ID NO:36), $(GGGGS)_5$ (SEQ ID NO:37), $(AP)_2$ (SEQ ID NO:38), $(AP)_5$ (SEQ ID NO:39), $(AP)_{10}$ (SEQ ID NO:40), $(AP)_{20}$ (SEQ ID NO:41) and $A(EAAAK)_5AAA$ (SEQ ID NO:42). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Half-Life Extending Moieties

The FN3 domains that specifically bind CD137 may incorporate other subunits for example via covalent interaction. In one aspect of the invention, the FN3 domains that specifically bind CD137 further comprise a half-life extending moiety. Exemplary half-life extending moieties are albumin, albumin variants, albumin-binding proteins and/or domains, transferrin and fragments and analogues thereof, and Fc regions. An exemplary albumin variant is shown in SEQ ID NO:43. Amino acid sequences of the human Fc regions are well known, and include IgG1, IgG2, IgG3, IgG4, IgM, IgA and IgE Fc regions.

All or a portion of an antibody constant region may be attached to the FN3 domain that specifically binds CD137 to impart antibody-like properties, especially those properties associated with the Fc region, such as Fc effector functions such as Clq binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see Strohl, *Curr Opin Biotechnol.* 20, 685-691, 2009).

Additional moieties may be incorporated into the FN3 domains that specifically bind CD137 such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the FN3 domain that specifically binds CD137 by incorporating a cysteine residue to the C-terminus of the molecule, or engineering cysteines into residue positions that face away from the CD137 binding face of the molecule, and attaching a pegyl group to the cysteine using well known methods.

FN3 domains that specifically bind CD137 incorporating additional moieties may be compared for functionality by several well-known assays. For example, altered properties due to incorporation of Fc domains and/or Fc domain variants may be assayed in Fc receptor binding assays using soluble forms of the receptors, such as the FcγRT, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention also provides nucleic acids encoding the FN3 domains specifically binding CD137 as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the FN3 domains of the invention are also within the scope of the invention.

The invention also provides an isolated polynucleotide encoding the FN3 domain specifically binding CD137 comprising the amino acid sequence of SEQ ID NOs: 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, or 224.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such as PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

The invention also provides a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

The invention also provides a host cell comprising the vector of the invention. The FN3 domain that specifically bind CD137 may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The invention also provides a method of producing the isolated FN3 domain that specifically binds CD137, comprising culturing the isolated host cell of the invention under conditions such that the isolated FN3 domain that specifically binds CD137 is expressed, and purifying the FN3 domain.

The FN3 domains that specifically bind CD137 may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Anti-Idiotypic Antibodies

The present invention also provides an anti-idiotypic antibody binding to the FN3 domain.

The invention also provides an anti-idiotypic antibody that specifically binds the FN3 domain comprising the amino acid sequences of one of SEQ ID NOs: 45-224.

Kits

The invention also provides a kit comprising the FN3 domain that specifically binds CD137.

The kit may be used for therapeutic uses and as a diagnostic kit.

In some embodiments, the kit comprises the FN3 domain that specifically binds CD137 and reagents for detecting the FN3 domain. The kit can include one or more other elements including: instructions for use; other reagents, e.g., a label, an agent useful for chelating, or otherwise coupling, a radioprotective composition; devices or other materials for preparing the FN3 domain that specifically binds CD137 for administration for imaging, diagnostic or therapeutic purpose; pharmaceutically acceptable carriers; and devices or other materials for administration to a subject.

In some embodiments, the kit comprises the FN3 domain that specifically binds CD137 comprising the amino acid sequences of one of SEQ ID NOs: 45-224.

Uses of CD137 Binding FN3 Domains of the Invention

The FN3 domains that specifically bind CD137 may be used to diagnose, monitor, modulate, treat, alleviate, help prevent the incidence of, or reduce the symptoms of human disease or specific pathologies in cells, tissues, organs, fluid, or, generally, a host. The FN3 domains that specifically bind CD137 may also be used in imaging CD137 positive tumor tissue in a subject. The methods of the invention may be used with an animal patient belonging to any classification. Examples of such animals include mammals such as humans, rodents, dogs, cats and farm animals.

The invention provides a method of diagnosing a subject having, or who is likely to develop cancer of a tissue based on the expression of CD137 by cells of the cancer tissue, methods of predicting success of immunotherapy, methods of prognosis, and methods of treatment.

The invention also provides a method of detecting CD137-expressing cancer cells in a tumor tissue, comprising
obtaining a sample of the tumor tissue from a subject;
detecting whether CD137 is expressed in the tumor tissue by contacting toe sample of the tumor tissues with the FN3 domain that specifically binds CD137 comprising the amino acid sequence of one of SEQ ID NOs: 45-224 and detecting the binding between CD137 and the FN3 domain.

The tissue can be tissue of any organ or anatomical system, for example lung, epithelial, connective, vascular, muscle, neural, skeletal, lymphatic, prostate, cervical, breast, spleen, gastric, intestinal, oral, esophageal, uterine, ovarian, renal or testicular tissue.

CD137 expression may be evaluated using known methods, such as immunohistochemistry or ELISA.

The invention also provides a method of isolating CD137 expressing cells, comprising
obtaining a sample from a subject;
contacting the sample with the FN3 domain that specifically binds CD137 comprising the amino acid sequence of one of SEQ ID NOs: 45-224, and
isolating the cells bound to the FN3 domains.

The invention also provides a method of detecting CD137-expressing cancer cells in a tumor tissue, comprising
conjugating the FN3 domain that specifically binds CD137 comprising the amino acid sequence of one of SEQ ID NOs: 45-224 to a detectable label to form a conjugate;
administering the conjugate to a subject; and
visualizing the CD137 expressing cancer cells to which the conjugate is bound.

The invention also provides a method of treating a subject having cancer, comprising administering to the subject a FN3 domain that specifically binds CD137 of the invention.

In some embodiments, the subject has a solid tumor.

In some embodiments, the subject has a hematological malignancy.

In some embodiments, the solid tumor is a melanoma.

In some embodiments, the solid tumor is a lung cancer.

In some embodiments, the solid tumor is a non-small cell lung cancer (NSCLC).

In some embodiments, the solid tumor is a squamous non-small cell lung cancer (NSCLC).

In some embodiments, the solid tumor is a non-squamous NSCLC.

In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer.

In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the hematological malignancy is a lymphoma, a myeloma or a leukemia.

In some embodiments, the hematological malignancy is a B cell lymphoma.

In some embodiments, the hematological malignancy is Burkitt's lymphoma.

In some embodiments, the hematological malignancy is Hodgkin's lymphoma.

In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML).

In some embodiments, the hematological malignancy is a chronic myeloid leukemia (CML).

In some embodiments, the hematological malignancy is a chronic myelomoncytic leukemia (CMML).

In some embodiments, the hematological malignancy is a multiple myeloma (MM).

In some embodiments, the hematological malignancy is a plasmacytoma. In some embodiments, the cancer is kidney cancer.

"Treat" or "treatment" refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the FN3 domains that specifically bind CD137 of the invention may vary according to factors such as the disease state, age, sex, and weight of the individual. Exemplary indicators of an effective FN3 domain that specifically binds CD137 is improved well-being of the patient, decrease or shrinkage of the size of a tumor, arrested or slowed growth of a tumor, and/or absence of metastasis of cancer cells to other locations in the body.

Administration/Pharmaceutical Compositions

The invention provides for pharmaceutical compositions of the FN3 domains that specifically bind CD137, optionally conjugated to a detectable label or a cytotoxic drug of the invention and a pharmaceutically acceptable carrier. For therapeutic use, the FN3 domains that specifically bind CD137 of the invention may be prepared as pharmaceutical compositions containing an effective amount of the domain or molecule as an active ingredient in a pharmaceutically acceptable carrier. "Carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules of the invention in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the FN3 domains of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

While having described the invention in general terms, the embodiments of the invention will be further disclosed in the following examples that should not be construed as limiting the scope of the claims.

EXAMPLES

Example 1: Construction of Tencon Libraries with Randomized Loops

Tencon (SEQ ID NO:1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

```
Tencon:
(SEQ ID NO 1):
LPAPKNLVVSEVTEDSLRLSWTAPDAAFDSFLIQYQESEKVGEAI

NLTVPGSERSYDLTGLKPGTEYTVSIYGVKGGHRSNPLSAEFTT
```

Various libraries were generated using the tencon scaffold and various design strategies. In general, libraries TCL1 and TCL2 produced good binders. Generation of TCL1 and TCL2 libraries are described in detail in Int. Pat. Publ. No. WO/2014081944A2.

Construction of TCL1 Library

A library designed to randomize only the FG loop of Tencon (SEQ ID NO:1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon, KGGHRSN (SEQ ID NO:55). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

```
TCL1 library
                                        (SEQ ID NO: 2)
LPAPKNLVVSEVTEDSLRLSWTAPDAAFDSFLIQYQESEKVGE

AINLTVPGSERSYDLTGLKPGTEYTVSIYGVX₇₋₁₂PLSAEFTT;
``` wherein
$X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted Construction of TCL2 Library TCL2 library was constructed in which both the BC and the FG loops of Tencon were randomized and the distribution of amino acids at each position was strictly controlled. Table 3 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 2 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

```
TCL2 library
                                        (SEQ ID NO: 3)
LPAPKNLVVSEVTEDSLRLSWX₁X₂X₃X₄X₅X₆X₇X₈SFLIQYQESEK

VGEAINLTVPGSERSYDLTGLKPGTEYTVSIYGVX₉X₁₀X₁₁X₁₂X₁₃

SX₁₄X₁₅LSAEFTT;
``` wherein
$X_1$ is Ala, Arg, Asn, Asp, Glu, Gln, Gly, His, Ile, Leu, Lys, Phe, Pro, Ser, Thr, Trp, Tyr or Val;
$X_2$ is Ala, Arg, Asn, Asp, Glu, Gln, Gly, His, Ile, Leu, Lys, Phe, Pro, Ser, Thr, Trp, Tyr or Val;
$X_3$ Ala, Arg, Asn, Asp, Glu, Gln, Gly, His, Ile, Leu, Lys, Phe, Pro, Ser, Thr, Trp, Tyr or Val;
$X_4$ is Ala, Arg, Asn, Asp, Glu, Gln, Gly, His, Ile, Leu, Lys, Phe, Pro, Ser, Thr, Trp, Tyr or Val;
$X_5$ is Ala, Arg, Asn, Asp, Glu, Gln, Gly, His, Ile, Leu, Lys, Phe, Pro, Ser, Thr, Trp, Tyr or Val;
$X_6$ is Ala, Arg, Asn, Asp, Glu, Gln, Gly, His, Ile, Leu, Lys, Phe, Pro, Ser, Thr, Trp, Tyr or Val;
$X_7$ is Phe, Ile, Leu, Val or Tyr;
$X_8$ is Asp, Glu or Thr;
$X_9$ is Ala, Arg, Asn, Asp, Glu, Gln, Gly, His, Ile, Leu, Lys, Phe, Pro, Ser, Thr, Trp, Tyr or Val;
$X_{10}$ is Ala, Arg, Asn, Asp, Glu, Gln, Gly, His, Ile, Leu, Lys, Phe, Pro, Ser, Thr, Trp, Tyr or Val;
$X_{11}$ is Ala, Arg, Asn, Asp, Glu, Gln, Gly, His, Ile, Leu, Lys, Phe, Pro, Ser, Thr, Trp, Tyr or Val;
$X_{12}$ is Ala, Arg, Asn, Asp, Glu, Gln, Gly, His, Ile, Leu, Lys, Phe, Pro, Ser, Thr, Trp, Tyr or Val;
$X_{13}$ is Ala, Arg, Asn, Asp, Glu, Gln, Gly, His, Ile, Leu, Lys, Phe, Pro, Ser, Thr, Trp, Tyr or Val;
$X_{14}$ is Ala, Arg, Asn, Asp, Glu, Gln, Gly, His, Ile, Leu, Lys, Phe, Pro, Ser, Thr, Trp, Tyr or Val; and
$X_{15}$ is Ala, Arg, Asn, Asp, Glu, Gln, Gly, His, Ile, Leu, Lys, Phe, Pro, Ser, Thr, Trp, Tyr or Val.

TABLE 2

Residue distribution in the TCL2 library

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO:4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

```
Stabilized Tencon (Tencon27)
                                          (SEQ ID NO: 4)
LPAPKNLVVSRVTEDSARLSWTAPDAAFDSFLIQYQESEKVGEAIV

LTVPGSERSYDLTGLKPGTEYTVSIYGVKGGHRSNPLSAIFTT

TCL7 (randomized FG and BC loops)
                                          (SEQ ID NO: 5)
LPAPKNLVVSRVTEDSARLSWX₁X₂X₃X₄X₅X₆X₇X₈X₉FDSFLIQYQE

SEKVGEAIVLTVPGSERSYDLTGLKPGTEYTVSIYGVX₁₀X₁₁X₁₂X₁₃

X₁₄X₁₅X₁₆X₁₇X₁₈X₁₉SNPLSAIFTT;
wherein
X₁, X₂, X₃, X₄, X₅, X₆, X₁₀, X₁₁, X₁₂, X₁₃, X₁₄, X₁₅
and X₁₆ is A, D, E, F, G, H, I, K, L, N, P, Q,
R, S, T, V, W or Y; and X₇, X₈, X₉, X₁₇, X₁₈ and
X₁₉, is A, D, E, F, G, H, I, K, L, N, P, Q,
R, S, T, V, W, Y or deleted.

TCL9 (randomized FG loop)
                                          (SEQ ID NO: 6)
LPAPKNLVVSRVTEDSARLSWTAPDAAFDSFLIQYQESEKVGEAIV

LTVPGSERSYDLTGLKPGTEYTVSIYGV X₁X₂X₃X₄X₅X₆X₇X₈X₉

X₁₀X₁₁X₁₂SNPLSAIFTT;
X₁, X₂, X₃, X₄, X₅, X₆ and X₇, is A, D, E, F, G,
H, I, K, L, N, P, Q, R, S, T, V, W or Y; and
X₈, X₉, X₁₀, X₁₁ and X₁₂ is A. D, E, F, G, H, I,
K, L, N. P, Q, R, S, T, V, W, Y or deleted.
```

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO:9) and Sloning-Rev (SEQ ID NO:10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 µg) of 3' repA DNA in the presence of NotI and PspOMI enzyme and T4 ligase at 37° C. overnight. The ligated library product was amplified by using 12 cycles of PCR with oligos POP2250 (SEQ ID NO:11) and DigLigRev (SEQ ID NO:12). For each sub-library, the resulting DNA from 12 PCR reactions were combined and purified by Qiagen spin column. The yield for each sub-library of TCL9 ranged from 32-34 µg.

Construction of FG/BC Loop Libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID NOs: 13-16, respectively) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide encoding for amino acid A17 (130mer-L17A, SEQ ID NO:17) was produced by PCR using oligos POP2222ext (SEQ ID NO:18) and LS1114 (SEQ ID NO:19). This was done to include the L17A mutation in the library (CEN5243). Next, DNA fragments encoding for Tencon residues R18-V75 including randomized BC loops were amplified by PCR using BC6, BC7, BC8, or BC9 as a template and oligos LS1115 (SEQ ID NO:20) and LS1117 (SEQ ID NO:21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7, FG8, FG9, FG10, FG11, and FG12 as templates with oligonucleotides SDG10 (SEQ ID NO:22) and SDG24 (SEQ ID NO:23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID NO:24) and SDG28 SEQ ID NO:25). 7.5 µg of each reaction product were then digested with NotI and cleaned up with a Qiagen PCR purification column. 5.2 µg of this DNA, was ligated to an equal molar amount of RepA DNA fragment (~14 µg) digested with PspOMI and the product amplified by PCR using oligos POP2222.

Example 2: Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO:7), was designed into Tencon27 scaffold (SEQ ID NO:4).

A full description of the methods used to construct this library is described in US. Pat. Publ. No. 2013/0226834.

```
TCL14 library
(SEQ ID NO: 7):
LPAPKNLVVSRVTEDSARLSWTAPDAAFDSFX₁IX₂YX₃EX₄X₅

X₆X₇GEAIVLTVPGSERSYDLTGLKPGTEYX₈VX₉IX₁₀GVKGG

X₁₁X₁₂SX₁₃PLSAIFTT;
wherein
X₁, X₂, X₃, X₄, X₅, X₆, X₇, X₈, X₉, X₁₀, X₁₁,
X₁₂ and X₁₃ are A, D, E, F, G, H, I, K,
L, N, P, Q, R, S, T, V, W, Y, C or M.
```

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 3). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 2008) as described in Table 3. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 3.

```
TCL24 Library
                                          (SEQ ID NO: 8)
LPAPKNLVVSRVTEDSARLSWTAPDAAFDSFX₁IX₂YX₃EX₄X₅X₆

X₇GEAIX₈LX₉VPGSERSYDLTGLKPGTEYX₁₀NX₁₁IX₁₂GVKGG

X₁₃X₁₄SX₁₅PLX₁₆AX₁₇FTT;
wherein
X₁, X₂, X₃, X₄, X₅, X₆, X₁₀, X₁₁, X₁₂, X₁₃, X₁₄,
X₁₅, X₁₆ and X₁₇ are A, D, E, F, G, H, I, K,
L, N, P, Q, R, S, T, V, Y or W.
```

TABLE 3

Amino acid frequency (%) at each randomized position for TCL21, TCL23, and TCL24.

| Amino Acid | TCL19 | TCL21 | TCL23 | TCL24 |
| --- | --- | --- | --- | --- |
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |

TABLE 3-continued

Amino acid frequency (%) at each randomized position for TCL21, TCL23, and TCL24.

| Amino Acid | TCL19 | TCL21 | TCL23 | TCL24 |
|---|---|---|---|---|
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc Natl Acad Sci USA 101: 2806-2810, 2004) as described above for the loop libraries.

Example 3: Selection of Fibronectin Type III (FN3) Domains that Bind CD137

Panning

FN3 domains specific for human CD137 were selected via CIS-Display (Odegrip et al 2004) using recombinant biotinylated CD137 protein (Fc-fusion protein, R&D Systems 838-4B). For in vitro transcription and translation (ITT), 3 µg of DNA from Centyrin libraries TCL18, TCL19, TCL21, TCL23, and TCL24 (See accompanying library description document) were incubated at 30° C. with 0.1 mM complete amino acids, 1× S30 premix components, and 15 µL of S30 extract (Isogenica) in a total volume of 50 pt. After 1 hour, 375 µL of blocking solution (2% BSA in PBS, Invitrogen) was added and reactions were incubated on a cold block for 15 minutes. Unbound library members were removed by successive washes with TBST and TBS. After washing, DNA was eluted from the target protein by heating to 75° C. for 10 minutes and amplified by PCR using KOD polymberase for further rounds of panning. High affinity binders were isolated by successively lowering the concentration of target CD137 during each round from 400 nM to 100 nM and increasing the washing stringency.

Outputs from the fifth round panning were subjected to four additional rounds of off-rate selection. Library transcription and translation was performed as described above after which, the ITT reactions were incubated with biotinylated recombinant CD137 proteins and captured on neutravidin or streptavidin coated magnetic beads, before being washed in TBST extensively then subsequently washed in 5 uM cold recombinant CD137 protein for 1 hour. The biotinylated target antigen concentration was reduced from 25 nM in rounds 6 and 7 to 2.5 nM in rounds 8 and 9.

Following panning, genes encoding the selected FN3 domains were amplified by PCR, subcloned into a pET vector modified to include a ligase independent cloning site, and transformed into BL21 (DE3) (Stratagene) cells for soluble expression in *E. coli* using standard molecular biology techniques. A gene sequence encoding a C-terminal poly-histidine tag was added to each Centyrin to enable purification and detection. Cultures were grown to an optical density of 0.6-0.8 in TB medium supplemented with 100 µg/mL carbenicillin in 1 mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen EMD Biosciences) supplemented with 0.2 mg/mL lysozyme with shaking at room temperature for 30 minutes.

Biochemical Screening for FN3 Domains that Recombinant CD137

Streptavidin-coated Maxisorp plates (Nunc catalog 436110) were blocked for 1 h in Starting Block T20 (Pierce) and then coated with biotinylated CD137 (using same antigen as in panning) or negative controls (an unrelated Fc-fused recombinant protein and human serum albumin) for 1 h. Plates were rinsed with TBST and diluted lysate was applied to plates for 1 h. Following additional rinses, wells were treated with HRP-conjugated anti-Centyrin antibody (PAB25) for 1 h and then assayed with POD (Roche catalog 11582950001). The DNA from Centyrin lysates with signals at least 10-fold ELISA signal above that of Fc and HSA controls were sequenced resulting in 78 (Table 1) and 102 (Table 2) unique, readable Centyrin sequences isolated from Round 5 and Round 9 screening respectively.

High-Throughput Expression of Anti-CD137 FN3 Domains

102 Isolated clones from unique binding hits identified by biochemical binding ELISA from Round 9 were combined for growth into 96-well block plate; clones grew in 1 mL cultures (LB media supplemented with kanamycin for selection) at 37° C. overnight with shaking. For protein expression in 96-block plates, 1 mL TB media supplemented with kanamycin was inoculated with 50 uL of the overnight culture and grown at 37° C. with continual shaking at 300 rpm until $OD_{600}$=0.6–1. Once the target OD was reached, protein expression was induced with addition of IPTG to 1 mM; plates were transferred to 30° C. (300 rpm) for overnight growth. Overnight cultures were centrifuged to harvest the cells; bacterial pellets were stored at −80° C. until ready for use. Pellets were lysed with BugBuster® HT lysis buffer (Novagen EMD Biosciences) and His-tagged FN3 domains purified from the clarified lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of anti-CD137 FN3 domains. Aliquots (10 µL) of each purified Centyrin were injected onto a Superdex 75 5/150 column (GE Healthcare) at a flow rate of 0.3 mL/min in a mobile phase of PBS pH 7.4. Elution from the column was monitored by absorbance at 280 nm. Tencon protein was included in each run as a control. Agilent ChemStation software was used to analyse the elution profiles. 46 anti-CD137 FN3 domains demonstrated a retention time between 5.2 and 6.4 minutes and only a single SEC peak indicative of monomeric protein.

TABLE 4

Summary of Round 5 Screening Hits

| FN3 Domain | ELISA CD137-Fc (RLU) | ELISA Fc Control (RLU) | ELISA HSA (RLU) | SEQ ID No. |
|---|---|---|---|---|
| ISOP120AR5P1D2 | 907520 | 640 | 640 | 45 |
| ISOP120AR5P1C3 | 927040 | 320 | 240 | 46 |
| ISOP120AR5P1H3 | 769280 | 400 | 480 | 47 |

TABLE 4-continued

Summary of Round 5 Screening Hits

| FN3 Domain | ELISA CD137-Fc (RLU) | ELISA Fc Control (RLU) | ELISA HSA (RLU) | SEQ ID No. |
|---|---|---|---|---|
| ISOP120AR5P1C4 | 708240 | 320 | 240 | 48 |
| ISOP120AR5P1B5 | 500640 | 400 | 320 | 49 |
| ISOP120AR5P1C5 | 425120 | 320 | 160 | 50 |
| ISOP120AR5P1G7 | 568000 | 560 | 480 | 51 |
| ISOP120AR5P1G8 | 541200 | 320 | 320 | 52 |
| ISOP120AR5P1D9 | 636320 | 320 | 320 | 53 |
| ISOP120AR5P1F11 | 714800 | 480 | 320 | 54 |
| ISOP120AR5P1B12 | 864240 | 400 | 480 | 55 |
| ISOP120BR5P1C1 | 437680 | 480 | 480 | 56 |
| ISOP120BR5P1F1 | 541920 | 480 | 480 | 57 |
| ISOP120BR5P1D2 | 360800 | 720 | 240 | 58 |
| ISOP120BR5P1E2 | 882480 | 5680 | 4960 | 59 |
| ISOP120BR5P1F2 | 298800 | 400 | 240 | 60 |
| ISOP120BR5P1D3 | 1138560 | 240 | 400 | 61 |
| ISOP120BR5P1H3 | 874560 | 2000 | 720 | 62 |
| ISOP120BR5P1E4 | 942320 | 320 | 560 | 63 |
| ISOP120BR5P1G4 | 580240 | 480 | 400 | 64 |
| ISOP120BR5P1A5 | 503040 | 640 | 400 | 65 |
| ISOP120BR5P1E6 | 779120 | 320 | 400 | 66 |
| ISOP120BR5P1B7 | 564560 | 400 | 480 | 67 |
| ISOP120BR5P1C7 | 306240 | 880 | 240 | 68 |
| ISOP120BR5P1D8 | 941680 | 480 | 320 | 69 |
| ISOP120BR5P1E8 | 906160 | 480 | 640 | 70 |
| ISOP120BR5P1B9 | 358000 | 560 | 400 | 71 |
| ISOP120BR5P1C9 | 1272800 | 320 | 560 | 72 |
| ISOP120BR5P1D9 | 1224720 | 560 | 560 | 73 |
| ISOP120BR5P1A10 | 573280 | 36160 | 26560 | 74 |
| ISOP120BR5P1G11 | 485440 | 480 | 560 | 75 |
| ISOP120GR5P1E1 | 1022960 | 320 | 320 | 76 |
| ISOP120GR5P1G3 | 1335760 | 320 | 320 | 77 |
| ISOP120GR5P1F5 | 1283680 | 400 | 400 | 78 |
| ISOP120GR5P1H6 | 721440 | 400 | 400 | 79 |
| ISOP120GR5P1E7 | 1130720 | 400 | 480 | 80 |
| ISOP120GR5P1A10 | 626640 | 400 | 400 | 81 |
| ISOP120GR5P1C10 | 501840 | 240 | 480 | 82 |
| ISOP120GR5P1A11 | 1045760 | 480 | 320 | 83 |
| ISOP120GR5P1B11 | 875360 | 320 | 160 | 84 |
| ISOP120GR5P1H11 | 1310560 | 640 | 320 | 85 |
| ISOP120HR5P1E2 | 1319040 | 720 | 2880 | 86 |
| ISOP120HR5P1A3 | 1076480 | 560 | 240 | 87 |
| ISOP120HR5P1B4 | 1185360 | 320 | 320 | 88 |
| ISOP120HR5P1G4 | 346880 | 320 | 480 | 89 |
| ISOP120HR5P1H4 | 630480 | 480 | 320 | 90 |
| ISOP120HR5P1B5 | 519520 | 320 | 240 | 91 |
| ISOP120HR5P1A6 | 1292720 | 640 | 400 | 92 |
| ISOP120HR5P1G6 | 2035360 | 400 | 320 | 93 |
| ISOP120HR5P1A7 | 986800 | 400 | 480 | 94 |
| ISOP120HR5P1D7 | 1104240 | 320 | 320 | 95 |
| ISOP120HR5P1E7 | 363120 | 480 | 480 | 96 |
| ISOP120HR5P1H7 | 1527200 | 640 | 480 | 97 |
| ISOP120HR5P1H8 | 2217040 | 320 | 400 | 98 |
| ISOP120HR5P1D9 | 404720 | 480 | 400 | 99 |
| ISOP120HR5P1F9 | 1177120 | 400 | 400 | 100 |
| ISOP120ER5P1B4 | 499360 | 400 | 400 | 101 |
| ISOP120ER5P1F4 | 536720 | 320 | 400 | 102 |
| ISOP120ER5P1H4 | 1070240 | 480 | 560 | 103 |
| ISOP120ER5P1E5 | 413120 | 240 | 320 | 104 |
| ISOP120ER5P1B6 | 1351600 | 160 | 400 | 105 |
| ISOP120ER5P1C6 | 495360 | 320 | 400 | 106 |
| ISOP120ER5P1H6 | 588560 | 320 | 480 | 107 |
| ISOP120ER5P1A7 | 1114080 | 400 | 400 | 108 |
| ISOP120ER5P1A8 | 1897040 | 400 | 320 | 109 |
| ISOP120ER5P1E10 | 810320 | 720 | 400 | 110 |
| ISOP120ER5P1A11 | 1144160 | 320 | 320 | 111 |
| ISOP120ER5P1B12 | 1441520 | 720 | 800 | 112 |
| ISOP120FR5P1F1 | 1228320 | 480 | 640 | 113 |
| ISOP120FR5P1C2 | 388960 | 240 | 400 | 114 |
| ISOP120FR5P1H5 | 459680 | 400 | 560 | 115 |
| ISOP120FR5P1A6 | 1404240 | 400 | 320 | 116 |
| ISOP120FR5P1H6 | 356880 | 320 | 320 | 117 |
| ISOP120FR5P1D7 | 1178800 | 400 | 480 | 118 |
| ISOP120FR5P1F8 | 1197120 | 240 | 400 | 119 |
| ISOP120FR5P1E9 | 1183360 | 320 | 400 | 120 |
| ISOP120FR5P1E10 | 953040 | 240 | 320 | 121 |
| ISOP120FR5P1A11 | 920080 | 480 | 480 | 122 |

TABLE 5

Summary of Round 9 Screening Hits

| FN3 Domain Clone | ELISA CD137 (RLU) | ELISA Fc Control (RLU) | ELISA HSA (RLU) | SEC Retention Time (min) | SEC Peak Height (mAU) | Monomeric | SEQ ID No. |
|---|---|---|---|---|---|---|---|
| ISOP193AR9P1A11 | 8659280 | 1440 | 320 | No peak | | FALSE | 123 |
| ISOP193AR9P1A6 | 6739840 | 960 | 480 | No peak | | FALSE | 124 |
| ISOP193AR9P1B10 | 8120400 | 1520 | 480 | 5.355 | 84.76 | TRUE | 125 |
| ISOP193AR9P1B12 | 2762240 | 2240 | 1440 | 5.712 | 39.72 | TRUE | 126 |
| ISOP193AR9P1B4 | 5744400 | 960 | 480 | 5.495 | 94.79 | TRUE | 127 |
| ISOP193AR9P1C10 | 7143200 | 3520 | 960 | No peak | | FALSE | 128 |
| ISOP193AR9P1E6 | 4179680 | 1200 | 720 | No peak | | FALSE | 129 |
| ISOP193AR9P1F4 | 3836000 | 1520 | 720 | 5.664 | 80.79 | TRUE | 130 |
| ISOP193AR9P1F9 | 4710240 | 1600 | 560 | 5.317 | 142.48 | TRUE | 131 |
| ISOP193AR9P1G11 | 5892800 | 2240 | 960 | 5.234 | 225.17 | | 132 |
| ISOP193AR9P1G5 | 4022880 | 1120 | 720 | 5.315 | 191.85 | FALSE | 133 |
| ISOP193AR9P1G8 | 4255040 | 1440 | 720 | No peak | 1.40 | FALSE | 134 |
| ISOP193AR9P1H8 | 3716320 | 3040 | 1040 | 5.982 | 36.60 | TRUE | 135 |
| ISOP193BR9P1B10 | 9733920 | 2640 | 1200 | 5.884 | 66.69 | TRUE | 136 |
| ISOP193BR9P1B12 | 6551440 | 14000 | 2880 | No peak | | FALSE | 137 |
| ISOP193BR9P1E6 | 4625840 | 2560 | 560 | 6.326 | 5.13 | FALSE | 138 |
| ISOP193BR9P1G11 | 4988080 | 56880 | 9600 | No peak | | FALSE | 139 |
| ISOP193BR9P1G2 | 6145520 | 15920 | 2160 | No peak | | FALSE | 140 |
| ISOP193BR9P1G3 | 4710400 | 1360 | 640 | 7.974 | 7.68 | FALSE | 141 |
| ISOP193BR9P1G6 | 8092720 | 2640 | 960 | 6.045 | 11.68 | TRUE | 142 |
| ISOP193BR9P1G9 | 3725520 | 1200 | 720 | 6.028 | 4.71 | FALSE | 143 |
| ISOP193BR9P1H2 | 3502960 | 11840 | 3280 | 6.055 | 55.87 | FALSE | 144 |
| ISOP193BR9P1H3 | 5257440 | 2080 | 1360 | No peak | | FALSE | 145 |
| ISOP193BR9P1H6 | 8857840 | 8320 | 2880 | 5.787 | 64.85 | FALSE | 146 |

TABLE 5-continued

Summary of Round 9 Screening Hits

| FN3 Domain Clone | ELISA CD137 (RLU) | ELISA Fc Control (RLU) | ELISA HSA (RLU) | SEC Retention Time (min) | SEC Peak Height (mAU) | Monomeric | SEQ ID No. |
|---|---|---|---|---|---|---|---|
| ISOP193ER9P1A10 | 14863840 | 1120 | 240 | No peak | | FALSE | 147 |
| ISOP193ER9P1A11 | 12781600 | 1200 | 640 | 6.015 | 35.38 | TRUE | 148 |
| ISOP193ER9P1A3 | 14185440 | 3040 | 880 | 5.73 | 136.02 | TRUE | 149 |
| ISOP193ER9P1A4 | 9806400 | 960 | 480 | 5.738 | 61.50 | TRUE | 150 |
| ISOP193ER9P1A8 | 14274800 | 1440 | 400 | 5.892 | 14.52 | TRUE | 151 |
| ISOP193ER9P1B4 | 16089360 | 1600 | 320 | No peak | | FALSE | 152 |
| ISOP193ER9P1B5 | 12675520 | 1200 | 400 | 6.033 | 8.43 | TRUE | 153 |
| ISOP193ER9P1C10 | 8866800 | 2480 | 560 | 5.704 | 179.28 | TRUE | 154 |
| ISOP193ER9P1C4 | 15455120 | 960 | 320 | 6.032 | 18.18 | TRUE | 155 |
| ISOP193ER9P1C8 | 16680560 | 1040 | 400 | 5.862 | 19.39 | TRUE | 156 |
| ISOP193ER9P1C9 | 14280160 | 880 | 560 | 5.668 | 20.02 | TRUE | 157 |
| ISOP193ER9P1D4 | 16022720 | 1120 | 480 | 5.843 | 22.38 | TRUE | 158 |
| ISOP193ER9P1D7 | 10954000 | 1680 | 400 | 5.92 | 80.79 | TRUE | 159 |
| ISOP193ER9P1E1 | 14972480 | 1200 | 560 | 5.755 | 18.97 | TRUE | 160 |
| ISOP193ER9P1E2 | 15691600 | 1040 | 560 | 6.296 | 20.36 | TRUE | 161 |
| ISOP193ER9P1E4 | 12645760 | 1680 | 480 | 5.762 | 118.21 | TRUE | 162 |
| ISOP193ER9P1E8 | 16401200 | 880 | 480 | 5.699 | 16.07 | TRUE | 163 |
| ISOP193ER9P1F11 | 11182240 | 2240 | 400 | No peak | | FALSE | 164 |
| ISOP193ER9P1F7 | 15148960 | 1200 | 480 | 5.856 | 7.39 | TRUE | 165 |
| ISOP193ER9P1F9 | 14980400 | 1840 | 400 | 7.819 | 4.92 | FALSE | 166 |
| ISOP193ER9P1G11 | 14840160 | 1440 | 560 | 5.859 | 17.01 | TRUE | 167 |
| ISOP193ER9P1G2 | 7192960 | 1680 | 720 | 5.677 | 24.15 | TRUE | 168 |
| ISOP193ER9P1G4 | 13819760 | 1440 | 320 | 5.979 | 2.54 | FALSE | 169 |
| ISOP193ER9P1G5 | 15073600 | 1440 | 400 | No peak | | FALSE | 170 |
| ISOP193ER9P1G9 | 12900320 | 1280 | 400 | 5.781 | 6.70 | TRUE | 171 |
| ISOP193ER9P1H11 | 2080000 | 1360 | 640 | 5.991 | 39.63 | TRUE | 172 |
| ISOP193ER9P1H2 | 5183360 | 1360 | 560 | 5.833 | 53.11 | TRUE | 173 |
| ISOP193ER9P1H3 | 10515760 | 1520 | 400 | 6.073 | 7.45 | FALSE | 174 |
| ISOP193FR9P1A11 | 5784000 | 3520 | 880 | No peak | | FALSE | 175 |
| ISOP193FR9P1A5 | 9072080 | 95120 | 26240 | 6.033 | 8.14 | TRUE | 176 |
| ISOP193FR9P1C1 | 14116720 | 36800 | 8160 | 5.866 | 3.99 | FALSE | 177 |
| ISOP193FR9P1C5 | 8660800 | 79280 | 19200 | 6.377 | 20.91 | TRUE | 178 |
| ISOP193FR9P1C9 | 12306480 | 21040 | 4000 | 7.257 | 5.36 | FALSE | 179 |
| ISOP193FR9P1D1 | 8132800 | 1680 | 640 | No peak | | FALSE | 180 |
| ISOP193FR9P1D5 | 6046880 | 51680 | 10800 | 5.948 | 4.84 | TRUE | 181 |
| ISOP193FR9P1D7 | 2195360 | 15040 | 2640 | 6.077 | 1.98 | FALSE | 182 |
| ISOP193FR9P1E1 | 11602480 | 2000 | 880 | 5.84 | 28.48 | FALSE | 183 |
| ISOP193FR9P1E10 | 2051600 | 133120 | 31040 | 5.9 | 46.84 | TRUE | 184 |
| ISOP193FR9P1F8 | 8573040 | 25680 | 5040 | 5.652 | 3.10 | FALSE | 185 |
| ISOP193FR9P1G10 | 8908880 | 2480 | 880 | 6.864 | 2.25 | FALSE | 186 |
| ISOP193FR9P1G11 | 10788560 | 60640 | 10960 | 5.945 | 5.46 | TRUE | 187 |
| ISOP193FR9P1G2 | 7864240 | 2560 | 880 | No peak | | FALSE | 188 |
| ISOP193FR9P1G4 | 13950480 | 1840 | 640 | 5.834 | 5.47 | TRUE | 189 |
| ISOP193FR9P1G7 | 5500720 | 42320 | 10960 | 5.897 | 9.89 | TRUE | 190 |
| ISOP193FR9P1G8 | 14458880 | 25120 | 5040 | 5.874 | 5.87 | FALSE | 191 |
| ISOP193FR9P1G9 | 12761120 | 33600 | 6800 | 6.413 | 6.02 | FALSE | 192 |
| ISOP193FR9P1H6 | 11204000 | 88320 | 23040 | 5.712 | 7.91 | TRUE | 193 |
| ISOP193FR9P1H9 | 2420400 | 2000 | 800 | 5.987 | 23.27 | TRUE | 194 |
| ISOP193GR9P1A7 | 2153840 | 1040 | 480 | 5.634 | 10.89 | TRUE | 195 |
| ISOP193GR9P1B3 | 3457040 | 880 | 320 | 5.768 | 3.78 | FALSE | 196 |
| ISOP193GR9P1E10 | 10452960 | 1360 | 480 | No peak | | FALSE | 197 |
| ISOP193GR9P1F6 | 9846640 | 1360 | 400 | 5.656 | 4.72 | FALSE | 198 |
| ISOP193GR9P1F7 | 3480640 | 880 | 400 | 5.712 | 2.95 | FALSE | 199 |
| ISOP193GR9P1G9 | 3052480 | 960 | 480 | 5.645 | 7.32 | TRUE | 200 |
| ISOP193GR9P1H2 | 5314000 | 1360 | 640 | No peak | | FALSE | 201 |
| ISOP193HR9P1A10 | 12663280 | 5680 | 1520 | No peak | | FALSE | 202 |
| ISOP193HR9P1A11 | 16644800 | 28320 | 4240 | No peak | | FALSE | 203 |
| ISOP193HR9P1A5 | 14895120 | 6080 | 2080 | No peak | | FALSE | 204 |
| ISOP193HR9P1A6 | 14635040 | 24960 | 5120 | No peak | | FALSE | 205 |
| ISOP193HR9P1A7 | 14786080 | 48880 | 12640 | 6.013 | 9.21 | TRUE | 206 |
| ISOP193HR9P1B11 | 16579440 | 14960 | 4080 | No peak | | FALSE | 207 |
| ISOP193HR9P1B7 | 16384560 | 12960 | 2240 | No peak | | FALSE | 208 |
| ISOP193HR9P1C7 | 3436800 | 71360 | 10000 | 5.69 | 2.15 | FALSE | 209 |
| ISOP193HR9P1C8 | 18185520 | 1360 | 560 | 6.475 | 4.54 | TRUE | 210 |
| ISOP193HR9P1D11 | 14160720 | 48720 | 6240 | 5.936 | 5.80 | TRUE | 211 |
| ISOP193HR9P1D8 | 6271280 | 10880 | 2640 | 5.79 | 4.93 | TRUE | 212 |
| ISOP193HR9P1E2 | 9022400 | 13120 | 3840 | 5.801 | 4.22 | FALSE | 213 |
| ISOP193HR9P1E3 | 17767600 | 1120 | 640 | 6.564 | 3.11 | FALSE | 214 |
| ISOP193HR9P1E6 | 11258560 | 20080 | 3040 | 5.859 | 3.13 | FALSE | 215 |
| ISOP193HR9P1E8 | 16318560 | 3120 | 1520 | No peak | | FALSE | 216 |
| ISOP193HR9P1F10 | 15810240 | 1280 | 960 | No peak | | FALSE | 217 |
| ISOP193HR9P1F8 | 16086000 | 31280 | 6080 | No peak | | FALSE | 218 |
| ISOP193HR9P1G10 | 15586960 | 1360 | 800 | 6.226 | 2.97 | FALSE | 219 |

TABLE 5-continued

Summary of Round 9 Screening Hits

| FN3 Domain Clone | ELISA CD137 (RLU) | ELISA Fc Control (RLU) | ELISA HSA (RLU) | SEC Retention Time (min) | SEC Peak Height (mAU) | Monomeric | SEQ ID No. |
|---|---|---|---|---|---|---|---|
| ISOP193HR9P1G4 | 17180000 | 960 | 560 | 6.293 | 2.54 | FALSE | 220 |
| ISOP193HR9P1G5 | 15137440 | 24160 | 3360 | 5.913 | 9.58 | TRUE | 221 |
| ISOP193HR9P1G6 | 11499680 | 8160 | 1200 | No peak |  | FALSE | 222 |
| ISOP193HR9P1H10 | 14818080 | 43920 | 10080 | 6.107 | 2.19 | FALSE | 223 |
| ISOP193HR9P1H7 | 4604800 | 49840 | 13680 | 6.035 | 1.81 | FALSE | 224 |

Example 4: Characterization of Fibronectin Type III (FN3) Domains that Bind CD137

Fluorescence-Activated Cell Sorting (FACS)

Cell surface binding was analyzed via flow cytometry. Cenyrins were prepared at a maximal concentration of 500 nM in the presence of 125 nM anti His-mIgG1 antibody and then serially diluted in PBS/1% FCS buffer. Samples were then applied to approx 100 000 CHO-K1 cells expressing the extracellular domain of human CD137 on their surface. Unbound Centyrin/Antibody complexes were washed away and bound FN3 domains were detected by the addition of goat anti mouse-FITC labeled antibody. Samples were then aquired by flow cytometry. Subsequently, Mean fluorescence intensity was plotted against the log Centyrin concentration and EC50 values were calculated by nonlinear regression using GraphPad Prism.

Binding Analysis with Biacore

For selected FN3 domains, binding to recombinant CD137-Fc was evaluated using surface plasmon resonance (Biacore T100). For each cycle approximately 500 RU of recombinant human CD137-Fc-IgG1 was captured via an anti human IgG immobilized on the surface of a CM5 chip. Once CD137-Fc protein was captured, increasing concentrations of Centyrin candidates were injected for 120 s and dissociation was then analyzed for 240 s. A flow cell immobilized with just the anti human IgG1 antibody served as reference flow cell. Kd values were subsequently extrapolated using a 1:1 kinetic binding model (BiaEvaluation software).

TABLE 6

Centyrin binding analysis by FACS and Biacore

| Centyrin Clone | EC50 FACS (nM) | Biacore (Kd) |
|---|---|---|
| ISOP193AR9P1B4 | 13.93 | n.d. |
| ISOP193AR9P1F4 | n.a. | n.d. |
| ISOP193AR9P1H8 | n.a. | n.d. |
| ISOP193AR9P1F9 | 218 | n.d. |
| ISOP193AR9P1B10 | 1.205 | n.d. |
| ISOP193AR9P1G11 | 10.48 | n.d. |
| ISOP193AR9P1B12 | n.a. | n.d. |
| ISOP193BR9P1G6 | n.a. | n.d. |
| ISOP193BR9P1B10 | 134 | n.d. |
| ISOP193GR9P1A7 | 605.6 | n.d. |
| ISOP193GR9P1G9 | n.a. | n.d. |
| ISOP193GR9P1F11 | 508.9 | n.d. |
| ISOP193HR9P1C8 | 3.268 | n.d. |
| ISOP193ER9P1E1 | 12.55 | 1.059E-08 |
| ISOP193ER9P1E2 | 15.31 | 1.094E-08 |
| ISOP193ER9P1G2 | 22.94 | 6.563E-08 |
| ISOP193ER9P1H2 | 27.46 | n.d. |
| ISOP193ER9P1A3 | 10.22 | 8.3E-09 |
| ISOP193ER9P1A4 | 27.1 | 1.172E-07 |
| ISOP193ER9P1C4 | 18.91 | 1.31E-08 |
| ISOP193ER9P1D4 | 12.86 | 9.552E-09 |
| ISOP193ER9P1E4 | 278.7 | n.d. |
| ISOP193ER9P1B5 | 7.342 | n.d. |
| ISOP193ER9P1D5 | 29.61 | n.d. |
| ISOP193ER9P1C7 | 19.07 | n.d. |
| ISOP193ER9P1F7 | 24.99 | n.d. |
| ISOP193ER9P1A8 | 16.96 | n.d. |
| ISOP193ER9P1C8 | 12.43 | n.d. |
| ISOP193ER9P1E8 | 17.67 | n.d. |
| ISOP193ER9P1C9 | 14.1 | 2.51E-08 |
| ISOP193ER9P1G9 | 15.26 | 5.986E-08 |
| ISOP193ER9P1C10 | 31.01 | 1.077E-07 |
| ISOP193ER9P1A11 | 10.56 | n.d. |
| ISOP193ER9P1G11 | 18.69 | n.d. |
| ISOP193ER9P1H11 | 184.5 | n.d. |
| ISOP193ER9P1B12 | 19.87 | n.d. |
| ISOP193FR9P1G4 | 26.93 | n.d. |
| ISOP193FR9P1H9 | 72.75 | n.d. |

SEQUENCES

SEQ ID NO: 1 = Original Tencon Sequence

LPAPKNLVVSEVTEDSLRLSWTAPDAAFDSFLIQYQESEKVGEAINLTVPGSERSY

DLTGLKPGTEYTVSIYGVKGGHRSNPLSAEFTT

SEQ ID NO: 2 = TCL1 library

LPAPKNLVVSEVTEDSLRLSWTAPDAAFDSFLIQYQESEKVGEAINLTVPGSERSY

DLTGLKPGTEYTVSIYGV(X)$_{7-12}$PL5AEFTT;

-continued wherein
$X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted SEQ ID NO: 3 = TCL2 library
LPAPKNLVVSEVTEDSLRLSWX$_1$X$_2$X$_3$X$_4$X$_5$X$_6$X$_7$X$_8$SFLIQYQESEKVGEAINLTVPGS ERSYDLTGLKPGTEYTVSIYGVX$_9$X$_{10}$X$_{11}$X$_{12}$X$_{13}$SX$_{14}$X$_{15}$L5AEFTT;
wherein
$X_1$ is Ala, Arg, Asn, Asp, Glu, Gln, Gly, His, Ile, Leu, Lys,
Phe, Pro, Ser, Thr, Trp, Tyr or Val;
$X_2$ is Ala, Arg, Asn, Asp, Glu, Gln, Gly, His, Ile, Leu, Lys,
Phe, Pro, Ser, Thr, Trp, Tyr or Val;
$X_3$ Ala, Arg, Asn, Asp, Glu, Gln, Gly, His, Ile, Leu, Lys,
Phe, Pro, Ser, Thr, Trp, Tyr or Val;
$X_4$ is Ala, Arg, Asn, Asp, Glu, Gln, Gly, His, Ile, Leu, Lys,
Phe, Pro, Ser, Thr, Trp, Tyr or Val;
$X_5$ is Ala, Arg, Asn, Asp, Glu, Gln, Gly, His, Ile, Leu, Lys,
Phe, Pro, Ser, Thr, Trp, Tyr or Val;
$X_6$ is Ala, Arg, Asn, Asp, Glu, Gln, Gly, His, Ile, Leu, Lys,
Phe, Pro, Ser, Thr, Trp, Tyr or Val;
$X_7$ is Phe, Ile, Leu, Val or Tyr;
$X_8$ is Asp, Glu or Thr;
$X_9$ is Ala, Arg, Asn, Asp, Glu, Gln, Gly, His, Ile, Leu, Lys,
Phe, Pro, Ser, Thr, Trp, Tyr or Val;
$X_{10}$ is Ala, Arg, Asn, Asp, Glu, Gln, Gly, His, Ile, Leu, Lys,
Phe, Pro, Ser, Thr, Trp, Tyr or Val;
$X_{11}$ is Ala, Arg, Asn, Asp, Glu, Gln, Gly, His, Ile, Leu, Lys,
Phe, Pro, Ser, Thr, Trp, Tyr or Val;
$X_{12}$ is Ala, Arg, Asn, Asp, Glu, Gln, Gly, His, Ile, Leu, Lys,
Phe, Pro, Ser, Thr, Trp, Tyr or Val;
$X_{13}$ is Ala, Arg, Asn, Asp, Glu, Gln, Gly, His, Ile, Leu, Lys,
Phe, Pro, Ser, Thr, Trp, Tyr or Val;
$X_{14}$ is Ala, Arg, Asn, Asp, Glu, Gln, Gly, His, Ile, Leu, Lys,
Phe, Pro, Ser, Thr, Trp, Tyr or Val; and
$X_{15}$ is Ala, Arg, Asn, Asp, Glu, Gln, Gly, His, Ile, Leu, Lys,
Phe, Pro, Ser, Thr, Trp, Tyr or Val.

SEQ ID NO: 4 = Stabilized Tencon
LPAPKNLVVSRVTEDSARLSWTAPDAAFDSFLIQYQESEKVGEAIVLTVPGSERSY

DLTGLKPGTEYTVSIYGVKGGHRSNPLSAIFTT

SEQ ID NO: 5 = TCL7 (FG and BC loops)
LPAPKNLVVSRVTEDSARLSWX$_1$X$_2$X$_3$X$_4$X$_5$X$_6$X$_7$X$_8$X$_9$FDSFLIQYQESEKVGEAIVLT VPGSERSYDLTGLKPGTEYTVSIYGVX$_{10}$X$_{11}$X$_{12}$X$_{13}$X$_{14}$X$_{15}$X$_{16}$X$_{17}$X$_{18}$X$_{19}$SNPLSAIFTT;
wherein
$X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ are A,
D, E, F, G, H, I, K, L, N, P, Q, R, S, T, V, W or Y; and
$X_7$, $X_8$, $X_9$, $X_{17}$, $X_{18}$ and $X_{19}$, are A, D, E, F, G, H, I, K, L, N,
P, Q, R, S, T, V, W, Y or deleted SEQ ID NO: 6 = TCL9 (FG loop)
LPAPKNLVVSRVTEDSARLSWTAPDAAFDSFLIQYQESEKVGEAIVLTVPGSERSY DLTGLKPGTEYTVSIYGV X$_1$X$_2$X$_3$X$_4$X$_5$X$_6$X$_7$X$_8$X$_9$X$_{10}$X$_{11}$X$_{12}$SNPLSAIFTT;
wherein
$X_1$, $X_2$, $X_3$, $X_4$, $X_5$, $X_6$ and $X_7$, is A, D, E, F, G, H, I, K, L, N,
P, Q, R, S, T, V, W or Y; and $X_8$, $X_9$, $X_{10}$, $X_{11}$ and $X_{12}$ is
A, D, E, F, G, H, I, K, L, N, P, Q, R, S, T, V, W, Y or
deleted.

TCL14 library (SEQ ID NO: 7):
LPAPKNLVVSRVTEDSARLSWTAPDAAFDSFX$_1$IX$_2$YX$_3$EX$_4$X$_5$X$_6$X$_7$GEAIVLTVPGS ERSYDLTGLKPGTEYX$_8$VX$_9$IX$_{10}$GVKGGX$_{11}$X$_{12}$SX$_{13}$PLSAIFTT;
wherein
$X_1$, $X_2$, $X_3$, $X_4$, $X_5$, $X_6$, $X_7$, $X_8$, $X_9$, $X_{10}$, $X_{11}$, $X_{12}$ and $X_{13}$ are A, D,
E, F, G, H, I, K, L, N, P, Q, R, S, T, V, W, Y, C or M.

TCL24 Library (SEQ ID NO: 8)
LPAPKNLVVSRVTEDSARLSWTAPDAAFDSFX$_1$IX$_2$YX$_3$EX$_4$X$_5$X$_6$X$_7$GEAIX$_8$LX$_9$VPG SERSYDLTGLKPGTEYX$_{10}$VX$_{11}$IX$_{12}$GVKGGX$_{13}$X$_{14}$SX$_{15}$PLX$_{16}$AX$_{17}$FTT;
wherein
$X_1$, $X_2$, $X_3$, $X_4$, $X_5$, $X_6$, $X_{10}$, $X_{11}$, $X_{12}$, $X_{13}$, $X_{14}$, $X_{15}$, $X_{16}$ and $X_{17}$
are A, D, E, F, G, H, I, K, L, N, P, Q, R, S, T, V, Y or W.

SEQ ID NO: 9 = Sloning-FOR
GTGACACGGCGGTTAGAAC

-continued

SEQ ID NO: 10 = Sloning-REV
GCCTTTGGGAAGCTTCTAAG

SEQ ID NO: 11 = POP2250
CGGCGGTTAGAACGCGGCTACAATTAATAC

SEQ ID NO: 12 = DigLigRev
CATGATTACGCCAAGCTCAGAA

SEQ ID NO: 13 = BC9
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTGAAGTTACCGAAGACTCTCTGCGTCTGTCTTGGNNNNNNNNNNNNNNN

NNNNNNNNNNNNTTYGACTCTTTCCTGATCCAGTACCAGGAATCTGAAAAAGT

TGGTGAAGCGATCAACCTGACCGTTCCGGGTTCTGAACGTTCTTACGACCTGA

CCGGTCTGAAACCGGGTACCGAATACACCGTTTCTATCTACGGTGTTCTTAGA

AGCTTCCCAAAGGC

SEQ ID NO: 14 = BC8
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTGAAGTTACCGAAGACTCTCTGCGTCTGTCTTGGNNNNNNNNNNNNNNN

NNNNNNNNNTTYGACTCTTTCCTGATCCAGTACCAGGAATCTGAAAAAGTTGG

TGAAGCGATCAACCTGACCGTTCCGGGTTCTGAACGTTCTTACGACCTGACCG

GTCTGAAACCGGGTACCGAATACACCGTTTCTATCTACGGTGTTCTTAGAAGC

TTCCCAAAGGC

SEQ ID NO: 15 = BC7
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTGAAGTTACCGAAGACTCTCTGCGTCTGTCTTGGNNNNNNNNNNNNNNN

NNNNNNTTYGACTCTTTCCTGATCCAGTACCAGGAATCTGAAAAAGTTGGTGA

AGCGATCAACCTGACCGTTCCGGGTTCTGAACGTTCTTACGACCTGACCGGTC

TGAAACCGGGTACCGAATACACCGTTTCTATCTACGGTGTTCTTAGAAGCTTC

CCAAAGGC

SEQ ID NO: 16 = BC6
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTGAAGTTACCGAAGACTCTCTGCGTCTGTCTTGGNNNNNNNNNNNNNNN

NNNTTYGACTCTTTCCTGATCCAGTACCAGGAATCTGAAAAAGTTGGTGAAGC

GATCAACCTGACCGTTCCGGGTTCTGAACGTTCTTACGACCTGACCGGTCTGA

AACCGGGTACCGAATACACCGTTTCTATCTACGGTGTTCTTAGAAGCTTCCCA

AAGGCAAGGC

-continued

SEQ ID NO: 17 = 130mer-L17A
CGGCGGTTAGAACGCGGCTACAATTAATACATAACCCCATCCCCCTGTTGACA

ATTAATCATCGGCTCGTATAATGTGTGGAATTGTGAGCGGATAACAATTTCAC

ACAGGAAACAGGATCTACCATGCTG

SEQ ID NO: 18 = POP222ext
CGG CGG TTA GAA CGC GGC TAC AAT TAA TAC

SEQ ID NO: 19 = LS1114
CCA AGA CAG ACG GGC AGA GTC TTC GGT AAC GCG AGA AAC AAC

CAG GTT TTT CGG CGC CGG CAG CAT GGT AGA TCC TGT TTC

SEQ ID NO: 20 = LS1115
CCG AAG ACT CTG CCC GTC TGT CTT GG

SEQ ID NO: 21 = LS1117
CAG TGG TCT CAC GGA TTC CTG GTA CTG GAT CAG GAA AGA GTC

GAA

SEQ ID NO: 22 = SDG10
CATGCGGTCTCTTCCGAAAAAGTTGGTGAAGCGATCGTCCTGACCGTTCCGGG
T

SEQ ID NO: 23 = SDG24
GGTGGTGAAGATCGCAGACAGCGGGTTAG

SEQ ID NO: 24 = P0P2222
CGGCGGTTAGAACGCGGCTAC

SEQ ID NO: 25 = SDG28
AAGATCAGTTGCGGCCGCTAGACTAGAACCGCTGCCACCGCCGGTGGTGAAG

ATCGCAGAC

SEQ ID NO: 26 = FG12
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTCGCGTTACCGAAGACTCTGCGCGTCTGTCTTGGACCGCGCCGGACGCG

GCGTTCGACTCTTTCCTGATCCAGTACCAGGAATCTGAAAAAGTTGGTGAAGC

GATCGTGCTGACCGTTCCGGGTTCTGAACGTTCTTACGACCTGACCGGTCTGA

AACCGGGTACCGAATACACCGTTTCTATCTACGGTGTTNNNNNNNNNNNNNNN

NNNNNNNNNNNNNNNNNNNNNTCTAACCCGCTGTCTGCGATCTTCACCACCGG

CGGTCACCATCACCATCACCATGGCAGCGGTTCTAGTCTAGCGGCCGCAACTG

ATCTTGGC

SEQ ID NO: 27 = FG11
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTCGCGTTACCGAAGACTCTGCGCGTCTGTCTTGGACCGCGCCGGACGCG

GCGTTCGACTCTTTCCTGATCCAGTACCAGGAATCTGAAAAAGTTGGTGAAGC

GATCGTGCTGACCGTTCCGGGTTCTGAACGTTCTTACGACCTGACCGGTCTGA

AACCGGGTACCGAATACACCGTTTCTATCTACGGTGTTNNNNNNNNNNNNNNN

NNNNNNNNNNNNNNNNNNNNNTCTAACCCGCTGTCTGCGATCTTCACCACCGGCGG

TCACCATCACCATCACCATGGCAGCGGTTCTAGTCTAGCGGCCGCAACTGATC

TTGGC

-continued

SEQ ID NO: 28 = FG10
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTCGCGTTACCGAAGACTCTGCGCGTCTGTCTTGGACCGCGCCGGACGCG

GCGTTCGACTCTTTCCTGATCCAGTACCAGGAATCTGAAAAAGTTGGTGAAGC

GATCGTGCTGACCGTTCCGGGTTCTGAACGTTCTTACGACCTGACCGGTCTGA

AACCGGGTACCGAATACACCGTTTCTATCTACGGTGTTNNNNNNNNNNNNNNN

NNNNNNNNNNNNNNNTCTAACCCGCTGTCTGCGATCTTCACCACCGGCGGTCA

CCATCACCATCACCATGGCAGCGGTTCTAGTCTAGCGGCCGCAACTGATCTTG

GC

SEQ ID NO: 29 = FG9
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTCGCGTTACCGAAGACTCTGCGCGTCTGTCTTGGACCGCGCCGGACGCG

GCGTTCGACTCTTTCCTGATCCAGTACCAGGAATCTGAAAAAGTTGGTGAAGC

GATCGTGCTGACCGTTCCGGGTTCTGAACGTTCTTACGACCTGACCGGTCTGA

AACCGGGTACCGAATACACCGTTTCTATCTACGGTGTTNNNNNNNNNNNNNNN

NNNNNNNNNNNNTCTAACCCGCTGTCTGCGATCTTCACCACCGGCGGTCACCA

TCACCATCACCATGGCAGCGGTTCTAGTCTAGCGGCCGCAACTGATCTTGGC

SEQ ID NO: 30 = FG8
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTCGCGTTACCGAAGACTCTGCGCGTCTGTCTTGGACCGCGCCGGACGCG

GCGTTCGACTCTTTCCTGATCCAGTACCAGGAATCTGAAAAAGTTGGTGAAGC

GATCGTGCTGACCGTTCCGGGTTCTGAACGTTCTTACGACCTGACCGGTCTGA

AACCGGGTACCGAATACACCGTTTCTATCTACGGTGTTNNNNNNNNNNNNNNN

NNNNNNNNNTCTAACCCGCTGTCTGCGATCTTCACCACCGGCGGTCACCATCA

CCATCACCATGGCAGCGGTTCTAGTCTAGCGGCCGCAACTGATCTTGGC

SEQ ID NO: 31 = FG7
GTGACACGGCGGTTAGAACGCGGCTACAATTAATACATAACCCCATCCCCCTG

TTGACAATTAATCATCGGCTCGTATAATGTGTGGAATTGTGAGCGGATAACAA

TTTCACACAGGAAACAGGATCTACCATGCTGCCGGCGCCGAAAAACCTGGTTG

TTTCTCGCGTTACCGAAGACTCTGCGCGTCTGTCTTGGACCGCGCCGGACGCG

GCGTTCGACTCTTTCCTGATCCAGTACCAGGAATCTGAAAAAGTTGGTGAAGC

GATCGTGCTGACCGTTCCGGGTTCTGAACGTTCTTACGACCTGACCGGTCTGA

AACCGGGTACCGAATACACCGTTTCTATCTACGGTGTTNNNNNNNNNNNNNNN

NNNNNNTCTAACCCGCTGTCTGCGATCTTCACCACCGGCGGTCACCATCACCA

TCACCATGGCAGCGGTTCTAGTCTAGCGGCCGCAACTGATCTTGGC

TABLE 7

FN3 Domains, Linkers, and Albumin variant

| Clone | SEQ ID NO: | AA Sequence |
|---|---|---|
| 3rd FN3 domain of tenascin C (TN3 | 32 | DAPSQIEVKDVTDTTALITWF KPLAEIDGIELTYGIKDVPGD RTTIDLTEDENQYSIGNLKPD TEYEVSLISRRGDMSSNPAKE TFTT |
| Fibcon | 33 | LDAPTDLQVTNVTDTSITVSW TPPSATITGYRITYTPSNGPG EPKELTVPPSSTSVTITGLTP GVEYWSLYALKDNQESPPLVG TQTT |
| 10th FN3 domain of fibronectin | 34 | VSDVPRDLEWAATPTSLLISW DAPAVTVRYYRITYGETGGNS PVQEFTVPGSKSTATISGLKP GVDYTITVYAVTGRGDSPASS KPISINYRT |
| Linker | 35 | GSGS |
| Linker | 36 | GGGSGGGS |
| Linker | 37 | GGGGSGGGGSGGGGSGGGGSG GGGS |
| Linker | 38 | APAP |
| Linker | 39 | APAPAPAPAP |
| Linker | 40 | APAPAPAPAPAPAPAPAP |
| Linker | 41 | APAPAPAPAPAPAPAPAP APAPAPAPAPAPAPAPAP |
| Linker | 42 | EAAAKEAAAKEAAAKEAAAK EAAAKAAA |
| Albumin variant | 43 | DAHKSEVAHRFKDLGEENFKA LVLIAFAQYLQQSPFEDHVKL VNEVTEFAKTCVADESAENCD KSLHTLFGDKLCTVATLRETY QGEMADCCAKQEPERNECFLH KKDDNPNLPRLVRPEVDVMCT AFHDNEETFLKYLYEIARRHP YFYAPELLFFAKRYKAAFTEC CQAADKAACLLPKLDELRDEG KASSAKQRLKCASLQKFGERA FKAWAVARLSQRFPKAEFAEV SKLVTDLTKVHTECCHGDLLE CADDRADLAKYICENQDSISS KLKECCEKPLLEKSHCIAEVE NDEMPADLPSLAADFVESKDV CKKYAEAKDVFLGMFLYEYAR RHPDYSVVLLLRLAKTYETTL EKCCAAADPHECYAKVFDEFK PLVEEPQNLIKQNCELFEQLG EYKFQNALLVRYTKKVPQVST PTLVEVSRNLGKVGSKCCKHP EAKRMPCAEDYLSVVLNQLCV LHEKTPVSDRVTKCCTESLVN RRPCFSALEVDETYVPKEFNA ETFTFHADICTLSEKERQIKK QTALVELVKHKPKATKEQLKA VMDDFAAFVEKCCKADDKETC FAEEGKKLVAASQAALGL |

SEQ ID NO: 44 = humanCD137
MGNSCYNIVATLLLVLNFERTRSLQDPCSNCPAGTFCDNNRNQICSPCPPNSFSSA

GGQRTCDICRQCKGVFRTRKECSSTSNAECDCTPGFHCLGAGCSMCEQDCKQGQEL

TKKGCKDCCFGTFNDQKRGICRPWTNCSLDGKSVLVNGTKERDVVCGPSPADLSPG

ASSVTPPAPAREPGHSPQIISFFLALTSTALLFLLFFLTLRFSVVKRGRKKLLYIF

KQPFMRPVQTTQEEDGCSCRFPEEEEGGCEL

CD137 binding fibronectin type III domains
ISOP120AR5P1D2
SEQ ID NO: 45
LPAPKNLVVSRVTEDSARLSWDFAYFKFDSFLIQYQESEKVGEAIVLTVPGSERSY

DLTGLKPGTEYTVSIYGVGRFYTVYYSNPLSAIFTT

ISOP120AR5P1C3
SEQ ID NO: 46
LPAPKNLVVSRVTEDSARLSWSPVDADFTFDSFLIQYQESEKVGEAIVLTVPGSER

SYDLTGLKPGTEYTVSIYGVGRHYTVYDSNPLSAIFTT

ISOP120AR5P1H3
SEQ ID NO: 47
LPAPKNLVVSRVTEDSARLSWKWISHEPLEFDSFLIQYQESEKVGEAIVLTVPGSER

SYDLTGLKPGTEYTVSIYGVGRHYTVYDSNPLSAIFTT

ISOP120AR5P1C4
SEQ ID NO: 48
LPAPKNLVVSRVTEDSARLSWAFQWHIFDSFLIQYQESEKVGEAIVLTVPGSERSY

DLTGLKPGTEYTVSIYGVGQPYTVYDSNPLSAIFTT

-continued

ISOP120AR5P1B5
SEQ ID NO: 49
LPAPKNLVVSRVTEDYARLSWKYGEHIIWFDSFLIQYQESEKVGEAIVLTVPGSER

SYDLTGLKPGTEYTVSIYGVKGQHDHDSNPLSAIFTT

ISOP120AR5P1C5
SEQ ID NO: 50
LPAPKNLVVSRVTEDSARLSWTLPNIHFDSFLIQYQESEKVGEAIVLTVPGSERSYD

LTGLKPGTEYTVSIYGVGRHYTVYDSNPLSAIFTT

ISOP120AR5P1G7
SEQ ID NO: 51
LPAPKNLVVSRVTEDSARLSWSQHYLSPIPFDSFLIQYQESEKVGEAIVLTVPGSER

SYDLTGLKPGTEYTVSIYGVGRHYTVYDSNPLSAIFTT

ISOP120AR5P1G8
SEQ ID NO: 52
LPAPKNLVVSRVTEDSARLSWHATFGDPFDSFLIQYQESEKVGEAIVLTVPGSERS

YDLTGLKPGTEYTVSIYGVGRHYTVYDSNPLSAIFTT

ISOP120AR5P1D9
SEQ ID NO: 53
LPAPKNLVVSRVTEDSARLSWNTDWVHTFDSFLIQYQESEKVGEAIVLTVPGSERS

YDLTGLKPGTEYTVSIYGVGRHYTVYDSNPLSAIFTT

ISOP120AR5P1F11
SEQ ID NO: 54
LPAPKNLVVSRVTEDSARLSWTNEQITKYGFDSFLIQYQESEKVGEAIVLTVPGSE

RSYDLTGLKPATEYTVSIYGVGRHYTVYDSNPLSAIFTT

ISOP120AR5P1B12
SEQ ID NO: 55
LPAPKNLVVSRVTEDSARLSWDGDKWANFKFDSFLIQYQESEKVGEAIVLTVPGS

ERSYDLTGLKPGTEYTVSIYGVGLHYIVYDSNPLSAIFTT

ISOP120BR5P1C1
SEQ ID NO: 56
LPAPKNLVVSRVTEDSARLSWVREDAYAFDSFLIQYQESEKVGEAIVLTVPGSERS

YDLTGLKPGTEYTVSIYGVSSLHWVVHDSNPLSAIFTT

ISOP120BR5P1F1
SEQ ID NO: 57
LPAPKNLVVSRVTEDSARLSWTFHPTFEGFDSFLIQYQESEKVGEAIVLTVPGSERS

YDLTGLKPGTEYTVSIYGVKWTVLRPWLSNPLSAIFTT

ISOP120BR5P1D2
SEQ ID NO: 58
LPAPKNLVVSRVTEDSARLSWIRKHNHVKWFDSFLIQYQESEKVGEAIVLTVPGSE

RSYDLTGLKPGTEYTVSIYGVGFLIDTDDSNPLSAIFTT

ISOP120BR5P1E2
SEQ ID NO: 59
LPAPKNLVVSRVTEDSARLSWAQELDHFDSFLIQYQESEKVGEAIVLTVPGSERSY

DLTGLKPGTEYTVSIYGVYWTWWVRWNSNPLSAIFTT

ISOP120BR5P1F2
SEQ ID NO: 60
LPAPKNLVVSRVTEDSARLSWTFHPTFEGFDSFLIQYQESEKVGEAIVLTVPGSERS

YDLTGLKPGTEYTVSIYGVKWYAGIGYPVSNPLSAIFTT

ISOP120BR5P1D3
SEQ ID NO: 61
LPAPKNLVVSRVTEDSARLSWSEHPTPFATFDSFLIQYQESEKVGEAIVLTVPGSER

SYDLTGLKPGTEYTVSIYGVWWVENHFPVSNPLSAIFTT

-continued

ISOP120BR5P1H3
SEQ ID NO: 62
LPAPKNLVVSRVTEDSARLSWEESRQFFDSFLIQYQESEKVGEAIVLTVPGSERSY

DLTGLKPGTEYTVSIYGVVHRAWLRWNGSNPLSAIFTT

ISOP120BR5P1E4
SEQ ID NO: 63
LPAPKNLVVSRVTEDSARLSWDDQFEDWFDSFLIQYQESEQVGEAIVLTVPGSERS

YDLTGLKPGTEYTVSIYGVHTRDWTAWNASNPLSAIFTT

ISOP120BR5P1G4
SEQ ID NO: 64
LPAPKNLVVSRVTEDSARLSWAGHYRKIRNFDSFLIQYQESEKVGEAIVLTVPGSE

RSYDLTGLKPGTEYTVSIYGVKFPYYYATADSNPLSAIFTT

ISOP120BR5P1A5
SEQ ID NO: 65
LPAPKNLVVSRVTEDSARLSWAGHYRKIRNFDSFLIQYQESEKVGEAIVLTVPGSK

RSYDLTGLKPGTEYTVSIYGVKFPYYYATADSNPLSAIFTT

ISOP120BR5P1E6
SEQ ID NO: 66
LPAPKNLVVSRVTEDSARLSWLEGANAEFDSFLIQYQESEKVGEAIVLTVPGSERS

YDLTGLKPGTEYTVSIYGVHWVGPWYPVSNPLSAIFTT

ISOP120BR5P1B7
SEQ ID NO: 67
LPAPKNLVVSRVTEDSARLSWGAKTRQFDSFLIQYQESEKVGEAIVLTVPGSERSY

DLTGLKPGTEYTVSIYGVWWVENHFPVSNPLSAIFTT

ISOP120BR5P1C7
SEQ ID NO: 68
LPAPKNLVVSRVTEDSARLSWNVTQKEFDSFLIQYQESEKVGEAIVLTVPGSERSY

DLTGLKPGTEYTVSIYGVGNRYYTVYDSNPLSAIFTT

ISOP120BR5P1D8
SEQ ID NO: 69
LPAPKNLVVSRVTEDSARLSWKNHTQEWEFDSFLIQYQESEKVGEAIVLTVPGSER

SYDLTGLKPGTEYTVSIYGVPIAWLAWTSTSNPLSAIFTT

ISOP120BR5P1E8
SEQ ID NO: 70
LPAPKNLVVSRVTEDSARLSWNGGEYWVPRFDSFLIQYQESEKVGEAIVLTVPGS

ERSYDLTGLKPGTEYTVSIYGVVWLQWISWTDSNPLSAIFTT

ISOP120BR5P1B9
SEQ ID NO: 71
LPAPKNLVVSRVTEDSARLSWAVEFNPTKFDSFLIQYQESEKVGEAIVLTVPGSER

SYDLTGLKPGTEYTVSIYGVWWFEQWYPVSNPLSAIFTT

ISOP120BR5P1C9
SEQ ID NO: 72
LPAPKNLVVSRVTEDSARLSWAWNRHDFDSFLIQYQESEKVGEAIVLTVPGSERS

YDLTGLKPGTEYTVSIYGVHWTVLRPFIDSNPLSAIFTT

ISOP120BR5P1D9
SEQ ID NO: 73
LPAPKNLVVSRVTEDSARLSWTINSHIFDSFLIQYQESEKVGEAIVLTVPGSERSYD

LTGLKPGTEYTVSIYGVWGTKYWQAQSNPLSAIFTT

ISOP120BR5P1A10
SEQ ID NO: 74
LPAPKNLVVSRVTEDSARLSWTEEDITHLRFDSFLIQYQESEKVGEAIVLTVPGSER

SYDLTGLKPGTEYTVSIYGVYWTWWVRWNSNPLSAIFTT

ISOP120BR5P1G11
SEQ ID NO: 75
LPAPKNLVVSRVTEDSARLSWTKRHFYTFDSFLIQYQESEKVGEAIVLTVPGSERS

YYLTGLKPGTENTVSIYGVHGNHPYTDAPANPLSAIFTT

ISOP120GR5P1E1
SEQ ID NO: 76
LPAPKNLVVSRVTEDSARLSWTAPDAAFDSFIIQYAEDSSWGEAINLHVPGSERSY

DLTGLKPGTEYHVHIYGVKGGEASNPLWAWFTT

ISOP120GR5P1G3
SEQ ID NO: 77
LPAPKNLVVSRVTEDSARLSWTAPDAAFDSFYIRYWEFCHSGEAIELSVPGSERSY

DLTGLKPGTEYFVRIVGVKGGRVSLPLGAKFTT

ISOP120GR5P1F5
SEQ ID NO: 78
LPAPKNLVVSRVTEDSARLSWTAPDAAFDSFEIDYWEVESEGEAIVLFVPGSERSY

DLTGLKPGTEYHVHIVGVKGGTPSYPLWADFTT

ISOP120GR5P1H6
SEQ ID NO: 79
LPAPKNLVVSRVTEDSARLSWTNEQITKYGFDSFLIQYQESEKVGEAIVLTVPGSE

RSYDLTGLKPGTEYTVSIYGVGRHYTVYDSNPLSAIFTT

ISOP120GR5P1E7
SEQ ID NO: 80
LPAPKNLVVSRVTEDSARLSWTAPDAAFDSFEIDYWEVESEGEAIILFVPGSERSY

DLTGLKPGTEYHVHIVGVKGGTPSYPLWADFTT

ISOP120GR5P1A10
SEQ ID NO: 81
LPAPKNLVVSRVTEDSARLSWTAPDAAFDSFEIPYIEVETIGEAIWLHVPGSERSYD

LTGLKPGTEYSVGINGVKGGHTSNPLSARFTT

ISOP120GR5P1C10
SEQ ID NO: 82
LPAPKNLVVSRVTEDSARLSWTAPDGAFDSFEIPYIEVETIGEAIWLHVPGSERSYD

LTGLKPGTEYSVGINGVKGGHTSNPLSARFTT

ISOP120GR5P1A11
SEQ ID NO: 83
LPAPKNLVVSRVTEDSARLSWTAPDAAFDSFGIPYWEWTTEGEAIQLIVPGSERSY

DLTGLKPATEYHVHIVGVKGGSFSEPLPADFTT

ISOP120GR5P1B11
SEQ ID NO: 84
LPAPKNLVVSRVTEDSARLSWTAPDAAFDSFNIKYWEANLYGEAIVLTVPGSERS

YGLTGLKPGTEYRVHIRGVKGGINSFPLVAVFTT

ISOP120GR5P1H11
SEQ ID NO: 85
LPAPKNLVVSRVTEDSARLSWTAPDAAFDSFYIAYWEYWGNGEAIGLIVPGSERS

YDLTGLKPGTEYHVHIVGVKGGAGSVPLWANFTT

ISOP120HR5P1E2
SEQ ID NO: 86
LPAPKNLVVSHVTEDSARLSWTAPDAAFDSFEIYYLEGGRGEAIVLTVPGSERSYD

LTVLKPGTEYLGTIYGVKCGWASNPLSAIFTT

ISOP120HR5P1A3
SEQ ID NO: 87
LPAPKNLVVSRVTEDSARLSWTAPDAAFDSFEIYYAEFGYYGEAIVLTVPGSERSY

DLTGLKPGTEYTVTIYGVKGGWYSTPLSAIFTT

ISOP120HR5P1B4
SEQ ID NO: 88
LPAPKNLVVSRVTEDSARLSWTAPDAAFDSFSIYYGEYYNLGEAIVLTVPGSERSY

DLTGLKPGTEYVVTIYGVKGGGYSNPLSAIFTT

ISOP120HR5P1G4
SEQ ID NO: 89
LPAPKNLVVSRVTEDSARLSWTAPDAAFDSFEIYYREYWYSGEAIVLTVPGSERSY

DLTGLKPGTEYLVTIYGVKGGWYSDPLSAIFTT

ISOP120HR5P1H4
SEQ ID NO: 90
LPAPKNLVVSRVTEDSARLSWTAPDAAFDSFDILYLEPYQEGEAIVLTVPGSERSY

DLTGLKPGTEYLVTIYGVKGGYYSLPLSAIFTT

ISOP120HR5P1B5
SEQ ID NO: 91
LPAPKNLVVSRVTEDSARLSWTAPDAAFDSFIIRYIEEGYYGEAIVLTVPGSERSYD

LTGLKPGTEYHVGIEGVKGGYYSYPLSAIFTT

ISOP120HR5P1A6
SEQ ID NO: 92
LPAPKNLVVSRVTEDSARLSWTAPDGAFDSFEIYYLEGGRGEAIVLTVPGSERSYD

LTGLKPGTEYLVTIYGIKCGWASNPLSAIFTT

ISOP120HR5P1G6
SEQ ID NO: 93
LPAPKNLVVSRVTEDSARLSWTAPDAAFDSFEIYYFELRLGGEAIVLTVPGSERSY

DLTGLKPGTEYLVTIYGVKGGLDSQPLSAIFTT

ISOP120HR5P1A7
SEQ ID NO: 94
LPAPKNLVVSRVTEDSARLSWTAPDAAFDSFEIYYAEPRYYGEAIVLTVPGSERSY

DLTGLKPGTEYTVTIYGVKGGYYSSPLSAIFTT

ISOP120HR5P1D7
SEQ ID NO: 95
LPAPKNLVVSRVTEDSARLSWTAPDAAFDSFDIYYLESWTRGEAIVLTVPGSERSY

DLTGLKPGTEYLVTIYGVKGGSYSRPLSAIFTT

ISOP120HR5P1E7
SEQ ID NO: 96
LPAPKNLVVSRVTEDSARLSWTAPDAAFDSFQIYYLEQLGYGEAIVLTVPGSERSY

DLTGLKPGTEYLVTIYGVKVCEQSYPLSAIFTT

ISOP120HR5P1H7
SEQ ID NO: 97
LPAPKNLVVSRVTEDSARLSWTAPDAAFDSFDIYYGEPGNLGEAIVLTVPGSERSY

DLTGLKPGTEYLVTIYGVKGGDYSSPLSAIFTT

ISOP120HR5P1H8
SEQ ID NO: 98
LPAPKNLVVSRVTEDSARLSWTAPDAAFDSFDIYYYELRLGGEAIVLTVPGSERSY

DLTGLKPGTEYLVTIYGVKGGYYSGPLSAIFTT

ISOP120HR5P1D9
SEQ ID NO: 99
LPAPKNLVVSRVTEDSARLSWTAPDAAFDSFDIYYRELDFQGEAIVLTVPGSERSY

DLTGLKPGTEYLVIIYGVKGGSYSYTLSAIFTT

ISOP120HR5P1F9
SEQ ID NO: 100
LPAPKNLVVSRVTEDSARLSWTAPDAAFDSFYIYYREHWTIGEAIVLTVPGSERSY

DLTGLKPGTEYLVTIYGVKGGAYSNPLSAIFTT

ISOP120ER5P1B4
SEQ ID NO: 101
LPAPKNLVVSRVTEDSARLSWTAPDAAFDSFSILYGEPPALGEAIVLTVPGSERSY

DLTGLKPGTEYWVTIYGVKGGVFSHPLSAIFTT

ISOP120ER5P1F4
SEQ ID NO: 102

LPAPKNLVVSRVTEDSARLSWTAPDAAFDSFVIRYIEDTVMGEAIVLTVPGSERSY

DLTGLKPGTEYHVSIEGVKGGPSSLPLSAIFTT

ISOP120ER5P1H4
SEQ ID NO: 103
LPAPKNLVVSRVTEDSARLSWTAPDAAFDSFNIMYLEDVQCGEAIVLTVPGSERS

YDLTGLKPGTEYHVGINGVKGGLRSFPLSAIFTT

ISOP120ER5P1E5
SEQ ID NO: 104
LPAPKNLVVSRVTEDSARLSWTAPDAAFDSFRISYLEDVYYGEAIVLTVPGSERSY

DLTGLKPGTEYHVGIHGVKGGIDSFPLSAIFTT

ISOP120ER5P1B6
SEQ ID NO: 105
LPAPKNLVVSRVTEDSARLSWTAPDAAFDSFDIYYGEHWKLGEAIVLTVQGSERS

YDLTGLKPGTEYLVTIYGVKGGQWSFPLSAIFTT

ISOP120ER5P1C6
SEQ ID NO: 106
LPAPKNLVVSRVTEDSARLSWTAPDAAFDSFSIYYGEWHALGEAIVLTVPGSERSY

DLTGLKPGTEYVVTIYGVKGGTYSLPLSAISTT

ISOP120ER5P1H6
SEQ ID NO: 107
LPAPKNLVVSRVTEDSARLSWTAPDAAFDSFSIYYGEWHALGEAIVLTVPGSERSY

DLTGLKPGTEYVVTIYGVKGGTYSLPLSAIFTT

ISOP120ER5P1A7
SEQ ID NO: 108
LPAPKNLVVSRVTEDSARLSWTAPDAAFDSFNIGYYERIIPGEAIVLTVPGSERSYD

LTGLKPGTEYSVLICGVKGGKGSIPLSAIFTT

ISOP120ER5P1A8
SEQ ID NO: 109
LPAPKNLVVSRVTEDSARLSWTAPDAAFDSFDIYYFEHPVGGEAIVLTVPGSERSY

DLTGLKPGTEYLVTIYGVKGGYLSMPLSAIFTT

ISOP120ER5P1E10
SEQ ID NO: 110
LPAPKNLVVSRVTEDSARLSWTAPDAAFDSFEIYYMEDFHSGEAIVLTVPGSERSY

DLTGLKPGTEYWVTIYGVEGGTGSLPLSAIFTT

ISOP120ER5P1A11
SEQ ID NO: 111
LPAPKNLVVSRVTEDSARLSWTAPDAAFDSFEIYYKELRAEGEAIVLTVPGSERSY

DLTGLKPGTEYLVTIYGVKGGSVSIPLSAIFTT

ISOP120ER5P1B12
SEQ ID NO: 112
LPAPKNLVVSRVTEDSARLSWTAPDAAFDSFAIYYIEWTAYGEAIVLTVPGSERSY

DLTGLKPGTEYVVRISGVKCGIVSFPLSAIFTT

ISOP120FR5P1F1
SEQ ID NO: 113
LPAPKNLVVSRVTEDSARLSWTAPDAAFDSFTIYYFENENGGEAIVLTVPGSERSY

DLTGLKPGTEYLVTIYGVKGCDWSDPLSAIFTT

ISOP120FR5P1C2
SEQ ID NO: 114
LPAPKNLVVSRVTEDSARLSWTAPDAAFDSFDINYFEQPKGGEAIVLTVPGSERSY

DLTGLKPGTEYLVTIYGVKGGPYSPPLSAIFTT

ISOP120FR5P1H5
SEQ ID NO: 115
LPAPKNLVVSRVTEDSARLSWTAPDAAFDSLQIYYFEWVVGGEAIVLTVPGSERS

YDLTGLKLGTEYLVTIYGVKGGNFSDPLSAIFTT

ISOP120FR5P1A6
SEQ ID NO: 116
LPAPKNLVVSRVTEDSARLSWTAPDAAFDSFIIRYLEDISYGEAIVLTVPGSERSYD

LTGLKPGTEYHVGIEGVKGGNVSFPLSAIFTT

ISOP120FR5P1H6
SEQ ID NO: 117
LPAPKNLVVSRVTEDSARLSWTAPDAAFDSFGIPYLEDIEVGEAIVLTVPGSERSYD

LAGLKPGTEYHVGIYGVKGGEQSFPLSAIFTT

ISOP120FR5P1D7
SEQ ID NO: 118
LPAPKNLVVSRVTEDSARLSWTAPDAAFDSFIIRYLEDISYGEAIVLTVPGSERSYD

LTGLKPGTEYHVGIEGVKGGNVSWPLSAIFTT

ISOP120FR5P1F8
SEQ ID NO: 119
LPAPKNLVVSRVTEDSARLSWTAPDAAFDSFIIRYLEDISYGEAIVLTVPGSERSYD

LTGLKPGTEYHVGIEGVKGGNVSWPLSAIFTT

ISOP120FR5P1E9
SEQ ID NO: 120
LPAPKNLVVSRVTEDSARLSWTAPDAAFDSFIIYYPEYISNGEAIVLTVPGSERSYD

LTGLKPGTEYHVTIGVKGGHSWPLSAIFTT

ISOP120FR5P1E10
SEQ ID NO: 121
LPAPKNLVVSRVTEDSARLSWTAPDAAFDSFLIHYTEQPSKGEAIVLTVPGSERSY

DLTGLKPGTEYQVPIGVKGGTQSCPLSAIFTT

ISOP120FR5P1A11
SEQ ID NO: 122
LPAPKNLVVSRVTEDSARLSWTAPDAAFDSFTIYYFENENGGEAIVLTVPGSERSY

DLTGLKPGTEYLVTIYGVKGGHWSRPLSAIFTT

ISOP193AR9P1A11
SEQ ID NO: 123
LPAPKNLVVSRVTEDSARLSWALSSVHAYFDSFLIQYQESEKVGEAIVLTVPGSER

SYDLTGLKPGTEYTVSIYGVQYVDGFFKSNPLSAIFTT

ISOP193AR9P1A6
SEQ ID NO: 124
LPAPKNLVVSRVTEDSARLSWKFGEVAFDSFLIQYQESEKVGEAIVLTVPGSERSY

DLTGLKPGTEYTVSIYGVGRHYTVYDSNPLSAIFTT

ISOP193AR9P1B10
SEQ ID NO: 125
LPAPKNLVVSRVTEDSARLSWAFQWHIFDSFLIQYQESEKVGEAIVLTVPGSERSY

DLTGLKPGTEYTVSIYGVGRHYTVYDSNPLSAIFTT

ISOP193AR9P1B12
SEQ ID NO: 126
LPAPKNLVVSRVTEDSARLSWTNEQITKYGFDSFLIQYQESEKVGEAIVLTVPGSE

RSYDLTGLKPGTEYTVSIYGVGAPYTVYDSNPLSAIFTT

-continued

ISOP193AR9P1B4
SEQ ID NO: 127
LPAPKNLVVSRVTEDSARLSWRDLQYHTFDSFLIQYQESEKVGEAIVLTVPGSERS

YDLTGLKPGTEYTVSIYGVGRHYTVYDSNPLSAIFTT

ISOP193AR9P1C10
SEQ ID NO: 128
LPAPKNLVVSRVTEDSARLSWPNHISIFDSFLIQYQESEKVGEAIVLTVPGSERSYD

LTGLKPGTEYTVSIYGVGRFYTVFDSNPLSAIFTT

ISOP193AR9P1E6
SEQ ID NO: 129
LPAPKNLVVSRVTEDSARLSWKFHSPTFDSFLIQYQESEKVGEAIVLTVPGSERSY

DLTGLKPGTEYTVSIYGVGRHYTVYDSNPLSAIVTT

ISOP193AR9P1F4
SEQ ID NO: 130
LPAPKNLVVSRVTEDSARLSWLEQEQFVNHFDSFLIQYQESEKVGEAIVLTVPGSE

RSYDLTGLKPGTEYTVSIYGVQYVDGFFKSNPLSAIFTT

ISOP193AR9P1F9
SEQ ID NO: 131
LPAPKNLVVSRVTEDSARLSWPLFASDLNIFDSFLIQYQESEKVGEAIVLTVPGSER

SYDLTGLKPGTEYTVSIYGVGRHYTVYDSNPLSAIFTT

ISOP193AR9P1G11
SEQ ID NO: 132
LPAPKNLVVSRVTEDSARLSWTNEQITKYGFDSFLIQYQESEKVGEAIVLTVPGSE

RSYDLTGLKPGTEYTVSIYGVGRHYTVYDSNPLSAIFTT

ISOP193AR9P1G5
SEQ ID NO: 133
LPAPKNLVVSRVTEDSARLSWRISDRLPLFDSFLIQYQESEKVGEAIVLTVPGSERS

YDLTGLKPGTEYTVSIYGVGRHYTVYDSNPLSAIFTT

ISOP193AR9P1G8
SEQ ID NO: 134
LPAPKNLVVSRVTEDSARLSWHATFGDPFDSFLIQYQESEKVGEAIVLTVPGSERS

YDLTGLKPGTEYTVSIYGVGRHYTVYDSNPLSAIFTT

ISOP193AR9P1H8
SEQ ID NO: 135
LPAPKNLVVSRVTEDSARLSWTNEQITKYGFDSFLIQYQESEKVGEAIVLTVPGSE

RSYDLTGLKPGTEYTVSIYGVGRFYTVFDSNPLSAIFTT

ISOP193BR9P1B10
SEQ ID NO: 136
LPAPKNLVVSRVTEDSARLSWAWNRHDFDSFLIQYQESEKVGEAIVLTVPGSERS

YDLTGLKPGTEYTVSIYGVHWTVLRPFIDSNPLSAIFTT

ISOP193BR9P1B12
SEQ ID NO: 137
LPAPKNLVVSRVTEDSARLSWPDESRPVRFDSFLIQYQESEKVGEAIVLTVPGSERS

YDLTGLKPGTEYTVSIYGVLRPWIYATNDSNPLSAIFTT

ISOP193BR9P1E6
SEQ ID NO: 138
LPAPKNLVVSRVTEDSARLSWGAITALFDSFLIQYQESEKVGEAIVLTVPGSERSY

DLTGLKPGTEYTVSIYGVKFPYYYATADSNPLSAIFTT

ISOP193BR9P1G11
SEQ ID NO: 139
LPAPKNLVVSRVTEDSARLSWAGHYRKIRNFDSFLIQYQESEKVGEAIVLTVPGSE

RSYDLTGLKPGTEYTVSIYGVKFPYYYATADSNPLSAIFTT

ISOP193BR9P1G2
SEQ ID NO: 140
LPAPKNLVVSRVTEDSARLSWAGHYRKIRNFDSFLIQYQESEKVGEAIVLTVPGSE

RSYDLTGLKPGTEYTVSIYGVAEHWYYATQDSNPLSAIFTT

ISOP193BR9P1G3
SEQ ID NO: 141
LPAPKNLVVSRVTEDSARLSWAQSNQQFDSFLIQYQESEKVGEAIVLTVPGSERSY

DLTGLKPGTEYTVSIYGVVWQNWVAYNSNPLSAIFTT

ISOP193BR9P1G6
SEQ ID NO: 142
LPAPKNLVVSRVTEDSARLSWDDQFEDWFDSFLIQYQESEQVGEAIVLTVPGSERS

YDLTGLKPGTEYTVSIYGVHTRDWTAWNASNPLSAIFTT

ISOP193BR9P1G9
SEQ ID NO: 143
LPAPKNLVVSRVTEDSARLSWKQVTVAPEFDSFLIQYQESEKVGEAIVLTVPGSER

SYDLTGLKPGTEYTVSIYGVKFPYYYATADSNPLSAIFTT

ISOP193BR9P1H2
SEQ ID NO: 144
LPAPKNLVVSRVTEDSARLSWPDESRPVRFDSFLIQYQESEKVGEAIVLTVPGSERS

YDLTGLKPGTEYTVSIYGVHTRDWTAWNASNPLSAIFTT

ISOP193BR9P1H3
SEQ ID NO: 145
LPAPKNLVVSRVTEDSARLSWNRLDSEWVAFDSFLIQYQESEKVGEAIVLTVPGSE

RSYDLTGLKPGTEYTVSIYGVVFRPWLAYNSNPLSAIFTT

ISOP193BR9P1H6
SEQ ID NO: 146
LPAPKNLVVSRVTEDSARLSWPDESRPVRFDSFLIQYQESEKVGEAIVLTVPGSERS

YDLTGLKPGTEYTVSIYGVVGQWKYATADSNPLSAIFTT

ISOP193ER9P1A10
SEQ ID NO: 147
LPAPKNLVVSRVTEDSARLSWTAPDAAFDSFDIYYFEHPVGGEAIVLTVPGSERSY

DLTGLKPGTEYLVTIYGVKGGHFSGPLSAIFTT

ISOP193ER9P1A11
SEQ ID NO: 148
LPAPKNLVVSRVTEDSARLSWTAPDAAFDSFAIQYQEYVAHGEAIVLTVPGSERS

YDLTGLKPGTEYHVRISGVKGGGVSWPLSAIFTT

ISOP193ER9P1A3
SEQ ID NO: 149
LPAPKNLVVSRVTEDSARLSWTTPDAAFDSFDIYYFEHPVGGEAIVLTVPGSERSY

DLTGLKPGTEYLVTIYGVKGGYLSKPLSAIFTT

ISOP193ER9P1A4
SEQ ID NO: 150
LPAPKNLIVSRVTEDSARLSWTAPDAAFDSFEIYYKELRAEGEAIVLTVPGSERSYD

LTGLKPGTEYLVTIYGVKGGSVSIPLSAIFTT

ISOP193ER9P1A8
SEQ ID NO: 151
LPAPKNLVVSRVTEDSARLSWTAPDAAFDSLDIYYFEHPVGGEAIVLTVPGSERSY

DLTGLKPGTEYLVTIYGVKGGYLSMPLSAIFTT

ISOP193ER9P1B4
SEQ ID NO: 152
LPAPKNLVVSHVTEDSARLSWTAPDAAFDSFDIYYFEHPVGGEAIVLTVPGSERSY

DLTGLKPGTEYLVTIYGVKGGYLSMPLSAIFTT

ISOP193ER9P1B5
SEQ ID NO: 153
LPAPKNLVVSRVTEDSARLSWTAPDAAFDSFAIQYQEYVAHGEAIVLTVPGSERS

YDLTGLKPGTEYHVRISGVKGGGVSWPLSAIVTT

ISOP193ER9P1C10
SEQ ID NO: 154
LLAPKNLVVSRVTEDSARLSWIAPDAAFDSFEIYYKELRAEGEAIVLTVPGSERSY

DLTGLKPGTEYLVTIYGVKGGSVSIPLSAIFTT

ISOP193ER9P1C4
SEQ ID NO: 155
LPAPKNLVVSRVTEDSARLSWTAPDAAFDSFDIYYFEHPVGGEAIVLTVPGSERSY

DLTGLKPGTEYLVTIYGVKGGIWSVPLSAIFTT

ISOP193ER9P1C8
SEQ ID NO: 156
LPAPKNLVVSRVTEDSARLSWTAPDAAFDSFDIYYFEHPVGGEAIVLTVPGSERSY

DLTGLKPGTEYLVTIYGVKGGTYSLPLSAIFTT

ISOP193ER9P1C9
SEQ ID NO: 157
LPAPKNLVVSRVTEDSARLSWTAPDAAFDSFDIYYFEHPVGGEAIVLTVPGSERSY

DLTGLKPGTEYLVTIYGVKGGELSKPLSAISTT

ISOP193ER9P1D4
SEQ ID NO: 158
LPAPKNLVVSRVTEDSARLSWTAPDAAFDSFDIYYFEHPVGGEAIVLTVPGSERSY

DLTGLKPGTEYLVTIYGVKGGTYSPPLSAIFTT

ISOP193ER9P1D7
SEQ ID NO: 159
LPAPKNLVVSRVTEDSARLSWTAPDAAFDSFDIYYGEHWKLGEAIVLTVPGSERS

YDLTGLKPGTEYLVTIYGVKGGMSSNPLSAIFTT

ISOP193ER9P1E1
SEQ ID NO: 160
LPAPKNLVVSRVTEDSARLSWTAPDAAFDSFDIYYFEHPVGGEAIVLTVPGSERSY

DLTGLKPGTEYLVTIYGVKGGSVSIPLSAIFTT

ISOP193ER9P1E2
SEQ ID NO: 161
LPAPKNLVVSRVTEDSARLSWTAPDAAFDSFDIYYFEHPVGGEAIVLTVPGSERSY

DLTGLKPGTEYLVTIYGVKGGFWSQPLSAIFTT

ISOP193ER9P1E4
SEQ ID NO: 162
LPAPKNLVVSRVTEDSARLSWTAPDAAFDSFAIIYQEYVKSGEAIVLTVPGSERSY

DLTGLKPGTEYHVRIGGVKGGLLSLPLSAIFTT

ISOP193ER9P1E8
SEQ ID NO: 163
LPAPKNLVVSRVTEDSARLSWTAPDAAFDSFDIYYFEHPVGGEAIVLTVPGSERSY

DLTGLKPGTEYLVTIYGVKGGELSKPLSAIFTT

ISOP193ER9P1F11
SEQ ID NO: 164
LPAPKNLVVSRVTEDSARLSWTAPDAAFDSFAIQYQEYVAHGEAIVLTVPGSERS

YDLTGLKPGTEYHVRISGVKGGGVSWPLSAISTT

ISOP193ER9P1F7
SEQ ID NO: 165
LPAPKNLVVSRVTEDSAHLSWTAPDAAFDSFDIYYFEHPVGGEAIVLTVPGSERSY

DLTGLKPGTEYLVTIYGVKGGYLSMPLSAIFTT

-continued

ISOP193ER9P1F9
SEQ ID NO: 166
LPAPKNLVVSRVTEDSARLSWTAPDAAFDSFHIYYGEHYNLGEAIVLTVPGSERSY

DLTGLKPGTEYLVTIYGVKGGFWSTPLSAIFTT

ISOP193ER9P1G11
SEQ ID NO: 167
LPAPKNLVVSRVTEDSARLSWTAPDAAFDSFDIYYFEHPVGGEAIVLTVPGSERSY

DLTGLKPGTEYLVTIYGVKGGYLSMPLSAIFTT

ISOP193ER9P1G2
SEQ ID NO: 168
LPAPKNLVVSRVTEDSARLSWTAPDAAFDSFDIYYFEQPVGGEAIVLTVPGSERSY

DLTGLKPGTEYLVTIYGVKGGYLSMPLSAIFTT

ISOP193ER9P1G4
SEQ ID NO: 169
LPAPKNLVVSRVTEDSARLSWTAPDAAFDSFDIYYFEHPVGGEAIVLTVPGSERSY

DLTGLKPGTEYLVTIYGVKGGNFSFPLSAIFTT

ISOP193ER9P1G5
SEQ ID NO: 170
LPAPKNLVVSRVTEDSARLSWTAPDAAFDSFDIYYFEHPVGGEAIVLTVPGSERSY

DLTGLKPGTEYLVTIYGVKGGYLSMPLSAIFTT

ISOP193ER9P1G9
SEQ ID NO: 171
LPAPKNLVVSRVTEDSARLSWTAPDAAFDSFDIYYFEHPVGGEAIVLTVPGSERSY

DLTGLKPGTEYLVTIYGVKGGNGSSPLSAIFTT

ISOP193ER9P1H11
SEQ ID NO: 172
LPAPKNLVVSRVTEDSARLSWTAPDAAFDSFDIYYFEHPVGGEAIVLTVPGSERSY

DLTGLKPGTEYLVAIYGVKGGVFSHPLSAIFTT

ISOP193ER9P1H2
SEQ ID NO: 173
LPAPKNLVVSRVTEDSARLSWTAPDAAFDSFRISYLEDVYYGEAIVLTVPGSERSY

DLTGLKPGTEYHVGIHGVKGGIDSFPLSAIFTT

ISOP193ER9P1H3
SEQ ID NO: 174
LPAPKNLVVSRVTEDSARLSWTAPDAAFDSFEIYYLEVRNRGEAIVLTVPGSERSY

DLTGLKPGTEYHVGIAGVKGGFHSFPLSAIFTT

ISOP193FR9P1A11
SEQ ID NO: 175
LPAPKNLVVSRVTEDSARLSWTAPDAAFDSFAIQYWEGWEWGEAIVLTVPGSERS

YDLTGLKPGTEYLVTIYGVKGGHWSRPLSAIFTT

ISOP193FR9P1A5
SEQ ID NO: 176
LPAPKNLVVSRVTEDSARLSWTAPDAAFDSFEIYYIEPIAPGEAIVLTVPGSERSYD

LTGLKPGTEYWVTIYGVKGCDWSDPLSAIFTT

ISOP193FR9P1C1
SEQ ID NO: 177
LPAPKNLVVSRVTEDSARLSWTAPDAAFDSFEIYYFENENGGEAIVLTVPGSERSY

DLTGLKPGTEYLVTIYGVKGCDWSDPLSAIFTT

ISOP193FR9P1C5
SEQ ID NO: 178
LPAPKNLVVSRVTEDSARLSWTAPDAAFDSFHIYYLEQYSRGEAIVLTVPGSERSY

DLTGLKPGTEYLVTIYGVKGCDWSDPLSAIFTT

-continued

ISOP193FR9P1C9
SEQ ID NO: 179
LPAPKNLVVSRVTEDSARLSWTAPDAAFDSFQIYYFEWVVGGEAIVLTVPGSERS

YDLTGLKPGTEYLVTIYGVKGCDWSDPLSAIFTT

ISOP193FR9P1D1
SEQ ID NO: 180
LPAPKNLVVSRVTEDSARLSWTAPDAAFDSFFIQYLEDVTNGEAIVLTVPGSERSY

DLTGLKPGTEYRVPIAGVKGGRDSQPLSAIFTT

ISOP193FR9P1D5
SEQ ID NO: 181
LPAPKNLVVSRVTEDSARLSWTAPDAAFDSFYIRYIEDVDFGEAIVLTVPGSERSY

DLTGLKPGTEYLVTIYGVKGCDWSDPLSAIFTT

ISOP193FR9P1D7
SEQ ID NO: 182
LPAPKNLVVSRVTEDSARLSWTAPDAAFDSFEIYYAEYFKNGEAIVLTVPGSERSY

DLTGLKPGTEYLVTIYGVKGCDWSDPLSAISTT

ISOP193FR9P1E1
SEQ ID NO: 183
LPAPKNLVVSRVTEDSARLSWTAPDAAFDSFIIRYLEDISYGEAIVLTVPGSERSYD

LTGLKPGTEYHVGIEGVKGGNVSWPLSAIFTT

ISOP193FR9P1E10
SEQ ID NO: 184
LPAPKNLVVSRVTEDSARLSWTTPDAAFDSFHIHYLEGEWGGEAIVLTVPGSERSY

DLTGLKPGTEYLVTIYGVKGCDWSDPLSAIFTT

ISOP193FR9P1F8
SEQ ID NO: 185
LPAPKNLVVSRVTEDSARLSWTAPDAAFDSFDINYFENELGGEAIVLTVPGSERSY

DLTGLKPGTEYLVTIYGVKGCDWSDPLSAIFTT

ISOP193FR9P1G10
SEQ ID NO: 186
LPAPKNLVVSRVTEDSARLSWTAPDAAFDSFTIYYFENENGGEAIVLTVPGSERSY

DLTGLKPGTEYLVTIYGVKGGHWSRPLSAIFTT

ISOP193FR9P1G11
SEQ ID NO: 187
LPAPKNLVVSRVTEDSARLSWTAPDAAFDSFTIYYFENENGGEAIVLTVPGSERSY

DLTGLKPGTEYLVTIYGVKGCDWSDPLSAIFTT

ISOP193FR9P1G2
SEQ ID NO: 188
LPAPKNLVVSRVTEDSARLSWTAPDAAFDSFTIYYFENENGGEAIVLTVPGSERSY

DLTGLKPDTEYLVTIYGVKGGHWSRPLSAIFTT

ISOP193FR9P1G4
SEQ ID NO: 189
LPAPKNLVVSRVTEDSARLSWTAPDAAFDSFEIYYFENLGGEAIVLTVPGSERSY

DLTGLKPGTEYLVTIYGVKGGDWSDPLSAIFTT

ISOP193FR9P1G7
SEQ ID NO: 190
LPAPKNLVVSRVTEDSARLSWTAPDAAFDSFHIHYLEGEWGGEAIVLTVPGSERS

YDLTGLKPGTEYLVTIYGVKGCDWSDPLSAIFTT

ISOP193FR9P1G8
SEQ ID NO: 191
LPAPKNLVVSRVTEDSARLSWTAPDAAFDSFEIYYFENELGGEAIVLTVPGSERSY

DLTGLKPGTEYLVTIYGVKGCDWSDPLSAIFTT

ISOP193FR9P1G9
SEQ ID NO: 192
LPAPKNLFVSRVTEDSARLSWTAPDAAFDSFQIYYREQWWDGEAIVLTVPGSERS

YDLTGLKPGTEYLVTIYGVKGCDWSDPLSAIFTT

ISOP193FR9P1H6
SEQ ID NO: 193
LPAPKNLVVSRVTEDSARLSWTAPDAAFDSFDINYFEQPKGGEAIVLTVPGSERSY

DLTGLKPGTEYLVTIYGVKGCDWSDPLSAIFTT

ISOP193FR9P1H9
SEQ ID NO: 194
LPAPKNLVVSRVTEDSARLSWTAPDAAFDSFEIYYDELRNPGEAIVLTVPGSERSY

DLTGLKPGTEYAVTIYGVKGGRYSPPLSAIFTT

ISOP193GR9P1A7
SEQ ID NO: 195
LPAPKNLVVSRVTEDSARLSWTAPDAAFDSFAIFYHEFANPGEAIDLPVPGSERSY

DLTGLKPGTEYDVRIYGVKGGTASIPLDAEFTT

ISOP193GR9P1B3
SEQ ID NO: 196
LPAPKNLVVSRVTEDSARLSWTAPDAAFDSFAIGYVEWTANGEAIVLIVPGSERSY

DLTGLKPGTEYVVRIRGGVKGGDSSFPLRADFTT

ISOP193GR9P1E10
SEQ ID NO: 197
LPAPKNLVVSRVTEDSARLSWTAPDAAFDSFAISYTESIRQGEAIWLWVPGSERSY

DLTGLKPGTEYEVTIGGVKGGIRSYPLWAWFTT

ISOP193GR9P1F6
SEQ ID NO: 198
LPAPKNLVVSRVTEDSARLSWTAPDAAFDSFEIDYWEVESEGEAIVLFVPGSERSY

DLTGLKPGTEYHVHIVGVKGGTPSYPLWADFTT

ISOP193GR9P1F7
SEQ ID NO: 199
LPAPKNLVVSRVTEDSARLSWTAPDAAFDSFDIPYVEYYPSGEAIVLNVPGSERSY

DLTGLKPGTEYGVTIWGIKGGNESVPLTARFTT

ISOP193GR9P1G9
SEQ ID NO: 200
LPAPKNLVVSRVTEDSARLSWTAPDAAFDSFAIFYHEFANSGEAIDLPVPGSERSY

DLTGLKPGTEYDVRIYGVKGGTASIPLDAEFTT

ISOP193GR9P1H2
SEQ ID NO: 201
LPAPKNLVVSRVTEDSARLSWTAPDAAFDSFEIPYIEVETIGEAIWLHVPGSERSYD

LTGLKPGTEYSVGINGVKGGHTSNPLSARFTT

ISOP193HR9P1A10
SEQ ID NO: 202
LPAPKNLVVSRVTEDSARLSWTAPDAAFDSFDIYYLEPWGGGEAIVLTVPGSERSY

DLTGLKPGTEYWVTIYGVKVCLGSNPLSAIFTT

ISOP193HR9P1A11
SEQ ID NO: 203
LPAPKNLVVSRVTEDSARLSWTAPDAAFDSFEIYYLEGGRGEAIVLTVPGSERSYD

LTGLKPGTEYLVTIYGVKCGWASNPLSAIFTT

ISOP193HR9P1A5
SEQ ID NO: 204
LPAPKNLVVSRVTEDSARLSWTAPDAAFDSFDIYYYELRLGGEAIVLTVPGSERSY

DLTGLKPGTEYLVTIYGVKGCGYSAPLSAIVTT

```
ISOP193HR9P1A6
SEQ ID NO: 205
LPAPKNLVVSRVTEDSARLSWTAPDAAFDSFDIYYYELRLGGEAIVLTVPGSERSY

DLTGLKPGTEYLVSIYGVKGCYSDPLSAIFTT

ISOP193HR9P1A7
SEQ ID NO: 206
LPAPKNLVVSRVTEDSARLSWTAPDAAFDSFDIYYYELRLGGEAIVLTVPGSERSY

DLTGLKPGTEYLVTIYGVKVCNASTPLSAIFTT

ISOP193HR9P1B11
SEQ ID NO: 207
LPAPKNLVVSRVTEDSARLSWTAPDAAFDSFEIYYFELRLGGEAIVLTVPGSERSY

DLTGLKPGTEYLVTIYGVKGCYSDPLSAIFTT

ISOP193HR9P1B7
SEQ ID NO: 208
LPAPKNLVVSRVTEDSARLSWTAPDAAFDSFEIYYFELRLGGEAIVLTVPGSERSY

DLTGLKPGTEYLVSIYGVKGCYSDPLSAIFTT

ISOP193HR9P1C7
SEQ ID NO: 209
LPAPKNLVVSRVTEDSARLSWTAPDAAFDSFEIYYLELDSDGEAIVLTVPGSERSY

DLTGLKPGTEYIVTIYGVKVCTGSRPLSAIFTT

ISOP193HR9P1C8
SEQ ID NO: 210
LPAPKNLVVSRVTEDSARLSWTAPDAAFDSFEIYYFELRLGGEAIVLTVPGSERSY

DLTGLKPGTEYLVTIYGVKGGGYSTPLSAIFTT

ISOP193HR9P1D11
SEQ ID NO: 211
LPAPKNLVVSRVTEDSARLSWTAPDAAFDSFDIYYYELRLGGEAIVLTVPGSERSY

DLTGLKPGTEYLVTIYGVKVCEQSYPLSAIFTT

ISOP193HR9P1D8
SEQ ID NO: 212
LPAPKNLVVSRVTEDSARLSWTAPDAAFDSFDIYYLESGRDGEAIVLTVPGSERSY

DLTGLKPGTEYLVSIYGVKGCYSDPLSAIFTT

ISOP193HR9P1E2
SEQ ID NO: 213
LPAPKNLVVSRVTEDSARLSWTAPDAAFDSFEIYYLEWCSGGEAIVLTVPGSERSY

DLTGLKPGTEYLVTIYGVKGCAASDPLSAIFTT

ISOP193HR9P1E3
SEQ ID NO: 214
LPAPKNLVVSRVTEDSARLSWTAPDAAFDSFEIYYFELRLGGEAIVLTVPGSERSY

DLTGLKPGTEYLVTIYGVKGGAYSNPLSAIFTT

ISOP193HR9P1E6
SEQ ID NO: 215
LPAPKNLVVSRVTEDSARLSWTAPDAAFDSFEIYYAEFGYYGEAIVLTVPGSERSY

DLTGLKPGTEYLVTIYGVKGCAASDPLSAIFTT

ISOP193HR9P1E8
SEQ ID NO: 216
LPAPKNLVVSRVTEDSARLSWTAPDAAFDSFDIYYYELRLGGEAIVLTVPGSERSY

DLTGLKPGTEYLVTIYGVKGGDYSPPLSAIFTT

ISOP193HR9P1F10
SEQ ID NO: 217
LPAPKNLVVSRVTEDSARLSWTAPDAAFDSFDIYYYELRLGGEAIVLTVPGSERSY

DLTGLKPGTEYLVTIYGVKGGYYSGPLSAIFTT
```

-continued

ISOP193HR9P1F8
SEQ ID NO: 218
LPAPKNLVVSRVTEDSARLSWTAPDAAFDSFDIYYYELRLGGEAIVLTVPGSERSY

DLTGLKPGTEYLVTIYGVKVCYYSTPLSAIFTT

ISOP193HR9P1G10
SEQ ID NO: 219
LPAPKNLVVSRVTEDSARLSWTAPDAAFDSFEIYYFELRLGGEAIVLTVPGSERSY

DLTGLKPGTEYLVTIYGVKGGDYSPPLSAISTT

ISOP193HR9P1G4
SEQ ID NO: 220
LPAPKNLVVSRVTEDSARLSWTAPDAAFDSFEIYYFELRLGGEAIVLTVPGSERSY

DLTGLKPGTEYLVTIYGVKGGDYSPPLSAIFTT

ISOP193HR9P1G5
SEQ ID NO: 221
LPAPKNLVVSRVTEDSARLSWTAPDAAFDSFDIYYYELRLGGEAIVLTVPGSERSY

DLTGLKPGTEYLVTIYGVKGCAASDPLSAIFTT

ISOP193HR9P1G6
SEQ ID NO: 222
LPAPKNLVVSRVTEDSARLSWTAPDAAFDSFDIYYYELRLGGEAIVLTVPGSERSY

DLTGLKPGTEYLVTIYGVKVCEQSYPLSAISTT

ISOP193HR9P1H10
SEQ ID NO: 223
LPAPKNLVVSRVTEDSARLSWTAPDAAFDSFDIYYYELRLGGEAIVLTVPGSERSY

DLTGLKPGTEYLVTIYGVKVCLGSNPLSAIFTT

ISOP193HR9P1H7
SEQ ID NO: 224
LPAPKNLVVSRVTEDSARLSWTAPDAAFDSFEIYYREPHYGGEAIVLTVPGSERSY

DLTGLKPGTEYWVTIYGVKVCLGSNPLSAIFTT

---

What is claimed is:

1. A protein comprising an amino acid sequence that is at least 90% identical to a sequence selected from the group consisting of SEQ ID NOs: 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

2. The protein of claim 1, wherein the amino acid sequence is at least 95% identical to a sequence selected from the group consisting of SEQ ID NOs: 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

3. The protein of claim 1, wherein the protein has at least one substitution at a residue selected from the group consisting of 11, 14, 17, 37, 46, 73, and 86 corresponding to SEQ ID NO: 4.

4. The protein of claim 1, wherein the protein is conjugated to a heterologous molecule.

5. The protein of claim 4, wherein the heterologous molecule is a detectable label, a cytotoxic agent, or both.

6. The protein of claim 5, wherein the cytotoxic agent is a selected from a chemotherapeutic agent, a drug, a growth inhibitory agent, a toxin, an enzymatically active toxin of bacterial origin or fragments thereof, an enzymatically active toxin of fungal origin or fragments thereof, an enzymatically active toxin of plant origin or fragments thereof, an enzymatically active toxin of animal origin or fragments thereof, or a radioactive isotope.

7. The protein of claim 5, wherein the cytotoxic agent is selected from daunomycin, doxorubicin, methotrexate, vindesine, diphtheria toxin, ricin, geldanamycin, maytansinoids or calicheamicin.

8. The protein of claim 5, wherein the cytotoxic agent is selected from diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Saponaria officinalis* inhibitor, gelonin, mitogellin, restrictocin, phenomycin, enomycin, or tricothecenes.

9. The protein of claim 5, wherein the cytotoxic agent is a radionuclide, selected from $^{212}$Bi, $^{131}$I, $^{131}$In, $^{90}$Y, or $^{186}$Re.

10. The protein of claim 5, wherein the cytotoxic agent is conjugated to the protein by a linker.

11. The protein of claim 5, wherein the cytotoxic agent is complexed with a chelating agent.

12. The protein of claim 5, wherein the detectable label is selected from a radioactive isotope, a magnetic bead, a metallic bead, a colloidal particle, a fluorescent dye, an electron-dense reagent, an enzyme, a biotin, a digoxigenin, a hapten, a luminescent molecule, a chemiluminescent molecule, a fluorochrome, a fluorophore, a fluorescent quenching agent, a colored molecule, a cintillant, an avidin, astreptavidin, a protein A, a protein G, an antibody, an antibody fragment, a polyhistidine, a Ni$^{2+}$, a flag tag, a myc tag, a heavy metal, an alkaline phosphatase, a peroxidase, a luciferase, an electron donor, an electron acceptor, an acridinium ester, or a colorimetric substrate.

13. The protein of claim 5, wherein the detectable label is auristatin, monomethyl auristatin phenylalanine, dolostatin, chemotherapeutic agent, a drug, a growth inhibitory agent, a toxin, or a radioactive isotope.

14. The protein of claim 5, wherein the detectable label is conjugated to the protein by a linker.

15. The protein of claim 5, wherein the detectable label is complexed with a chelating agent.

16. The protein of claim 1, further comprising a methionine at the N-terminus of the protein.

17. The protein of claim 1, wherein the protein is coupled to a half-life extending moiety.

18. The protein of claim 17, wherein the half-life extending moiety is an albumin binding molecule, a polyethylene glycol (PEG), albumin, albumin variant, or at least a portion of an Fc region of an immunoglobulin.

19. A composition comprising the protein of claim 1 and a pharmaceutically acceptable carrier.

20. A kit comprising the protein of claim 1.

* * * * *

SEQUENCE LISTING

<160> NUMBER OF SEQ ID NOS: 224

<210> SEQ ID NO 1
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

```
<210> SEQ ID NO 2
<211> LENGTH: 94
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (75)..(86)
<223> OTHER INFORMATION: Any amino acid
<220> FEATURE:
<221> NAME/KEY: MISC_FEATURE
<222> LOCATION: (75)..(86)
<223> OTHER INFORMATION: This region may encompass 7-12 residues

<400> SEQUENCE: 2

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa
65                  70                  75                  80

Xaa Xaa Xaa Xaa Xaa Xaa Pro Leu Ser Ala Glu Phe Thr Thr
                85                  90

<210> SEQ ID NO 3
<211> LENGTH: 89
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (22)..(27)
<223> OTHER INFORMATION: Ala, Arg, Asn, Asp, Glu, Gln, Gly, His, Ile,
    Leu, Lys, Phe, Pro, Ser, Thr, Trp, Tyr or Val
<220> FEATURE:
<221> NAME/KEY: MOD_RES
<222> LOCATION: (28)..(28)
<223> OTHER INFORMATION: Phe, Ile, Leu, Val or Tyr
<220> FEATURE:
<221> NAME/KEY: MOD_RES
<222> LOCATION: (29)..(29)
<223> OTHER INFORMATION: Asp, Glu or Thr
<220> FEATURE:
<221> NAME/KEY: MOD_RES
<222> LOCATION: (75)..(79)
<223> OTHER INFORMATION: Ala, Arg, Asn, Asp, Glu, Gln, Gly, His, Ile,
    Leu, Lys, Phe, Pro, Ser, Thr, Trp, Tyr or Val
<220> FEATURE:
<221> NAME/KEY: MOD_RES
<222> LOCATION: (81)..(82)
<223> OTHER INFORMATION: Ala, Arg, Asn, Asp, Glu, Gln, Gly, His, Ile,
    Leu, Lys, Phe, Pro, Ser, Thr, Trp, Tyr or Val

<400> SEQUENCE: 3

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60
```

```
Thr Glu Tyr Thr Val Ser Ile Tyr Gly Val Xaa Xaa Xaa Xaa Ser
65                  70                  75                  80

Xaa Xaa Leu Ser Ala Glu Phe Thr Thr
            85
```

<210> SEQ ID NO 4
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 4

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly His Arg Ser
65                  70                  75                  80

Asn Pro Leu Ser Ala Ile Phe Thr Thr
            85
```

<210> SEQ ID NO 5
<211> LENGTH: 97
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (22)..(30)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MISC_FEATURE
<222> LOCATION: (22)..(30)
<223> OTHER INFORMATION: This region may encompass 6-9 residues
<220> FEATURE:
<221> NAME/KEY: MOD_RES
<222> LOCATION: (78)..(87)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MISC_FEATURE
<222> LOCATION: (78)..(87)
<223> OTHER INFORMATION: This region may encompass 7-9 residues

<400> SEQUENCE: 5

```
Leu Pro Ala Pro Lys Asn Leu Val Val Ser Arg Val Thr Glu Asp Ser
1               5                   10                  15

Ala Arg Leu Ser Trp Xaa Xaa Xaa Xaa Xaa Xaa Xaa Xaa Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Xaa Xaa Xaa
65                  70                  75                  80

Xaa Xaa Xaa Xaa Xaa Xaa Xaa Ser Asn Pro Leu Ser Ala Ile Phe Thr
```

```
                    85                  90                  95

Thr

<210> SEQ ID NO 6
<211> LENGTH: 96
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (75)..(86)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MOD_RES
<222> LOCATION: (75)..(86)
<223> OTHER INFORMATION: This region may encompass 7-12 residues

<400> SEQUENCE: 6

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95

<210> SEQ ID NO 7
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (34)..(34)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (36)..(36)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (38)..(41)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (68)..(68)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (70)..(70)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
```

```
<220> FEATURE:
<221> NAME/KEY: MOD_RES
<222> LOCATION: (72)..(72)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (78)..(79)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (81)..(81)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85

<210> SEQ ID NO 8
<211> LENGTH: 89
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (32)..(32)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (34)..(34)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (36)..(36)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (38)..(41)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (46)..(46)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (48)..(48)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (68)..(68)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
```

```
<221> NAME/KEY: MOD_RES
<222> LOCATION: (70)..(70)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (72)..(72)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (78)..(79)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (81)..(81)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (84)..(84)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (86)..(86)
<223> OTHER INFORMATION: Ala, Asp, Glu, Phe, Gly, His, Ile, Lys, Leu,
      Asn, Pro, Gln, Arg, Ser, Thr, Val, Tyr or Trp

<400> SEQUENCE: 8

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Xaa Leu Xaa
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Xaa Xaa Ser
65                  70                  75                  80

Xaa Pro Leu Xaa Ala Xaa Phe Thr Thr
                85

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
gtgacacggc ggttagaac                                              19

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gcctttggga agcttctaag                                             20

<210> SEQ ID NO 11
<211> LENGTH: 30
<212> TYPE: DNA
<213> ORGANISM: Artificial Sequence
```

```
<220> FEATURE:
<223> OTHER INFORMATION: Synthetic oligonucleotide

<400> SEQUENCE: 11
cggcggttag aacgcggcta caattaatac                                           30

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
catgattacg ccaagctcag aa                                                   22

<210> SEQ ID NO 13
<211> LENGTH: 385
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(224)
<223> OTHER INFORMATION: a, c, t, g, unknown or other
<220> FEATURE:
<221> NAME/KEY: misc_feature
<222> LOCATION: (198)..(224)
<223> OTHER INFORMATION: n is a, c, g, or t

<400> SEQUENCE: 13
gtgacacggc ggttagaacg cggctacaat taatacataa ccccatcccc ctgttgacaa          60
ttaatcatcg gctcgtataa tgtgtggaat tgtgagcgga taacaatttc acacaggaaa         120
caggatctac catgctgccg gcgccgaaaa acctggttgt ttctgaagtt accgaagact         180
ctctgcgtct gtcttggnnn nnnnnnnnn nnnnnnnnn nnnnttygac tctttcctga          240
tccagtacca ggaatctgaa aaagttggtg aagcgatcaa cctgaccgtt ccgggttctg         300
aacgttctta cgacctgacc ggtctgaaac cgggtaccga atacaccgtt tctatctacg         360
gtgttcttag aagcttccca aaggc                                              385

<210> SEQ ID NO 14
<211> LENGTH: 382
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(221)
<223> OTHER INFORMATION: a, c, t, g, unknown or other
<220> FEATURE:
<221> NAME/KEY: misc_feature
<222> LOCATION: (198)..(221)
<223> OTHER INFORMATION: n is a, c, g, or t

<400> SEQUENCE: 14
gtgacacggc ggttagaacg cggctacaat taatacataa ccccatcccc ctgttgacaa          60
ttaatcatcg gctcgtataa tgtgtggaat tgtgagcgga taacaatttc acacaggaaa         120
caggatctac catgctgccg gcgccgaaaa acctggttgt ttctgaagtt accgaagact         180
ctctgcgtct gtcttggnnn nnnnnnnnn nnnnnnnnn nttygactct tcctgatcc           240 agtaccagga atctgaaaaa gttggtgaag cgatcaacct gaccgttccg ggttctgaac         300
```

```
gttcttacga cctgaccggt ctgaaaccgg gtaccgaata caccgtttct atctacggtg    360
ttcttagaag cttcccaaag gc                                             382
```

<210> SEQ ID NO 15
<211> LENGTH: 379
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(218)
<223> OTHER INFORMATION: a, c, t, g, unknown or other
<220> FEATURE:
<221> NAME/KEY: misc_feature
<222> LOCATION: (198)..(218)
<223> OTHER INFORMATION: n is a, c, g, or t

<400> SEQUENCE: 15

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnn nnnnnnnntt ygactctttc ctgatccagt    240
accaggaatc tgaaaaagtt ggtgaagcga tcaacctgac cgttccgggt tctgaacgtt   300
cttacgacct gaccggtctg aaaccgggta ccgaatacac cgtttctatc tacggtgttc   360
ttagaagctt cccaaaggc                                                 379
```

<210> SEQ ID NO 16
<211> LENGTH: 376
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(215)
<223> OTHER INFORMATION: a, c, t, g, unknown or other
<220> FEATURE:
<221> NAME/KEY: misc_feature
<222> LOCATION: (198)..(215)
<223> OTHER INFORMATION: n is a, c, g, or t

<400> SEQUENCE: 16

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnn nnnnttyga ctctttcctg atccagtacc     240
aggaatctga aaaagttggt gaagcgatca acctgaccgt tccgggttct gaacgttctt   300
acgacctgac cggtctgaaa ccgggtaccg aatacaccgt ttctatctac ggtgttctta   360
gaagcttccc aaaggc                                                    376
```

<210> SEQ ID NO 17
<211> LENGTH: 131
<212> TYPE: DNA
<213> ORGANISM: Artificial Sequence
<220> FEATURE:
<223> OTHER INFORMATION: Synthetic polynucleotide

<400> SEQUENCE: 17

```
cggcggttag aacgcggcta caattaatac ataaccccat ccccctgttg acaattaatc    60
```

```
atcggctcgt ataatgtgtg gaattgtgag cggataacaa tttcacacag gaaacaggat    120
ctaccatgct g                                                         131

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 18
cggcggttag aacgcggcta caattaatac                                     30

<210> SEQ ID NO 19
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 19
ccaagacaga cgggcagagt cttcggtaac gcgagaaaca accaggtttt tcggcgccgg    60
cagcatggta gatcctgttt c                                              81

<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 20
ccgaagactc tgcccgtctg tcttgg                                         26

<210> SEQ ID NO 21
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 21
cagtggtctc acggattcct ggtactggat caggaaagag tcgaa                    45

<210> SEQ ID NO 22
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 22
catgcggtct cttccgaaaa agttggtgaa gcgatcgtcc tgaccgttcc gggt          54

<210> SEQ ID NO 23
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 23
ggtggtgaag atcgcagaca gcgggttag                                      29
```

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
cggcggttag aacgcggcta c                                          21

<210> SEQ ID NO 25
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 25
aagatcagtt gcggccgcta gactagaacc gctgccaccg ccggtggtga agatcgcaga    60
c                                                                  61

<210> SEQ ID NO 26
<211> LENGTH: 485
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(392)
<223> OTHER INFORMATION: a, c, t, g, unknown or other
<220> FEATURE:
<221> NAME/KEY: misc_feature
<222> LOCATION: (357)..(392)
<223> OTHER INFORMATION: n is a, c, g, or t

<400> SEQUENCE: 26
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360 nnnnnnnnn nnnnnnnnnn nnnnnnnnnn nntctaaccc gctgtctgcg atcttcacca   420
ccggcggtca ccatcaccat caccatggca gcggttctag tctagcggcc gcaactgatc   480
ttggc                                                              485

<210> SEQ ID NO 27
<211> LENGTH: 482
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(389)
<223> OTHER INFORMATION: a, c, t, g, unknown or other
<220> FEATURE:
<221> NAME/KEY: misc_feature
<222> LOCATION: (357)..(389)
<223> OTHER INFORMATION: n is a, c, g, or t

<400> SEQUENCE: 27

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnnnnnnnnt ctaacccgct gtctgcgatc ttcaccaccg     420
gcggtcacca tcaccatcac catggcagcg gttctagtct agcggccgca actgatcttg     480
gc                                                                    482
```

<210> SEQ ID NO 28
<211> LENGTH: 479
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(386)
<223> OTHER INFORMATION: a, c, t, g, unknown or other
<220> FEATURE:
<221> NAME/KEY: misc_feature
<222> LOCATION: (357)..(386)
<223> OTHER INFORMATION: n is a, c, g, or t

<400> SEQUENCE: 28

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnnnnntcta acccgctgtc tgcgatcttc accaccggcg     420
gtcaccatca ccatcaccat ggcagcggtt ctagtctagc ggccgcaact gatcttggc     479
```

<210> SEQ ID NO 29
<211> LENGTH: 476
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(383)
<223> OTHER INFORMATION: a, c, t, g, unknown or other
<220> FEATURE:
<221> NAME/KEY: misc_feature
<222> LOCATION: (357)..(383)
<223> OTHER INFORMATION: n is a, c, g, or t

<400> SEQUENCE: 29

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
```

```
aggaatctga aaaagttggt gaagcgatcg tgctgaccgt tccgggttct gaacgttctt       300
acgacctgac cggtctgaaa ccgggtaccg aatacaccgt ttctatctac ggtgttnnnn       360
nnnnnnnnnn nnnnnnnnnn nnntctaacc cgctgtctgc gatcttcacc accggcggtc       420
accatcacca tcaccatggc agcggttcta gtctagcggc cgcaactgat cttggc          476
```

<210> SEQ ID NO 30
<211> LENGTH: 473
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(380)
<223> OTHER INFORMATION: a, c, t, g, unknown or other
<220> FEATURE:
<221> NAME/KEY: misc_feature
<222> LOCATION: (357)..(380)
<223> OTHER INFORMATION: n is a, c, g, or t

<400> SEQUENCE: 30

```
gtgacacggc ggttagaacg cggctacaat taatacataa ccccatcccc ctgttgacaa        60
ttaatcatcg gctcgtataa tgtgtggaat tgtgagcgga taacaatttc acacaggaaa       120
caggatctac catgctgccg gcgccgaaaa acctggttgt ttctcgcgtt accgaagact       180
ctgcgcgtct gtcttggacc gcgccggacg cggcgttcga ctctttcctg atccagtacc       240
aggaatctga aaaagttggt gaagcgatcg tgctgaccgt tccgggttct gaacgttctt       300
acgacctgac cggtctgaaa ccgggtaccg aatacaccgt ttctatctac ggtgttnnnn       360
nnnnnnnnnn nnnnnnnnnn tctaacccgc tgtctgcgat cttcaccacc ggcggtcacc       420
atcaccatca ccatggcagc ggttctagtc tagcggccgc aactgatctt ggc             473
```

<210> SEQ ID NO 31
<211> LENGTH: 470
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(377)
<223> OTHER INFORMATION: a, c, t, g, unknown or other
<220> FEATURE:
<221> NAME/KEY: misc_feature
<222> LOCATION: (357)..(377)
<223> OTHER INFORMATION: n is a, c, g, or t

<400> SEQUENCE: 31

```
gtgacacggc ggttagaacg cggctacaat taatacataa ccccatcccc ctgttgacaa        60
ttaatcatcg gctcgtataa tgtgtggaat tgtgagcgga taacaatttc acacaggaaa       120
caggatctac catgctgccg gcgccgaaaa acctggttgt ttctcgcgtt accgaagact       180
ctgcgcgtct gtcttggacc gcgccggacg cggcgttcga ctctttcctg atccagtacc       240
aggaatctga aaaagttggt gaagcgatcg tgctgaccgt tccgggttct gaacgttctt       300
acgacctgac cggtctgaaa ccgggtaccg aatacaccgt ttctatctac ggtgttnnnn       360
nnnnnnnnnn nnnnnntct aacccgctgt ctgcgatctt caccaccggc ggtcaccatc       420
accatcacca tggcagcggt tctagtctag cggccgcaac tgatcttggc                 470
```

<210> SEQ ID NO 32
<211> LENGTH: 88

```
<212> TYPE: PRT
<213> ORGANISM: Unknown
<220> FEATURE:
<223> OTHER INFORMATION: 3rd FN3 domain of tenascin C polypeptide

<400> SEQUENCE: 32

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85

<210> SEQ ID NO 33
<211> LENGTH: 89
<212> TYPE: PRT
<213> ORGANISM: Unknown
<220> FEATURE:
<223> OTHER INFORMATION: Fibcon polypeptide

<400> SEQUENCE: 33

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85

<210> SEQ ID NO 34
<211> LENGTH: 94
<212> TYPE: PRT
<213> ORGANISM: Unknown
<220> FEATURE:
<223> OTHER INFORMATION: 10th FN3 domain of fibronectin polypeptide

<400> SEQUENCE: 34

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
```

```
                        85                  90

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide

<400> SEQUENCE: 35

Gly Ser Gly Ser
1

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Gly Gly Gly Ser Gly Gly Gly Ser
1               5

<210> SEQ ID NO 37
<211> LENGTH: 25
<212> TYPE: PRT
<213> ORGANISM: Artificial Sequence
<220> FEATURE:
<223> OTHER INFORMATION: Synthetic peptide

<400> SEQUENCE: 37

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 38
<211> LENGTH: 4
<212> TYPE: PRT
<213> ORGANISM: Artificial Sequence
<220> FEATURE:
<223> OTHER INFORMATION: Synthetic peptide

<400> SEQUENCE: 38

Ala Pro Ala Pro
1

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

Ala Pro Ala Pro Ala Pro Ala Pro Ala Pro
1               5                   10

<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40
```

Ala Pro Ala Pro Ala Pro Ala Pro Ala Pro Ala Pro Ala Pro
1               5                   10                  15

Ala Pro Ala Pro
            20

<210> SEQ ID NO 41
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 41

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
            35                  40

<210> SEQ ID NO 42
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 42

Glu Ala Ala Ala Lys Glu Ala Ala Ala Lys Glu Ala Ala Ala Lys Glu
1               5                   10                  15

Ala Ala Ala Lys Glu Ala Ala Ala Lys Ala Ala Ala
            20                  25

<210> SEQ ID NO 43
<211> LENGTH: 585
<212> TYPE: PRT
<213> ORGANISM: Artificial Sequence
<220> FEATURE:
<223> OTHER INFORMATION: Synthetic polypeptide

<400> SEQUENCE: 43

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
```

Ala Ala Ser Gln Ala Ala Leu Gly Leu
            580                 585

<210> SEQ ID NO 44
<211> LENGTH: 255
<212> TYPE: PRT
<213> ORGANISM: Homo sapiens

<400> SEQUENCE: 44

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 45
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 45

Leu Pro Ala Pro Lys Asn Leu Val Val Ser Arg Val Thr Glu Asp Ser
1               5                   10                  15

Ala Arg Leu Ser Trp Asp Phe Ala Tyr Phe Lys Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val Gly Arg Phe Tyr Thr Val
65                  70                  75                  80

Tyr Tyr Ser Asn Pro Leu Ser Ala Ile Phe Thr Thr
                85                  90

<210> SEQ ID NO 46
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 46

Leu Pro Ala Pro Lys Asn Leu Val Val Ser Arg Val Thr Glu Asp Ser
1               5                   10                  15

Ala Arg Leu Ser Trp Ser Pro Val Asp Ala Asp Phe Thr Phe Asp Ser
                20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Thr Val Ser Ile Tyr Gly Val Gly Arg His Tyr
65                  70                  75                  80

Thr Val Tyr Asp Ser Asn Pro Leu Ser Ala Ile Phe Thr Thr
                85                  90

<210> SEQ ID NO 47
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 47

Leu Pro Ala Pro Lys Asn Leu Val Val Ser Arg Val Thr Glu Asp Ser
1               5                   10                  15

Ala Arg Leu Ser Trp Lys Trp Ile Ser His Glu Pro Leu Glu Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
        50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95

<210> SEQ ID NO 48
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 48

Leu Pro Ala Pro Lys Asn Leu Val Val Ser Arg Val Thr Glu Asp Ser
1               5                   10                  15

```
Ala Arg Leu Ser Trp Ala Phe Gln Trp His Ile Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Gly Gln Pro Tyr Thr Val
 65                  70                  75                  80

Tyr Asp Ser Asn Pro Leu Ser Ala Ile Phe Thr Thr
                85                  90

<210> SEQ ID NO 49
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 49

Leu Pro Ala Pro Lys Asn Leu Val Val Ser Arg Val Thr Glu Asp Tyr
 1               5                  10                  15

Ala Arg Leu Ser Trp Lys Tyr Gly Glu His Ile Ile Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
 50                  55                  60

Pro Gly Thr Glu Tyr Thr Val Ser Ile Tyr Gly Val Lys Gly Gln His
 65                  70                  75                  80

Asp His Asp Ser Asn Pro Leu Ser Ala Ile Phe Thr Thr
                85                  90

<210> SEQ ID NO 50
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 50

Leu Pro Ala Pro Lys Asn Leu Val Val Ser Arg Val Thr Glu Asp Ser
 1               5                  10                  15

Ala Arg Leu Ser Trp Thr Leu Pro Asn Ile His Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Gly Arg His Tyr Thr Val
 65                  70                  75                  80

Tyr Asp Ser Asn Pro Leu Ser Ala Ile Phe Thr Thr
                85                  90

<210> SEQ ID NO 51
<211> LENGTH: 95
<212> TYPE: PRT
<213> ORGANISM: Artificial Sequence
<220> FEATURE:
<223> OTHER INFORMATION: CD137 Binding Centyrin
```

-continued

<400> SEQUENCE: 51

Leu Pro Ala Pro Lys Asn Leu Val Val Ser Arg Val Thr Glu Asp Ser
1               5                   10                  15

Ala Arg Leu Ser Trp Ser Gln His Tyr Leu Ser Pro Ile Pro Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95

<210> SEQ ID NO 52
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 52

Leu Pro Ala Pro Lys Asn Leu Val Val Ser Arg Val Thr Glu Asp Ser
1               5                   10                  15

Ala Arg Leu Ser Trp His Ala Thr Phe Gly Asp Pro Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
                85                  90

<210> SEQ ID NO 53
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 53

Leu Pro Ala Pro Lys Asn Leu Val Val Ser Arg Val Thr Glu Asp Ser
1               5                   10                  15

Ala Arg Leu Ser Trp Asn Thr Asp Trp Val His Thr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
                85                  90

<210> SEQ ID NO 54
<211> LENGTH: 95

```
<212> TYPE: PRT
<213> ORGANISM: Artificial Sequence
<220> FEATURE:
<223> OTHER INFORMATION: CD137 Binding Centyrin

<400> SEQUENCE: 54
```

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Ala Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95

```
<210> SEQ ID NO 55
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 55
```

Leu Pro Ala Pro Lys Asn Leu Val Val Ser Arg Val Thr Glu Asp Ser
1               5                   10                  15

Ala Arg Leu Ser Trp Asp Gly Asp Lys Trp Ala Asn Phe Lys Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Leu His
65                  70                  75                  80

Tyr Ile Val Tyr Asp Ser Asn Pro Leu Ser Ala Ile Phe Thr Thr
                85                  90                  95

```
<210> SEQ ID NO 56
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 56
```

Leu Pro Ala Pro Lys Asn Leu Val Val Ser Arg Val Thr Glu Asp Ser
1               5                   10                  15

Ala Arg Leu Ser Trp Val Arg Glu Asp Ala Tyr Ala Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Ser Ser Leu His Trp
65                  70                  75                  80

Val Val His Asp Ser Asn Pro Leu Ser Ala Ile Phe Thr Thr

<210> SEQ ID NO 57
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 57

Leu Pro Ala Pro Lys Asn Leu Val Val Ser Arg Val Thr Glu Asp Ser
1               5                   10                  15

Ala Arg Leu Ser Trp Thr Phe His Pro Thr Phe Glu Gly Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Lys Trp Thr Val
65                  70                  75                  80

Leu Arg Pro Trp Leu Ser Asn Pro Leu Ser Ala Ile Phe Thr Thr
                85                  90                  95

<210> SEQ ID NO 58
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 58

Leu Pro Ala Pro Lys Asn Leu Val Val Ser Arg Val Thr Glu Asp Ser
1               5                   10                  15

Ala Arg Leu Ser Trp Ile Arg Lys His Asn His Val Lys Trp Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Phe Leu
65                  70                  75                  80

Ile Asp Thr Asp Asp Ser Asn Pro Leu Ser Ala Ile Phe Thr Thr
                85                  90                  95

<210> SEQ ID NO 59
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 59

Leu Pro Ala Pro Lys Asn Leu Val Val Ser Arg Val Thr Glu Asp Ser
1               5                   10                  15

Ala Arg Leu Ser Trp Ala Gln Glu Leu Asp His Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

```
Thr Glu Tyr Thr Val Ser Ile Tyr Gly Val Tyr Trp Thr Trp Trp Val
65                  70                  75                  80

Arg Trp Asn Ser Asn Pro Leu Ser Ala Ile Phe Thr Thr
                85                  90
```

<210> SEQ ID NO 60
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 60

```
Leu Pro Ala Pro Lys Asn Leu Val Val Ser Arg Val Thr Glu Asp Ser
1               5                   10                  15

Ala Arg Leu Ser Trp Thr Phe His Pro Thr Phe Glu Gly Phe Asp Ser
                20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Thr Val Ser Ile Tyr Gly Val Lys Trp Tyr Ala
65                  70                  75                  80

Gly Ile Gly Tyr Pro Val Ser Asn Pro Leu Ser Ala Ile Phe Thr Thr
                85                  90                  95
```

<210> SEQ ID NO 61
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 61

```
Leu Pro Ala Pro Lys Asn Leu Val Val Ser Arg Val Thr Glu Asp Ser
1               5                   10                  15

Ala Arg Leu Ser Trp Ser Glu His Pro Thr Pro Phe Ala Thr Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
        50                  55                  60

Lys Pro Gly Thr Glu Tyr Thr Val Ser Ile Tyr Gly Val Trp Trp Val
65                  70                  75                  80

Glu Asn His Phe Pro Val Ser Asn Pro Leu Ser Ala Ile Phe Thr Thr
                85                  90                  95
```

<210> SEQ ID NO 62
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 62

```
Leu Pro Ala Pro Lys Asn Leu Val Val Ser Arg Val Thr Glu Asp Ser
1               5                   10                  15

Ala Arg Leu Ser Trp Glu Glu Ser Arg Gln Phe Phe Asp Ser Phe Leu
                20                  25                  30
```

-continued

```
Ile Gln Tyr Gln Glu Ser Glu Lys Val Gly Glu Ala Ile Val Leu Thr
         35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Arg Ala Trp Leu
 65                  70                  75                  80

Arg Trp Asn Gly Ser Asn Pro Leu Ser Ala Ile Phe Thr Thr
                 85                  90

<210> SEQ ID NO 63
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 63

Leu Pro Ala Pro Lys Asn Leu Val Val Ser Arg Val Thr Glu Asp Ser
 1               5                  10                  15

Ala Arg Leu Ser Trp Asp Asp Gln Phe Glu Asp Trp Phe Asp Ser Phe
                 20                  25                  30

Leu Ile Gln Tyr Gln Glu Ser Glu Gln Val Gly Glu Ala Ile Val Leu
             35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Thr Arg Asp Trp
 65                  70                  75                  80

Thr Ala Trp Asn Ala Ser Asn Pro Leu Ser Ala Ile Phe Thr Thr
                 85                  90                  95

<210> SEQ ID NO 64
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 64

Leu Pro Ala Pro Lys Asn Leu Val Val Ser Arg Val Thr Glu Asp Ser
 1               5                  10                  15

Ala Arg Leu Ser Trp Ala Gly His Tyr Arg Lys Ile Arg Asn Phe Asp
                 20                  25                  30

Ser Phe Leu Ile Gln Tyr Gln Glu Ser Glu Lys Val Gly Glu Ala Ile
             35                  40                  45

Val Leu Thr Val Pro Gly Ser Glu Arg Ser Tyr Asp Leu Thr Gly Leu
 50                  55                  60

Lys Pro Gly Thr Glu Tyr Thr Val Ser Ile Tyr Gly Val Lys Phe Pro
 65                  70                  75                  80

Tyr Tyr Tyr Ala Thr Ala Asp Ser Asn Pro Leu Ser Ala Ile Phe Thr
                 85                  90                  95

Thr

<210> SEQ ID NO 65
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 65
```

```
Leu Pro Ala Pro Lys Asn Leu Val Val Ser Arg Val Thr Glu Asp Ser
1               5                   10                  15

Ala Arg Leu Ser Trp Ala Gly His Tyr Arg Lys Ile Arg Asn Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Lys Arg Ser Tyr Asp Leu Thr Gly Leu
    50                  55                  60

Lys Pro Gly Thr Glu Tyr Thr Val Ser Ile Tyr Gly Val Lys Phe Pro
65                  70                  75                  80

Tyr Tyr Tyr Ala Thr Ala Asp Ser Asn Pro Leu Ser Ala Ile Phe Thr
                85                  90                  95

Thr

<210> SEQ ID NO 66
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 66

Leu Pro Ala Pro Lys Asn Leu Val Val Ser Arg Val Thr Glu Asp Ser
1               5                   10                  15

Ala Arg Leu Ser Trp Leu Glu Gly Ala Asn Ala Glu Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Trp Val Gly Pro
65                  70                  75                  80

Trp Tyr Pro Val Ser Asn Pro Leu Ser Ala Ile Phe Thr Thr
                85                  90

<210> SEQ ID NO 67
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 67

Leu Pro Ala Pro Lys Asn Leu Val Val Ser Arg Val Thr Glu Asp Ser
1               5                   10                  15

Ala Arg Leu Ser Trp Gly Ala Lys Thr Arg Gln Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Trp Trp Val Glu Asn His
65                  70                  75                  80

Phe Pro Val Ser Asn Pro Leu Ser Ala Ile Phe Thr Thr
                85                  90

<210> SEQ ID NO 68
```

```
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 68

Leu Pro Ala Pro Lys Asn Leu Val Val Ser Arg Val Thr Glu Asp Ser
1               5                   10                  15

Ala Arg Leu Ser Trp Asn Val Thr Gln Lys Glu Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Asn Arg Tyr Tyr Thr
65                  70                  75                  80

Val Tyr Asp Ser Asn Pro Leu Ser Ala Ile Phe Thr Thr
                85                  90

<210> SEQ ID NO 69
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 69

Leu Pro Ala Pro Lys Asn Leu Val Val Ser Arg Val Thr Glu Asp Ser
1               5                   10                  15

Ala Arg Leu Ser Trp Lys Asn His Thr Gln Glu Trp Glu Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Pro Ile Ala Trp
65                  70                  75                  80

Leu Ala Trp Thr Ser Thr Ser Asn Pro Leu Ser Ala Ile Phe Thr Thr
                85                  90                  95

<210> SEQ ID NO 70
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 70

Leu Pro Ala Pro Lys Asn Leu Val Val Ser Arg Val Thr Glu Asp Ser
1               5                   10                  15

Ala Arg Leu Ser Trp Asn Gly Gly Glu Tyr Trp Val Pro Arg Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Val Trp Leu
65                  70                  75                  80
```

Gln Trp Ile Ser Trp Thr Asp Ser Asn Pro Leu Ser Ala Ile Phe Thr
                85                  90                  95

Thr

<210> SEQ ID NO 71
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 71

Leu Pro Ala Pro Lys Asn Leu Val Val Ser Arg Val Thr Glu Asp Ser
1               5                   10                  15

Ala Arg Leu Ser Trp Ala Val Glu Phe Asn Pro Thr Lys Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Trp Trp Phe Glu
65                  70                  75                  80

Gln Trp Tyr Pro Val Ser Asn Pro Leu Ser Ala Ile Phe Thr Thr
                85                  90                  95

<210> SEQ ID NO 72
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 72

Leu Pro Ala Pro Lys Asn Leu Val Val Ser Arg Val Thr Glu Asp Ser
1               5                   10                  15

Ala Arg Leu Ser Trp Ala Trp Asn Arg His Asp Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Trp Thr Val Leu Arg
65                  70                  75                  80

Pro Phe Ile Asp Ser Asn Pro Leu Ser Ala Ile Phe Thr Thr
                85                  90

<210> SEQ ID NO 73
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 73

Leu Pro Ala Pro Lys Asn Leu Val Val Ser Arg Val Thr Glu Asp Ser
1               5                   10                  15

Ala Arg Leu Ser Trp Thr Ile Asn Ser His Ile Phe Asp Ser Phe Leu
            20                  25                  30

Ile Gln Tyr Gln Glu Ser Glu Lys Val Gly Glu Ala Ile Val Leu Thr
        35                  40                  45

-continued

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Trp Gly Thr Lys Tyr Trp
65                  70                  75                  80

Gln Ala Gln Ser Asn Pro Leu Ser Ala Ile Phe Thr Thr
                85                  90

<210> SEQ ID NO 74
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 74

Leu Pro Ala Pro Lys Asn Leu Val Val Ser Arg Val Thr Glu Asp Ser
1               5                   10                  15

Ala Arg Leu Ser Trp Thr Glu Glu Asp Ile Thr His Leu Arg Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Tyr Trp Thr
65                  70                  75                  80

Trp Trp Val Arg Trp Asn Ser Asn Pro Leu Ser Ala Ile Phe Thr Thr
                85                  90                  95

<210> SEQ ID NO 75
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 75

Leu Pro Ala Pro Lys Asn Leu Val Val Ser Arg Val Thr Glu Asp Ser
1               5                   10                  15

Ala Arg Leu Ser Trp Thr Lys Arg His Phe Tyr Thr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Tyr Leu Thr Gly Leu Lys Pro
    50                  55                  60

Gly Thr Glu Asn Thr Val Ser Ile Tyr Gly Val His Gly Asn His Pro
65                  70                  75                  80

Tyr Thr Asp Ala Pro Ala Asn Pro Leu Ser Ala Ile Phe Thr Thr
                85                  90                  95

<210> SEQ ID NO 76
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 76

Leu Pro Ala Pro Lys Asn Leu Val Val Ser Arg Val Thr Glu Asp Ser
1               5                   10                  15

-continued

Ala Arg Leu Ser Trp Thr Ala Pro Asp Ala Ala Phe Asp Ser Phe Ile
            20                  25                  30

Ile Gln Tyr Ala Glu Asp Ser Ser Trp Gly Glu Ala Ile Asn Leu His
        35                  40                  45

Val Pro Gly Ser Glu Arg Ser Tyr Asp Leu Thr Gly Leu Lys Pro Gly
    50                  55                  60

Thr Glu Tyr His Val His Ile Tyr Gly Val Lys Gly Glu Ala Ser
65                  70                  75                  80

Asn Pro Leu Trp Ala Trp Phe Thr Thr
                85

<210> SEQ ID NO 77
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 77

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Arg Tyr Trp Glu Phe Cys His Ser Gly Glu Ala Ile Glu Leu Ser
        35                  40                  45

Val Pro Gly Ser Glu Arg Ser Tyr Asp Leu Thr Gly Leu Lys Pro Gly
    50                  55                  60

Thr Glu Tyr Phe Val Arg Ile Val Gly Val Lys Gly Arg Val Ser
65                  70                  75                  80

Leu Pro Leu Gly Ala Lys Phe Thr Thr
                85

<210> SEQ ID NO 78
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 78

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Asp Tyr Trp Glu Val Glu Ser Glu Gly Glu Ala Ile Val Leu Phe
        35                  40                  45

Val Pro Gly Ser Glu Arg Ser Tyr Asp Leu Thr Gly Leu Lys Pro Gly
    50                  55                  60

Thr Glu Tyr His Val His Ile Val Gly Val Lys Gly Gly Thr Pro Ser
65                  70                  75                  80

Tyr Pro Leu Trp Ala Asp Phe Thr Thr
                85

<210> SEQ ID NO 79
<211> LENGTH: 95
<212> TYPE: PRT
<213> ORGANISM: Artificial Sequence
<220> FEATURE:
<223> OTHER INFORMATION: CD137 Binding Centyrin

```
<400> SEQUENCE: 79

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95

<210> SEQ ID NO 80
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 80

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Asp Tyr Trp Glu Val Glu Ser Glu Gly Glu Ala Ile Ile Leu Phe
        35                  40                  45

Val Pro Gly Ser Glu Arg Ser Tyr Asp Leu Thr Gly Leu Lys Pro Gly
50                  55                  60

Thr Glu Tyr His Val His Ile Val Gly Val Lys Gly Thr Pro Ser
65                  70                  75                  80

Tyr Pro Leu Trp Ala Asp Phe Thr Thr
                85

<210> SEQ ID NO 81
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 81

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Pro Tyr Ile Glu Val Glu Thr Ile Gly Glu Ala Ile Trp Leu His
        35                  40                  45

Val Pro Gly Ser Glu Arg Ser Tyr Asp Leu Thr Gly Leu Lys Pro Gly
50                  55                  60

Thr Glu Tyr Ser Val Gly Ile Asn Gly Val Lys Gly His Thr Ser
65                  70                  75                  80

Asn Pro Leu Ser Ala Arg Phe Thr Thr
                85

<210> SEQ ID NO 82
<211> LENGTH: 89
```

```
<212> TYPE: PRT
<213> ORGANISM: Artificial Sequence
<220> FEATURE:
<223> OTHER INFORMATION: CD137 Binding Centyrin

<400> SEQUENCE: 82

Leu Pro Ala Pro Lys Asn Leu Val Val Ser Arg Val Thr Glu Asp Ser
1               5                   10                  15

Ala Arg Leu Ser Trp Thr Ala Pro Asp Gly Ala Phe Asp Ser Phe Glu
            20                  25                  30

Ile Pro Tyr Ile Glu Val Glu Thr Ile Gly Glu Ala Ile Trp Leu His
        35                  40                  45

Val Pro Gly Ser Glu Arg Ser Tyr Asp Leu Thr Gly Leu Lys Pro Gly
    50                  55                  60

Thr Glu Tyr Ser Val Gly Ile Asn Gly Val Lys Gly His Thr Ser
65                  70                  75                  80

Asn Pro Leu Ser Ala Arg Phe Thr Thr
                85

<210> SEQ ID NO 83
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 83

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Pro Tyr Trp Glu Trp Thr Thr Glu Gly Glu Ala Ile Gln Leu Ile
        35                  40                  45

Val Pro Gly Ser Glu Arg Ser Tyr Asp Leu Thr Gly Leu Lys Pro Ala
    50                  55                  60

Thr Glu Tyr His Val His Ile Val Gly Val Lys Gly Gly Ser Phe Ser
65                  70                  75                  80

Glu Pro Leu Pro Ala Asp Phe Thr Thr
                85

<210> SEQ ID NO 84
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 84

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Lys Tyr Trp Glu Ala Asn Leu Tyr Gly Glu Ala Ile Val Leu Thr
        35                  40                  45

Val Pro Gly Ser Glu Arg Ser Tyr Gly Leu Thr Gly Leu Lys Pro Gly
    50                  55                  60

Thr Glu Tyr Arg Val His Ile Arg Gly Val Lys Gly Gly Ile Asn Ser
65                  70                  75                  80

Phe Pro Leu Val Ala Val Phe Thr Thr
```

<210> SEQ ID NO 85
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 85

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ala Tyr Trp Glu Tyr Trp Gly Asn Gly Glu Ala Ile Gly Leu Ile
        35                  40                  45

Val Pro Gly Ser Glu Arg Ser Tyr Asp Leu Thr Gly Leu Lys Pro Gly
    50                  55                  60

Thr Glu Tyr His Val His Ile Val Gly Val Lys Gly Gly Ala Gly Ser
65                  70                  75                  80

Val Pro Leu Trp Ala Asn Phe Thr Thr
                85
```

<210> SEQ ID NO 86
<211> LENGTH: 88
<212> TYPE: PRT
<213> ORGANISM: Artificial Sequence
<220> FEATURE:
<223> OTHER INFORMATION: CD137 Binding Centyrin

<400> SEQUENCE: 86

```
Leu Pro Ala Pro Lys Asn Leu Val Val Ser His Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Leu Glu Gly Gly Arg Gly Glu Ala Ile Val Leu Thr Val
        35                  40                  45

Pro Gly Ser Glu Arg Ser Tyr Asp Leu Thr Val Leu Lys Pro Gly Thr
    50                  55                  60

Glu Tyr Leu Gly Thr Ile Tyr Gly Val Lys Cys Gly Trp Ala Ser Asn
65                  70                  75                  80

Pro Leu Ser Ala Ile Phe Thr Thr
                85
```

<210> SEQ ID NO 87
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 87

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Ala Glu Phe Gly Tyr Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60
```

Thr Glu Tyr Thr Val Thr Ile Tyr Gly Val Lys Gly Trp Tyr Ser
65                  70                  75                  80

Thr Pro Leu Ser Ala Ile Phe Thr Thr
                85

<210> SEQ ID NO 88
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 88

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Tyr Tyr Gly Glu Tyr Tyr Asn Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Thr Ile Tyr Gly Val Lys Gly Gly Gly Tyr Ser
65                  70                  75                  80

Asn Pro Leu Ser Ala Ile Phe Thr Thr
                85

<210> SEQ ID NO 89
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 89

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Arg Glu Tyr Trp Tyr Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Trp Tyr Ser
65                  70                  75                  80

Asp Pro Leu Ser Ala Ile Phe Thr Thr
                85

<210> SEQ ID NO 90
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 90

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

```
Ile Leu Tyr Leu Glu Pro Tyr Gln Glu Gly Glu Ala Ile Val Leu Thr
         35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Tyr Tyr Ser
 65                  70                  75                  80

Leu Pro Leu Ser Ala Ile Phe Thr Thr
                 85
```

<210> SEQ ID NO 91
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 91

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ile
                 20                  25                  30

Ile Arg Tyr Ile Glu Glu Gly Tyr Tyr Gly Glu Ala Ile Val Leu Thr
         35                  40                  45

Val Pro Gly Ser Glu Arg Ser Tyr Asp Leu Thr Gly Leu Lys Pro Gly
 50                  55                  60

Thr Glu Tyr His Val Gly Ile Glu Gly Val Lys Gly Tyr Tyr Ser
 65                  70                  75                  80

Tyr Pro Leu Ser Ala Ile Phe Thr Thr
                 85
```

<210> SEQ ID NO 92
<211> LENGTH: 88
<212> TYPE: PRT
<213> ORGANISM: Artificial Sequence
<220> FEATURE:
<223> OTHER INFORMATION: CD137 Binding Centyrin

<400> SEQUENCE: 92

```
Leu Pro Ala Pro Lys Asn Leu Val Val Ser Arg Val Thr Glu Asp Ser
 1               5                  10                  15

Ala Arg Leu Ser Trp Thr Ala Pro Asp Gly Ala Phe Asp Ser Phe Glu
                 20                  25                  30

Ile Tyr Tyr Leu Glu Gly Gly Arg Gly Glu Ala Ile Val Leu Thr Val
         35                  40                  45

Pro Gly Ser Glu Arg Ser Tyr Asp Leu Thr Gly Leu Lys Pro Gly Thr
 50                  55                  60

Glu Tyr Leu Val Thr Ile Tyr Gly Ile Lys Cys Gly Trp Ala Ser Asn
 65                  70                  75                  80

Pro Leu Ser Ala Ile Phe Thr Thr
                 85
```

<210> SEQ ID NO 93
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 93

```
Leu Pro Ala Pro Lys Asn Leu Val Val Ser Arg Val Thr Glu Asp Ser
```

```
1               5                   10                  15
Ala Arg Leu Ser Trp Thr Ala Pro Asp Ala Ala Phe Asp Ser Phe Glu
            20                  25                  30

Ile Tyr Tyr Phe Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
            50                  55                  60

Thr Glu Tyr Leu Val Thr Ile Tyr Gly Val Lys Gly Leu Asp Ser
65                  70                  75                  80

Gln Pro Leu Ser Ala Ile Phe Thr Thr
                85

<210> SEQ ID NO 94
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 94

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Ala Glu Pro Arg Tyr Tyr Gly Glu Ala Ile Val Leu Thr
            35                  40                  45

Val Pro Gly Ser Glu Arg Ser Tyr Asp Leu Thr Gly Leu Lys Pro Gly
            50                  55                  60

Thr Glu Tyr Thr Val Thr Ile Tyr Gly Val Lys Gly Tyr Tyr Ser
65                  70                  75                  80

Ser Pro Leu Ser Ala Ile Phe Thr Thr
                85

<210> SEQ ID NO 95
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 95

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Leu Glu Ser Trp Thr Arg Gly Glu Ala Ile Val Leu Thr
            35                  40                  45

Val Pro Gly Ser Glu Arg Ser Tyr Asp Leu Thr Gly Leu Lys Pro Gly
            50                  55                  60

Thr Glu Tyr Leu Val Thr Ile Tyr Gly Val Lys Gly Gly Ser Tyr Ser
65                  70                  75                  80

Arg Pro Leu Ser Ala Ile Phe Thr Thr
                85

<210> SEQ ID NO 96
<211> LENGTH: 89
<212> TYPE: PRT
<213> ORGANISM: Artificial Sequence
<220> FEATURE:
```

<223> OTHER INFORMATION: CD137 Binding Centyrin

<400> SEQUENCE: 96

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Tyr Tyr Leu Glu Gln Leu Gly Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Val Cys Glu Gln Ser
65                  70                  75                  80

Tyr Pro Leu Ser Ala Ile Phe Thr Thr
                85

<210> SEQ ID NO 97
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 97

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Gly Glu Pro Gly Asn Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Asp Tyr Ser
65                  70                  75                  80

Ser Pro Leu Ser Ala Ile Phe Thr Thr
                85

<210> SEQ ID NO 98
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 98

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Tyr Ser
65                  70                  75                  80

Gly Pro Leu Ser Ala Ile Phe Thr Thr
                85

```
<210> SEQ ID NO 99
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 99

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Arg Glu Leu Asp Phe Gln Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Ile Ile Tyr Gly Val Lys Gly Ser Tyr Ser
65                  70                  75                  80

Tyr Thr Leu Ser Ala Ile Phe Thr Thr
                85

<210> SEQ ID NO 100
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 100

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Tyr Tyr Arg Glu His Trp Thr Ile Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Ala Tyr Ser
65                  70                  75                  80

Asn Pro Leu Ser Ala Ile Phe Thr Thr
                85

<210> SEQ ID NO 101
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 101

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Leu Tyr Gly Glu Pro Pro Ala Leu Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Thr Ile Tyr Gly Val Lys Gly Gly Val Phe Ser
65                  70                  75                  80
```

His Pro Leu Ser Ala Ile Phe Thr Thr
                85

<210> SEQ ID NO 102
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 102

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
            20                  25                  30

Ile Arg Tyr Ile Glu Asp Thr Val Met Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Ser Ile Glu Gly Val Lys Gly Gly Pro Ser Ser
65                  70                  75                  80

Leu Pro Leu Ser Ala Ile Phe Thr Thr
                85

<210> SEQ ID NO 103
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 103

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Met Tyr Leu Glu Asp Val Gln Cys Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Gly Ile Asn Gly Val Lys Gly Gly Leu Arg Ser
65                  70                  75                  80

Phe Pro Leu Ser Ala Ile Phe Thr Thr
                85

<210> SEQ ID NO 104
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 104

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ser Tyr Leu Glu Asp Val Tyr Tyr Gly Glu Ala Ile Val Leu Thr
        35                  40                  45

Val Pro Gly Ser Glu Arg Ser Tyr Asp Leu Thr Gly Leu Lys Pro Gly
        50                  55                  60

Thr Glu Tyr His Val Gly Ile His Gly Val Lys Gly Gly Ile Asp Ser
65                  70                  75                  80

Phe Pro Leu Ser Ala Ile Phe Thr Thr
                85

<210> SEQ ID NO 105
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 105

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Gly Glu His Trp Lys Leu Gly Glu Ala Ile Val Leu Thr
                35                  40                  45

Val Gln Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Gln Trp Ser
65                  70                  75                  80

Phe Pro Leu Ser Ala Ile Phe Thr Thr
                85

<210> SEQ ID NO 106
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 106

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Tyr Tyr Gly Glu Trp His Ala Leu Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Val Val Thr Ile Tyr Gly Val Lys Gly Gly Thr Tyr Ser
65                  70                  75                  80

Leu Pro Leu Ser Ala Ile Ser Thr Thr
                85

<210> SEQ ID NO 107
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 107

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser

```
                  20                  25                  30

Ile Tyr Tyr Gly Glu Trp His Ala Leu Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Thr Ile Tyr Gly Val Lys Gly Thr Tyr Ser
65                  70                  75                  80

Leu Pro Leu Ser Ala Ile Phe Thr Thr
                85

<210> SEQ ID NO 108
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 108

Leu Pro Ala Pro Lys Asn Leu Val Val Ser Arg Val Thr Glu Asp Ser
1               5                  10                  15

Ala Arg Leu Ser Trp Thr Ala Pro Asp Ala Ala Phe Asp Ser Phe Asn
            20                  25                  30

Ile Gly Tyr Tyr Glu Arg Ile Ile Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ser Val Leu Ile Cys Gly Val Lys Gly Lys Gly Ser
65                  70                  75                  80

Ile Pro Leu Ser Ala Ile Phe Thr Thr
                85

<210> SEQ ID NO 109
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 109

Leu Pro Ala Pro Lys Asn Leu Val Val Ser Arg Val Thr Glu Asp Ser
1               5                  10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Tyr Leu Ser
65                  70                  75                  80

Met Pro Leu Ser Ala Ile Phe Thr Thr
                85

<210> SEQ ID NO 110
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 110
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Met Glu Asp Phe His Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Thr Ile Tyr Gly Val Glu Gly Thr Gly Ser
65                  70                  75                  80

Leu Pro Leu Ser Ala Ile Phe Thr Thr
                85

<210> SEQ ID NO 111
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 111

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Lys Glu Leu Arg Ala Glu Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Ser Val Ser
65                  70                  75                  80

Ile Pro Leu Ser Ala Ile Phe Thr Thr
                85

<210> SEQ ID NO 112
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 112

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Tyr Tyr Ile Glu Trp Thr Ala Tyr Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Arg Ile Ser Gly Val Lys Cys Gly Ile Val Ser
65                  70                  75                  80

Phe Pro Leu Ser Ala Ile Phe Thr Thr
                85

<210> SEQ ID NO 113
<211> LENGTH: 89
<212> TYPE: PRT

<213> ORGANISM: Artificial Sequence
<220> FEATURE:
<223> OTHER INFORMATION: CD137 Binding Centyrin

<400> SEQUENCE: 113

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 114
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 114

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Asn Tyr Phe Glu Gln Pro Lys Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Pro Tyr Ser
65                  70                  75                  80

Pro Pro Leu Ser Ala Ile Phe Thr Thr
                85

<210> SEQ ID NO 115
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 115

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Leu Gln
            20                  25                  30

Ile Tyr Tyr Phe Glu Trp Val Val Gly Gly Glu Ala Ile Val Leu Thr
        35                  40                  45

Val Pro Gly Ser Glu Arg Ser Tyr Asp Leu Thr Gly Leu Lys Leu Gly
    50                  55                  60

Thr Glu Tyr Leu Val Thr Ile Tyr Gly Val Lys Gly Asn Phe Ser
65                  70                  75                  80

Asp Pro Leu Ser Ala Ile Phe Thr Thr
                85

<210> SEQ ID NO 116
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 116

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Arg Tyr Leu Glu Asp Ile Ser Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Gly Ile Glu Gly Val Lys Gly Gly Asn Val Ser
65                  70                  75                  80

Phe Pro Leu Ser Ala Ile Phe Thr Thr
                85

<210> SEQ ID NO 117
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 117

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Pro Tyr Leu Glu Asp Ile Glu Val Gly Glu Ala Ile Val Leu Thr
        35                  40                  45

Val Pro Gly Ser Glu Arg Ser Tyr Asp Leu Ala Gly Leu Lys Pro Gly
    50                  55                  60

Thr Glu Tyr His Val Gly Ile Tyr Gly Val Lys Gly Gly Glu Gln Ser
65                  70                  75                  80

Phe Pro Leu Ser Ala Ile Phe Thr Thr
                85

<210> SEQ ID NO 118
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 118

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Arg Tyr Leu Glu Asp Ile Ser Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

```
Thr Glu Tyr His Val Gly Ile Glu Gly Val Lys Gly Gly Asn Val Ser
 65                  70                  75                  80

Trp Pro Leu Ser Ala Ile Phe Thr Thr
                 85
```

<210> SEQ ID NO 119
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 119

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ile
                20                  25                  30

Ile Arg Tyr Leu Glu Asp Ile Ser Tyr Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr His Val Gly Ile Glu Gly Val Lys Gly Gly Asn Val Ser
 65                  70                  75                  80

Trp Pro Leu Ser Ala Ile Phe Thr Thr
                 85
```

<210> SEQ ID NO 120
<211> LENGTH: 87
<212> TYPE: PRT
<213> ORGANISM: Artificial Sequence
<220> FEATURE:
<223> OTHER INFORMATION: CD137 Binding Centyrin

<400> SEQUENCE: 120

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ile
                20                  25                  30

Ile Tyr Tyr Pro Glu Tyr Ile Ser Asn Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr His Val Thr Ile Gly Val Lys Gly Gly His Ser Trp Pro
 65                  70                  75                  80

Leu Ser Ala Ile Phe Thr Thr
                 85
```

<210> SEQ ID NO 121
<211> LENGTH: 88
<212> TYPE: PRT
<213> ORGANISM: Artificial Sequence
<220> FEATURE:
<223> OTHER INFORMATION: CD137 Binding Centyrin

<400> SEQUENCE: 121

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Leu
                20                  25                  30

Ile His Tyr Thr Glu Gln Pro Ser Lys Gly Glu Ala Ile Val Leu Thr
```

```
                35                  40                  45

Val Pro Gly Ser Glu Arg Ser Tyr Asp Leu Thr Gly Leu Lys Pro Gly
 50                  55                  60

Thr Glu Tyr Gln Val Pro Ile Gly Val Lys Gly Gly Thr Gln Ser Cys
 65                  70                  75                  80

Pro Leu Ser Ala Ile Phe Thr Thr
                 85

<210> SEQ ID NO 122
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 122

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Thr
                20                  25                  30

Ile Tyr Tyr Phe Glu Asn Glu Asn Gly Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly His Trp Ser
 65                  70                  75                  80

Arg Pro Leu Ser Ala Ile Phe Thr Thr
                 85

<210> SEQ ID NO 123
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 123

Leu Pro Ala Pro Lys Asn Leu Val Val Ser Arg Val Thr Glu Asp Ser
 1               5                  10                  15

Ala Arg Leu Ser Trp Ala Leu Ser Ser Val His Ala Tyr Phe Asp Ser
                20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
 50                  55                  60

Pro Gly Thr Glu Tyr Thr Val Ser Ile Tyr Gly Val Gln Tyr Val Asp
 65                  70                  75                  80

Gly Phe Phe Lys Ser Asn Pro Leu Ser Ala Ile Phe Thr Thr
                 85                  90

<210> SEQ ID NO 124
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 124

Leu Pro Ala Pro Lys Asn Leu Val Val Ser Arg Val Thr Glu Asp Ser
 1               5                  10                  15
```

Ala Arg Leu Ser Trp Lys Phe Gly Glu Val Ala Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val Gly Arg His Tyr Thr Val
65                  70                  75                  80

Tyr Asp Ser Asn Pro Leu Ser Ala Ile Phe Thr Thr
            85                  90

<210> SEQ ID NO 125
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 125

Leu Pro Ala Pro Lys Asn Leu Val Val Ser Arg Val Thr Glu Asp Ser
1               5                   10                  15

Ala Arg Leu Ser Trp Ala Phe Gln Trp His Ile Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val Gly Arg His Tyr Thr Val
65                  70                  75                  80

Tyr Asp Ser Asn Pro Leu Ser Ala Ile Phe Thr Thr
            85                  90

<210> SEQ ID NO 126
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 126

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
50                  55                  60

Lys Pro Gly Thr Glu Tyr Thr Val Ser Ile Tyr Gly Val Gly Ala Pro
65                  70                  75                  80

Tyr Thr Val Tyr Asp Ser Asn Pro Leu Ser Ala Ile Phe Thr Thr
            85                  90                  95

<210> SEQ ID NO 127
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 127

Leu Pro Ala Pro Lys Asn Leu Val Val Ser Arg Val Thr Glu Asp Ser
1               5                   10                  15

Ala Arg Leu Ser Trp Arg Asp Leu Gln Tyr His Thr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
                85                  90

<210> SEQ ID NO 128
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 128

Leu Pro Ala Pro Lys Asn Leu Val Val Ser Arg Val Thr Glu Asp Ser
1               5                   10                  15

Ala Arg Leu Ser Trp Pro Asn His Ile Ser Ile Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Arg Phe Tyr Thr Val
65                  70                  75                  80

Phe Asp Ser Asn Pro Leu Ser Ala Ile Phe Thr Thr
                85                  90

<210> SEQ ID NO 129
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 129

Leu Pro Ala Pro Lys Asn Leu Val Val Ser Arg Val Thr Glu Asp Ser
1               5                   10                  15

Ala Arg Leu Ser Trp Lys Phe His Ser Pro Thr Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Arg His Tyr Thr Val
65                  70                  75                  80

Tyr Asp Ser Asn Pro Leu Ser Ala Ile Val Thr Thr
                85                  90

<210> SEQ ID NO 130

```
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 130

Leu Pro Ala Pro Lys Asn Leu Val Val Ser Arg Val Thr Glu Asp Ser
1               5                   10                  15

Ala Arg Leu Ser Trp Leu Glu Gln Glu Gln Phe Val Asn His Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gln Tyr Val
65                  70                  75                  80

Asp Gly Phe Phe Lys Ser Asn Pro Leu Ser Ala Ile Phe Thr Thr
                85                  90                  95

<210> SEQ ID NO 131
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 131

Leu Pro Ala Pro Lys Asn Leu Val Val Ser Arg Val Thr Glu Asp Ser
1               5                   10                  15

Ala Arg Leu Ser Trp Pro Leu Phe Ala Ser Asp Leu Asn Ile Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95

<210> SEQ ID NO 132
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 132

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Arg His
65                  70                  75                  80
```

-continued

Tyr Thr Val Tyr Asp Ser Asn Pro Leu Ser Ala Ile Phe Thr Thr
                85                  90                  95

<210> SEQ ID NO 133
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 133

Leu Pro Ala Pro Lys Asn Leu Val Val Ser Arg Val Thr Glu Asp Ser
1               5                   10                  15

Ala Arg Leu Ser Trp Arg Ile Ser Asp Arg Leu Pro Leu Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Gly Arg His Tyr
65                  70                  75                  80

Thr Val Tyr Asp Ser Asn Pro Leu Ser Ala Ile Phe Thr Thr
                85                  90

<210> SEQ ID NO 134
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 134

Leu Pro Ala Pro Lys Asn Leu Val Val Ser Arg Val Thr Glu Asp Ser
1               5                   10                  15

Ala Arg Leu Ser Trp His Ala Thr Phe Gly Asp Pro Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
                85                  90

<210> SEQ ID NO 135
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 135

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu

```
                    50                  55                  60
Lys Pro Gly Thr Glu Tyr Thr Val Ser Ile Tyr Gly Val Gly Arg Phe
 65                  70                  75                  80

Tyr Thr Val Phe Asp Ser Asn Pro Leu Ser Ala Ile Phe Thr Thr
                 85                  90                  95
```

<210> SEQ ID NO 136
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 136

```
Leu Pro Ala Pro Lys Asn Leu Val Val Ser Arg Val Thr Glu Asp Ser
 1               5                  10                  15

Ala Arg Leu Ser Trp Ala Trp Asn Arg His Asp Phe Asp Ser Phe Leu
                20                  25                  30

Ile Gln Tyr Gln Glu Ser Glu Lys Val Gly Glu Ala Ile Val Leu Thr
             35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Trp Thr Val Leu Arg
 65                  70                  75                  80

Pro Phe Ile Asp Ser Asn Pro Leu Ser Ala Ile Phe Thr Thr
                 85                  90
```

<210> SEQ ID NO 137
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 137

```
Leu Pro Ala Pro Lys Asn Leu Val Val Ser Arg Val Thr Glu Asp Ser
 1               5                  10                  15

Ala Arg Leu Ser Trp Pro Asp Glu Ser Arg Pro Val Arg Phe Asp Ser
                20                  25                  30

Phe Leu Ile Gln Tyr Gln Glu Ser Glu Lys Val Gly Glu Ala Ile Val
             35                  40                  45

Leu Thr Val Pro Gly Ser Glu Arg Ser Tyr Asp Leu Thr Gly Leu Lys
 50                  55                  60

Pro Gly Thr Glu Tyr Thr Val Ser Ile Tyr Gly Val Leu Arg Pro Trp
 65                  70                  75                  80

Ile Tyr Ala Thr Asn Asp Ser Asn Pro Leu Ser Ala Ile Phe Thr Thr
                 85                  90                  95
```

<210> SEQ ID NO 138
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 138

```
Leu Pro Ala Pro Lys Asn Leu Val Val Ser Arg Val Thr Glu Asp Ser
 1               5                  10                  15

Ala Arg Leu Ser Trp Gly Ala Ile Thr Ala Leu Phe Asp Ser Phe Leu
                20                  25                  30
```

-continued

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Lys Phe Pro Tyr Tyr Tyr
65                  70                  75                  80

Ala Thr Ala Asp Ser Asn Pro Leu Ser Ala Ile Phe Thr Thr
                85                  90

<210> SEQ ID NO 139
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 139

Leu Pro Ala Pro Lys Asn Leu Val Val Ser Arg Val Thr Glu Asp Ser
1               5                   10                  15

Ala Arg Leu Ser Trp Ala Gly His Tyr Arg Lys Ile Arg Asn Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Lys Phe Pro
65                  70                  75                  80

Tyr Tyr Tyr Ala Thr Ala Asp Ser Asn Pro Leu Ser Ala Ile Phe Thr
                85                  90                  95

Thr

<210> SEQ ID NO 140
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 140

Leu Pro Ala Pro Lys Asn Leu Val Val Ser Arg Val Thr Glu Asp Ser
1               5                   10                  15

Ala Arg Leu Ser Trp Ala Gly His Tyr Arg Lys Ile Arg Asn Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Ala Glu His
65                  70                  75                  80

Trp Tyr Tyr Ala Thr Gln Asp Ser Asn Pro Leu Ser Ala Ile Phe Thr
                85                  90                  95

Thr

<210> SEQ ID NO 141
<211> LENGTH: 93
<212> TYPE: PRT
<213> ORGANISM: Artificial Sequence
<220> FEATURE:

<223> OTHER INFORMATION: CD137 Binding Centyrin

<400> SEQUENCE: 141

Leu Pro Ala Pro Lys Asn Leu Val Val Ser Arg Val Thr Glu Asp Ser
1               5                   10                  15

Ala Arg Leu Ser Trp Ala Gln Ser Asn Gln Gln Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Val Trp Gln Asn Trp Val
65                  70                  75                  80

Ala Tyr Asn Ser Asn Pro Leu Ser Ala Ile Phe Thr Thr
            85                  90

<210> SEQ ID NO 142
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 142

Leu Pro Ala Pro Lys Asn Leu Val Val Ser Arg Val Thr Glu Asp Ser
1               5                   10                  15

Ala Arg Leu Ser Trp Asp Asp Gln Phe Glu Asp Trp Phe Asp Ser Phe
            20                  25                  30

Leu Ile Gln Tyr Gln Glu Ser Glu Gln Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Thr Arg Asp Trp
65                  70                  75                  80

Thr Ala Trp Asn Ala Ser Asn Pro Leu Ser Ala Ile Phe Thr Thr
            85                  90                  95

<210> SEQ ID NO 143
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 143

Leu Pro Ala Pro Lys Asn Leu Val Val Ser Arg Val Thr Glu Asp Ser
1               5                   10                  15

Ala Arg Leu Ser Trp Lys Gln Val Thr Val Ala Pro Glu Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Lys Phe Pro Tyr
65                  70                  75                  80

Tyr Tyr Ala Thr Ala Asp Ser Asn Pro Leu Ser Ala Ile Phe Thr Thr
            85                  90                  95

```
<210> SEQ ID NO 144
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 144

Leu Pro Ala Pro Lys Asn Leu Val Val Ser Arg Val Thr Glu Asp Ser
1               5                   10                  15

Ala Arg Leu Ser Trp Pro Asp Glu Ser Arg Pro Val Arg Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val His Thr Arg Asp
65                  70                  75                  80

Trp Thr Ala Trp Asn Ala Ser Asn Pro Leu Ser Ala Ile Phe Thr Thr
                85                  90                  95

<210> SEQ ID NO 145
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 145

Leu Pro Ala Pro Lys Asn Leu Val Val Ser Arg Val Thr Glu Asp Ser
1               5                   10                  15

Ala Arg Leu Ser Trp Asn Arg Leu Asp Ser Glu Trp Val Ala Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Phe Arg
65                  70                  75                  80

Pro Trp Leu Ala Tyr Asn Ser Asn Pro Leu Ser Ala Ile Phe Thr Thr
                85                  90                  95

<210> SEQ ID NO 146
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 146

Leu Pro Ala Pro Lys Asn Leu Val Val Ser Arg Val Thr Glu Asp Ser
1               5                   10                  15

Ala Arg Leu Ser Trp Pro Asp Glu Ser Arg Pro Val Arg Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Val Gly Gln Trp
65                  70                  75                  80
```

```
Lys Tyr Ala Thr Ala Asp Ser Asn Pro Leu Ser Ala Ile Phe Thr Thr
                85                  90                  95

<210> SEQ ID NO 147
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 147

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly His Phe Ser
65                  70                  75                  80

Gly Pro Leu Ser Ala Ile Phe Thr Thr
                85

<210> SEQ ID NO 148
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 148

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gln Tyr Gln Glu Tyr Val Ala His Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Arg Ile Ser Gly Val Lys Gly Gly Gly Val Ser
65                  70                  75                  80

Trp Pro Leu Ser Ala Ile Phe Thr Thr
                85

<210> SEQ ID NO 149
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 149

Leu Pro Ala Pro Lys Asn Leu Val Val Ser Arg Val Thr Glu Asp Ser
1               5                   10                  15

Ala Arg Leu Ser Trp Thr Thr Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45
```

```
Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Leu Ser
65                  70                  75                  80

Lys Pro Leu Ser Ala Ile Phe Thr Thr
                85
```

<210> SEQ ID NO 150
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 150

```
Leu Pro Ala Pro Lys Asn Leu Ile Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Lys Glu Leu Arg Ala Glu Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Ser Val Ser
65                  70                  75                  80

Ile Pro Leu Ser Ala Ile Phe Thr Thr
                85
```

<210> SEQ ID NO 151
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 151

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Leu Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Leu Ser
65                  70                  75                  80

Met Pro Leu Ser Ala Ile Phe Thr Thr
                85
```

<210> SEQ ID NO 152
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 152

```
Leu Pro Ala Pro Lys Asn Leu Val Val Ser His Val Thr Glu Asp Ser
1               5                   10                  15

Ala Arg Leu Ser Trp Thr Ala Pro Asp Ala Ala Phe Asp Ser Phe Asp
```

```
            20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Tyr Leu Ser
65                  70                  75                  80

Met Pro Leu Ser Ala Ile Phe Thr Thr
                85

<210> SEQ ID NO 153
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 153

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gln Tyr Gln Glu Tyr Val Ala His Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Arg Ile Ser Gly Val Lys Gly Gly Val Ser
65                  70                  75                  80

Trp Pro Leu Ser Ala Ile Val Thr Thr
                85

<210> SEQ ID NO 154
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 154

Leu Leu Ala Pro Lys Asn Leu Val Val Ser Arg Val Thr Glu Asp Ser
1               5                   10                  15

Ala Arg Leu Ser Trp Ile Ala Pro Asp Ala Ala Phe Asp Ser Phe Glu
            20                  25                  30

Ile Tyr Tyr Lys Glu Leu Arg Ala Glu Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Ser Val Ser
65                  70                  75                  80

Ile Pro Leu Ser Ala Ile Phe Thr Thr
                85

<210> SEQ ID NO 155
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 155
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Ile Trp Ser
65                  70                  75                  80

Val Pro Leu Ser Ala Ile Phe Thr Thr
                85

<210> SEQ ID NO 156
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 156

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Thr Tyr Ser
65                  70                  75                  80

Leu Pro Leu Ser Ala Ile Phe Thr Thr
                85

<210> SEQ ID NO 157
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 157

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Glu Leu Ser
65                  70                  75                  80

Lys Pro Leu Ser Ala Ile Ser Thr Thr
                85

<210> SEQ ID NO 158
<211> LENGTH: 89
<212> TYPE: PRT

<213> ORGANISM: Artificial Sequence
<220> FEATURE:
<223> OTHER INFORMATION: CD137 Binding Centyrin

<400> SEQUENCE: 158

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Thr Tyr Ser
65                  70                  75                  80

Pro Pro Leu Ser Ala Ile Phe Thr Thr
                85

<210> SEQ ID NO 159
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 159

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Gly Glu His Trp Lys Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Met Ser Ser
65                  70                  75                  80

Asn Pro Leu Ser Ala Ile Phe Thr Thr
                85

<210> SEQ ID NO 160
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 160

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Ser Val Ser
65                  70                  75                  80

Ile Pro Leu Ser Ala Ile Phe Thr Thr
                85

<210> SEQ ID NO 161
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 161

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Phe Trp Ser
65                  70                  75                  80

Gln Pro Leu Ser Ala Ile Phe Thr Thr
                85

<210> SEQ ID NO 162
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 162

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ile Tyr Gln Glu Tyr Val Lys Ser Gly Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Arg Ile Gly Gly Val Lys Gly Leu Leu Ser
65                  70                  75                  80

Leu Pro Leu Ser Ala Ile Phe Thr Thr
                85

<210> SEQ ID NO 163
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 163

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

```
Thr Glu Tyr Leu Val Thr Ile Tyr Gly Val Lys Gly Gly Glu Leu Ser
 65                  70                  75                  80

Lys Pro Leu Ser Ala Ile Phe Thr Thr
                 85

<210> SEQ ID NO 164
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 164

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
            20                  25                  30

Ile Gln Tyr Gln Glu Tyr Val Ala His Gly Glu Ala Ile Val Leu Thr
         35                  40                  45

Val Pro Gly Ser Glu Arg Ser Tyr Asp Leu Thr Gly Leu Lys Pro Gly
     50                  55                  60

Thr Glu Tyr His Val Arg Ile Ser Gly Val Lys Gly Gly Gly Val Ser
 65                  70                  75                  80

Trp Pro Leu Ser Ala Ile Ser Thr Thr
                 85

<210> SEQ ID NO 165
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 165

Leu Pro Ala Pro Lys Asn Leu Val Val Ser Arg Val Thr Glu Asp Ser
 1               5                  10                  15

Ala His Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
         35                  40                  45

Val Pro Gly Ser Glu Arg Ser Tyr Asp Leu Thr Gly Leu Lys Pro Gly
     50                  55                  60

Thr Glu Tyr Leu Val Thr Ile Tyr Gly Val Lys Gly Gly Tyr Leu Ser
 65                  70                  75                  80

Met Pro Leu Ser Ala Ile Phe Thr Thr
                 85

<210> SEQ ID NO 166
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 166

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe His
            20                  25                  30

Ile Tyr Tyr Gly Glu His Tyr Asn Leu Gly Glu Ala Ile Val Leu Thr
```

```
                 35                  40                  45

Val Pro Gly Ser Glu Arg Ser Tyr Asp Leu Thr Gly Leu Lys Pro Gly
             50                  55                  60

Thr Glu Tyr Leu Val Thr Ile Tyr Gly Val Lys Gly Phe Trp Ser
 65                  70                  75                  80

Thr Pro Leu Ser Ala Ile Phe Thr Thr
                 85

<210> SEQ ID NO 167
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 167

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asp
                 20                  25                  30

Ile Tyr Tyr Phe Glu His Pro Val Gly Gly Glu Ala Ile Val Leu Thr
             35                  40                  45

Val Pro Gly Ser Glu Arg Ser Tyr Asp Leu Thr Gly Leu Lys Pro Gly
             50                  55                  60

Thr Glu Tyr Leu Val Thr Ile Tyr Gly Val Lys Gly Gly Tyr Leu Ser
 65                  70                  75                  80

Met Pro Leu Ser Ala Ile Phe Thr Thr
                 85

<210> SEQ ID NO 168
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 168

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asp
                 20                  25                  30

Ile Tyr Tyr Phe Glu Gln Pro Val Gly Gly Glu Ala Ile Val Leu Thr
             35                  40                  45

Val Pro Gly Ser Glu Arg Ser Tyr Asp Leu Thr Gly Leu Lys Pro Gly
             50                  55                  60

Thr Glu Tyr Leu Val Thr Ile Tyr Gly Val Lys Gly Gly Tyr Leu Ser
 65                  70                  75                  80

Met Pro Leu Ser Ala Ile Phe Thr Thr
                 85

<210> SEQ ID NO 169
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 169

Leu Pro Ala Pro Lys Asn Leu Val Val Ser Arg Val Thr Glu Asp Ser
 1               5                  10                  15
```

```
Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly Asn Phe Ser
 65                  70                  75                  80

Phe Pro Leu Ser Ala Ile Phe Thr Thr
                85

<210> SEQ ID NO 170
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 170

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly Tyr Leu Ser
 65                  70                  75                  80

Met Pro Leu Ser Ala Ile Phe Thr Thr
                85

<210> SEQ ID NO 171
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 171

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly Asn Gly Ser
 65                  70                  75                  80

Ser Pro Leu Ser Ala Ile Phe Thr Thr
                85

<210> SEQ ID NO 172
<211> LENGTH: 89
<212> TYPE: PRT
<213> ORGANISM: Artificial Sequence
<220> FEATURE:
<223> OTHER INFORMATION: CD137 Binding Centyrin
```

```
<400> SEQUENCE: 172

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Ala Ile Tyr Gly Val Lys Gly Val Phe Ser
65                  70                  75                  80

His Pro Leu Ser Ala Ile Phe Thr Thr
                85

<210> SEQ ID NO 173
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 173

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
                20                  25                  30

Ile Ser Tyr Leu Glu Asp Val Tyr Tyr Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Gly Ile His Gly Val Lys Gly Ile Asp Ser
65                  70                  75                  80

Phe Pro Leu Ser Ala Ile Phe Thr Thr
                85

<210> SEQ ID NO 174
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 174

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Leu Glu Val Arg Asn Arg Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Gly Ile Ala Gly Val Lys Gly Gly Phe His Ser
65                  70                  75                  80

Phe Pro Leu Ser Ala Ile Phe Thr Thr
                85

<210> SEQ ID NO 175
```

```
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 175

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gln Tyr Trp Glu Gly Trp Glu Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly His Trp Ser
65                  70                  75                  80

Arg Pro Leu Ser Ala Ile Phe Thr Thr
                85

<210> SEQ ID NO 176
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 176

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Ile Glu Pro Ile Ala Pro Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Trp Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 177
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 177

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Phe Glu Asn Glu Asn Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80
```

```
Asp Pro Leu Ser Ala Ile Phe Thr Thr
            85

<210> SEQ ID NO 178
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 178

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Tyr Tyr Leu Glu Gln Tyr Ser Arg Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
            85

<210> SEQ ID NO 179
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 179

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Tyr Tyr Phe Glu Trp Val Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
            85

<210> SEQ ID NO 180
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 180

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Gln Tyr Leu Glu Asp Val Thr Asn Gly Glu Ala Ile Val Leu Thr
        35                  40                  45

Val Pro Gly Ser Glu Arg Ser Tyr Asp Leu Thr Gly Leu Lys Pro Gly
```

```
                    50                  55                  60
Thr Glu Tyr Arg Val Pro Ile Ala Gly Val Lys Gly Arg Asp Ser
65                  70                  75                  80

Gln Pro Leu Ser Ala Ile Phe Thr Thr
                85
```

<210> SEQ ID NO 181
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 181

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Arg Tyr Ile Glu Asp Val Asp Phe Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 182
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 182

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Ala Glu Tyr Phe Lys Asn Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Asp Trp Ser
65                  70                  75                  80

Asp Pro Leu Ser Ala Ile Ser Thr Thr
                85
```

<210> SEQ ID NO 183
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 183

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
                20                  25                  30
```

Ile Arg Tyr Leu Glu Asp Ile Ser Tyr Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr His Val Gly Ile Glu Gly Val Lys Gly Asn Val Ser
65                  70                  75                  80

Trp Pro Leu Ser Ala Ile Phe Thr Thr
                85

<210> SEQ ID NO 184
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 184

Leu Pro Ala Pro Lys Asn Leu Val Val Ser Arg Val Thr Glu Asp Ser
1               5                   10                  15

Ala Arg Leu Ser Trp Thr Thr Pro Asp Ala Ala Phe Asp Ser Phe His
            20                  25                  30

Ile His Tyr Leu Glu Gly Glu Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 185
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 185

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Asn Tyr Phe Glu Asn Glu Leu Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 186
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 186

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly His Trp Ser
65                  70                  75                  80

Arg Pro Leu Ser Ala Ile Phe Thr Thr
                85

<210> SEQ ID NO 187
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 187

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 188
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 188

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
            35                  40                  45

Val Pro Gly Ser Glu Arg Ser Tyr Asp Leu Thr Gly Leu Lys Pro Asp
        50                  55                  60

Thr Glu Tyr Leu Val Thr Ile Tyr Gly Val Lys Gly Gly His Trp Ser
65                  70                  75                  80

Arg Pro Leu Ser Ala Ile Phe Thr Thr
                85

<210> SEQ ID NO 189
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 189

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Phe Glu Asn Glu Leu Gly Gly Glu Ala Ile Val Leu Thr
35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Asp Trp Ser
65                  70                  75                  80

Asp Pro Leu Ser Ala Ile Phe Thr Thr
                85
```

<210> SEQ ID NO 190
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 190

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile His Tyr Leu Glu Gly Glu Trp Gly Gly Glu Ala Ile Val Leu Thr
35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 191
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 191

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Phe Glu Asn Glu Leu Gly Gly Glu Ala Ile Val Leu Thr
35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 192
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 192

```
Leu Pro Ala Pro Lys Asn Leu Phe Val Ser Arg Val Thr Glu Asp Ser
1               5                   10                  15

Ala Arg Leu Ser Trp Thr Ala Pro Asp Ala Ala Phe Asp Ser Phe Gln
                20                  25                  30

Ile Tyr Tyr Arg Glu Gln Trp Trp Asp Gly Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 193
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 193

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Asn Tyr Phe Glu Gln Pro Lys Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 194
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 194

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Asp Glu Leu Arg Asn Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ala Val Thr Ile Tyr Gly Val Lys Gly Gly Arg Tyr Ser
```

```
65                  70                  75                  80
Pro Pro Leu Ser Ala Ile Phe Thr Thr
                85

<210> SEQ ID NO 195
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 195

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Phe Tyr His Glu Phe Ala Asn Pro Gly Glu Ala Ile Asp Leu Pro
        35                  40                  45

Val Pro Gly Ser Glu Arg Ser Tyr Asp Leu Thr Gly Leu Lys Pro Gly
    50                  55                  60

Thr Glu Tyr Asp Val Arg Ile Tyr Gly Val Lys Gly Thr Ala Ser
65                  70                  75                  80

Ile Pro Leu Asp Ala Glu Phe Thr Thr
                85

<210> SEQ ID NO 196
<211> LENGTH: 90
<212> TYPE: PRT
<213> ORGANISM: Artificial Sequence
<220> FEATURE:
<223> OTHER INFORMATION: CD137 Binding Centyrin

<400> SEQUENCE: 196

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Val Glu Trp Thr Ala Asn Gly Glu Ala Ile Val Leu Ile
        35                  40                  45

Val Pro Gly Ser Glu Arg Ser Tyr Asp Leu Thr Gly Leu Lys Pro Gly
    50                  55                  60

Thr Glu Tyr Val Val Arg Ile Arg Gly Val Lys Gly Gly Asp Ser
65                  70                  75                  80

Ser Phe Pro Leu Arg Ala Asp Phe Thr Thr
                85                  90

<210> SEQ ID NO 197
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 197

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ser Tyr Thr Glu Ser Ile Arg Gln Gly Glu Ala Ile Trp Leu Trp
        35                  40                  45
```

Val Pro Gly Ser Glu Arg Ser Tyr Asp Leu Thr Gly Leu Lys Pro Gly
         50                  55                  60

Thr Glu Tyr Glu Val Thr Ile Gly Gly Val Lys Gly Gly Ile Arg Ser
 65                  70                  75                  80

Tyr Pro Leu Trp Ala Trp Phe Thr Thr
                 85

<210> SEQ ID NO 198
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 198

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Glu
                20                  25                  30

Ile Asp Tyr Trp Glu Val Glu Ser Glu Gly Glu Ala Ile Val Leu Phe
             35                  40                  45

Val Pro Gly Ser Glu Arg Ser Tyr Asp Leu Thr Gly Leu Lys Pro Gly
         50                  55                  60

Thr Glu Tyr His Val His Ile Val Gly Val Lys Gly Gly Thr Pro Ser
 65                  70                  75                  80

Tyr Pro Leu Trp Ala Asp Phe Thr Thr
                 85

<210> SEQ ID NO 199
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 199

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asp
                20                  25                  30

Ile Pro Tyr Val Glu Tyr Tyr Pro Ser Gly Glu Ala Ile Val Leu Asn
             35                  40                  45

Val Pro Gly Ser Glu Arg Ser Tyr Asp Leu Thr Gly Leu Lys Pro Gly
         50                  55                  60

Thr Glu Tyr Gly Val Thr Ile Trp Gly Ile Lys Gly Gly Asn Glu Ser
 65                  70                  75                  80

Val Pro Leu Thr Ala Arg Phe Thr Thr
                 85

<210> SEQ ID NO 200
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 200

Leu Pro Ala Pro Lys Asn Leu Val Val Ser Arg Val Thr Glu Asp Ser
 1               5                  10                  15

```
Ala Arg Leu Ser Trp Thr Ala Pro Asp Ala Ala Phe Asp Ser Phe Ala
            20                  25                  30

Ile Phe Tyr His Glu Phe Ala Asn Ser Gly Glu Ala Ile Asp Leu Pro
        35                  40                  45

Val Pro Gly Ser Glu Arg Ser Tyr Asp Leu Thr Gly Leu Lys Pro Gly
    50                  55                  60

Thr Glu Tyr Asp Val Arg Ile Tyr Gly Val Lys Gly Thr Ala Ser
65                  70                  75                  80

Ile Pro Leu Asp Ala Glu Phe Thr Thr
                85

<210> SEQ ID NO 201
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 201

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Pro Tyr Ile Glu Val Glu Thr Ile Gly Glu Ala Ile Trp Leu His
        35                  40                  45

Val Pro Gly Ser Glu Arg Ser Tyr Asp Leu Thr Gly Leu Lys Pro Gly
    50                  55                  60

Thr Glu Tyr Ser Val Gly Ile Asn Gly Val Lys Gly Gly His Thr Ser
65                  70                  75                  80

Asn Pro Leu Ser Ala Arg Phe Thr Thr
                85

<210> SEQ ID NO 202
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 202

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Leu Glu Pro Trp Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Thr Ile Tyr Gly Val Lys Val Cys Leu Gly Ser
65                  70                  75                  80

Asn Pro Leu Ser Ala Ile Phe Thr Thr
                85

<210> SEQ ID NO 203
<211> LENGTH: 88
<212> TYPE: PRT
<213> ORGANISM: Artificial Sequence
<220> FEATURE:
<223> OTHER INFORMATION: CD137 Binding Centyrin
```

<400> SEQUENCE: 203

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Leu Glu Gly Gly Arg Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Leu Val Thr Ile Tyr Gly Val Lys Cys Gly Trp Ala Ser Asn
65                  70                  75                  80

Pro Leu Ser Ala Ile Phe Thr Thr
                85

<210> SEQ ID NO 204
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 204

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Gly Tyr Ser
65                  70                  75                  80

Ala Pro Leu Ser Ala Ile Val Thr Thr
                85

<210> SEQ ID NO 205
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 205

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Ser Ile Tyr Gly Val Lys Gly Cys Gly Tyr Ser
65                  70                  75                  80

Asp Pro Leu Ser Ala Ile Phe Thr Thr
                85

<210> SEQ ID NO 206
<211> LENGTH: 89

```
<212> TYPE: PRT
<213> ORGANISM: Artificial Sequence
<220> FEATURE:
<223> OTHER INFORMATION: CD137 Binding Centyrin

<400> SEQUENCE: 206
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Val Cys Asn Ala Ser
65                  70                  75                  80

Thr Pro Leu Ser Ala Ile Phe Thr Thr
                85

```
<210> SEQ ID NO 207
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 207
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Phe Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Gly Tyr Ser
65                  70                  75                  80

Asp Pro Leu Ser Ala Ile Phe Thr Thr
                85

```
<210> SEQ ID NO 208
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 208
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Phe Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Ser Ile Tyr Gly Val Lys Gly Cys Gly Tyr Ser
65                  70                  75                  80

Asp Pro Leu Ser Ala Ile Phe Thr Thr

<210> SEQ ID NO 209
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 209

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Leu Glu Leu Asp Ser Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ile Val Thr Ile Tyr Gly Val Lys Val Cys Thr Gly Ser
65                  70                  75                  80

Arg Pro Leu Ser Ala Ile Phe Thr Thr
            85

<210> SEQ ID NO 210
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 210

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Phe Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Gly Tyr Ser
65                  70                  75                  80

Thr Pro Leu Ser Ala Ile Phe Thr Thr
            85

<210> SEQ ID NO 211
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 211

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Val Cys Glu Gln Ser
65                  70                  75                  80

Tyr Pro Leu Ser Ala Ile Phe Thr Thr
                85

<210> SEQ ID NO 212
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 212

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Leu Glu Ser Gly Arg Asp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Ser Ile Tyr Gly Val Lys Gly Cys Gly Tyr Ser
65                  70                  75                  80

Asp Pro Leu Ser Ala Ile Phe Thr Thr
                85

<210> SEQ ID NO 213
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 213

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Leu Glu Trp Cys Ser Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Ala Ala Ser
65                  70                  75                  80

Asp Pro Leu Ser Ala Ile Phe Thr Thr
                85

<210> SEQ ID NO 214
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 214

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

-continued

```
Ile Tyr Tyr Phe Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly Ala Tyr Ser
 65                  70                  75                  80

Asn Pro Leu Ser Ala Ile Phe Thr Thr
                85

<210> SEQ ID NO 215
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 215

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Glu
                20                  25                  30

Ile Tyr Tyr Ala Glu Phe Gly Tyr Tyr Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Cys Ala Ala Ser
 65                  70                  75                  80

Asp Pro Leu Ser Ala Ile Phe Thr Thr
                85

<210> SEQ ID NO 216
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 216

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly Asp Tyr Ser
 65                  70                  75                  80

Pro Pro Leu Ser Ala Ile Phe Thr Thr
                85

<210> SEQ ID NO 217
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 217

Leu Pro Ala Pro Lys Asn Leu Val Val Ser Arg Val Thr Glu Asp Ser
```

```
                1               5                   10                  15
Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Tyr Tyr Ser
65                  70                  75                  80

Gly Pro Leu Ser Ala Ile Phe Thr Thr
                85

<210> SEQ ID NO 218
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 218

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Val Cys Tyr Tyr Ser
65                  70                  75                  80

Thr Pro Leu Ser Ala Ile Phe Thr Thr
                85

<210> SEQ ID NO 219
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 219

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Phe Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Asp Tyr Ser
65                  70                  75                  80

Pro Pro Leu Ser Ala Ile Ser Thr Thr
                85

<210> SEQ ID NO 220
<211> LENGTH: 89
<212> TYPE: PRT
<213> ORGANISM: Artificial Sequence
<220> FEATURE:
```

<223> OTHER INFORMATION: CD137 Binding Centyrin

<400> SEQUENCE: 220

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Phe Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Asp Tyr Ser
65                  70                  75                  80

Pro Pro Leu Ser Ala Ile Phe Thr Thr
                85

<210> SEQ ID NO 221
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 221

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Ala Ala Ser
65                  70                  75                  80

Asp Pro Leu Ser Ala Ile Phe Thr Thr
                85

<210> SEQ ID NO 222
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 222

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Val Cys Glu Gln Ser
65                  70                  75                  80

Tyr Pro Leu Ser Ala Ile Ser Thr Thr
                85

<210> SEQ ID NO 223
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 223

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Val Cys Leu Gly Ser
65                  70                  75                  80

Asn Pro Leu Ser Ala Ile Phe Thr Thr
                85
```

<210> SEQ ID NO 224
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 224

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Arg Glu Pro His Tyr Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Thr Ile Tyr Gly Val Lys Val Cys Leu Gly Ser
65                  70                  75                  80

Asn Pro Leu Ser Ala Ile Phe Thr Thr
                85
```